US010494643B2

(12) United States Patent
Schultheiss et al.

(10) Patent No.: US 10,494,643 B2
(45) Date of Patent: Dec. 3, 2019

(54) FUNGAL RESISTANT PLANTS EXPRESSING OCP3

(71) Applicant: BASF Plant Science Company GmbH, Ludwigshafen (DE)

(72) Inventors: Holger Schultheiss, Boehl-Iggelheim (DE); Nadine Tresch, Kirchheim (DE)

(73) Assignee: BASF PLANT SCIENCE COMPANY GMBH, Ludwigshafen (DE)

( * ) Notice: Subject to any disclaimer, the term of this patent is extended or adjusted under 35 U.S.C. 154(b) by 753 days.

(21) Appl. No.: 14/391,244

(22) PCT Filed: Mar. 15, 2013

(86) PCT No.: PCT/EP2013/055319
§ 371 (c)(1),
(2) Date: Oct. 8, 2014

(87) PCT Pub. No.: WO2013/152917
PCT Pub. Date: Oct. 17, 2013

(65) Prior Publication Data
US 2015/0052629 A1  Feb. 19, 2015

Related U.S. Application Data

(60) Provisional application No. 61/622,538, filed on Apr. 11, 2012.

(30) Foreign Application Priority Data

Apr. 11, 2012 (EP) ..................................... 12163703

(51) Int. Cl.
*C12N 15/82* (2006.01)
*A01H 5/10* (2018.01)
(52) U.S. Cl.
CPC ........... *C12N 15/8282* (2013.01); *A01H 5/10* (2013.01)
(58) Field of Classification Search
CPC .............................................. C12N 15/8282
See application file for complete search history.

(56) References Cited

U.S. PATENT DOCUMENTS 7,238,860 B2 * 7/2007 Ratcliffe .............. C07K 14/415
800/289
2014/0137284 A1  5/2014 Schultheiss et al.

FOREIGN PATENT DOCUMENTS

| EP | 1 911 845 A2 * | 4/2008 |
|---|---|---|
| EP | 1911845 | 4/2008 |
| EP | 2085480 | 8/2009 |
| WO | WO 2012023099 | 2/2012 |
| WO | WO 2012023111 | 2/2012 |
| WO | WO 2012172498 | 12/2012 |
| WO | WO 2013001435 | 1/2013 |
| WO | WO 2013092275 | 6/2013 |
| WO | WO 2013093738 | 6/2013 |
| WO | WO 2013149801 | 10/2013 |
| WO | WO 2013149804 | 10/2013 |
| WO | WO 2014024079 | 2/2014 |
| WO | WO 2014024090 | 2/2014 |
| WO | WO 2014024102 | 2/2014 |
| WO | WO 2014041444 | 3/2014 |
| WO | WO 2014076614 | 5/2014 |
| WO | WO 2014117988 | 8/2014 |
| WO | WO 2014117990 | 8/2014 |
| WO | WO 2014118018 | 8/2014 |

OTHER PUBLICATIONS

Coego et al, 2005 The Plant Cell 17: 2123-2137.*
Zhu et al 2004, Proceeding of the National Academy of Science USA 101(26): 9873-9878.*
Garcia-Andrade et al, Jun. 21, 2011 The Plant Journal 67: 783-794.*
Beckers and Spoel, "Fine-Tuning Plant Defence Signalling: Salicylate Versus Jasmonate," Plant Biol., vol. 8, (2006), pp. 1-10.
Coego et al., "An *Arabidopsis* Homeodomain Transcription Factor, *Overexpressor of Cationic Peroxidase 3*, Mediates Resistance to Infection by Necrotrophic Pathogens," The Plant Cell, vol. 17, (2005), pp. 2123-2137.
European Search Report, issued in European Patent Application No. 12163703.7, dated Sep. 12, 2012.
Garcia-Andrade et al., "*Arabidopsis* OCP3 Mutant Reveals a Mechanism Linking ABA and JA to Pathogen-Induced Callose Deposition," The Plant Journal, vol. 67, No. 4, (2011), pp, 783-794. [retrieved on-line]onlinelibrary.wiley.com/doi/10.1111/j.1365-313X.2011.04633.x/suppinfo [retrieved Sep. 3, 2012].
Heath, "Cellular Interactions Between Biotrophic Fungal Pathogens and Host or Nonhost Plants," Can. J. Plant Pathol., vol. 24, (2002), pp. 259-264.
International Preliminary Report on Patentability, issued in PCT/EP2013/055319, dated Oct. 23, 2014.

(Continued)

*Primary Examiner* — David H Kruse
(74) *Attorney, Agent, or Firm* — Marshall, Gerstein & Borun LLP

(57) ABSTRACT

The present invention relates to a method of increasing resistance against fungal pathogens of the family Phacosporaceae in plants and/or plant cells. This is achieved by increasing the expression of an OCP3 protein or fragment thereof in a plant, plant part and/or plant cell in comparison to wild type plants, wild type plant parts and/or wild type plant cells. Furthermore, the invention relates to transgenic plants, plant parts, and/or plant cells having an increased resistance against fungal pathogens, in particular, pathogens of the family Phacopsoraceae, and to recombinant expression vectors comprising a sequence that is identical or homologous to a sequence encoding an OCP3 protein.

Figure 1:
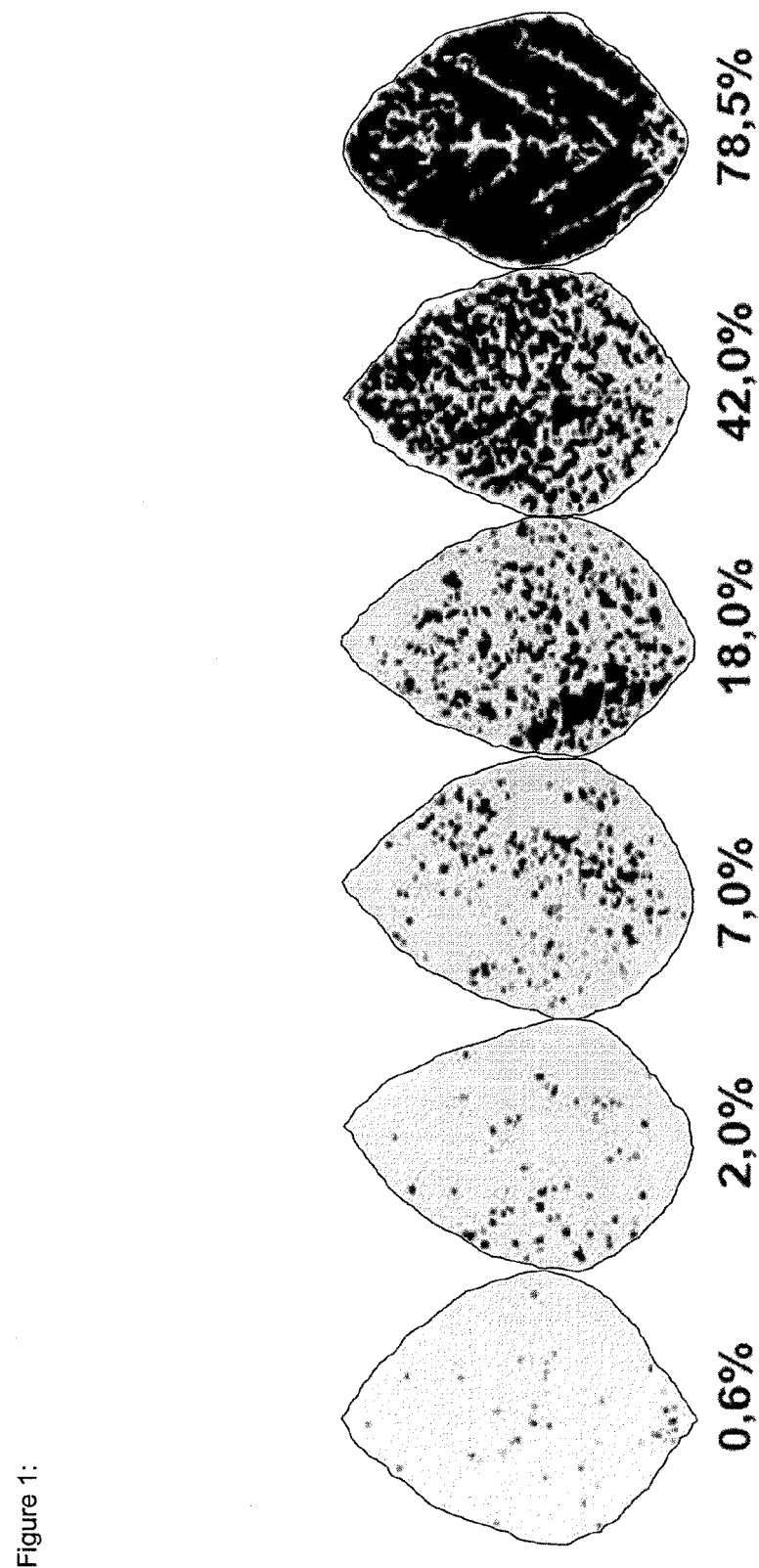

24 Claims, 7 Drawing Sheets
Specification includes a Sequence Listing.

(56) References Cited

OTHER PUBLICATIONS

International Search Report, issued in PCT/EP2013/055319, dated May 29, 2013.
Neu et al., "Cytological and Molecular Analysis of the *Hordeum vulgare-Puccinia triticina* Nonhost Interaction," MPMI, vol. 16, No. 7, (2003), pp. 626-633.
Ramírez et al., "Drought Tolerance in *Arabidopsis* is Controlled by the OCP3 Disease Resistance Regulator," The Plant Journal, vol. 58, (2009), pp. 578-591.
Ramírez et al., "OCP3 is an Important Modulator of NPR1-Mediated Jasmonic Acid-Dependent Induced Defenses in *Arabidopsis*," BMC Plant Biology, vol. 10, (2010), pp. 199-212.
Rytter, "Additional Alternative Hosts of *Phakopsora pachyrhizi*, Causal Agent of Soybean Rust," Plant Disease, vol. 68, No. 9, pp. 818-819.
Soybean Rust Workshop, eds. Sinclair and Hartman, (Aug. 9-11, 1995), pp. 1-11.
Williams, "Plant Homeobox Genes: Many Functions Stem from a Common Motif," BioEssays, vol. 20, No. 4, (1998), pp. 280-282.
Mukherjee et al., "A Comprehensive Classification and Evolutionary Analysis of Plant Homeobox Genes," Molecular Biology and Evolution, vol. 26, No. 12, (2009), pp. 2775-2794.

\* cited by examiner

Figure 3:

```
   1 ATGATTAAGG CTATGGCCCT TAGCTCAGCT GGTGTTGTTA GTCACCTTCA
  51 CCCCCCTAGT TTTAGTTCTA GTTCAGGCCT TAGTGTTAAT AGGGTGCTCT
 101 TTAGGAACCG TAACGCTAGT CCTTGCGGAC TTAGTTTGCC TATTCTTAAC
 151 CCTAGTAGAT CAGTGCTTGT GTTCGCTAGA GGTAAGAATA GGAAGGGCTT
 201 CGTTAGTTCT AGCTCTAGTA GCCCTAAGAA GAACAAGAAG AAGTCACTTG
 251 ACGGCGCTGA TAACGGTGGT GGTGAAGAAG AAGAGGATCC TTTCGAGGCT
 301 CTTTTTAACC TTCTCGAAGA GGACCTTAAG AACGATAACT CAGACGACGA
 351 AGAGATTAGC GAAGAAGAAC TTGAAGCTCT TGCTGACGAA CTTGCTAGGG
 401 CTCTTGGAGT TGGTGACGAC GTTGACGATA TTGATCTTTT CGGATCAGTG
 451 ACTGGTGACG TTGACGTGGA CGTTGATAAC GACGACGACG ATAACGACGA
 501 CGACGATAAC GACGACGACG ACGACGATTC AGAAGAGGAC GAAAGACCTA
 551 CTAAGCTTAA GAACTGGCAG CTTAAGAGGC TTGCTTACGC TCTTAAGGCT
 601 GGTAGACGTA AGACTAGTAT TAAGAACCTT GCTGCTGAGG TGTGCCTTGA
 651 TAGAGCTTAC GTTTTGGAGC TTCTTAGAGA TCCACCACCT AAGCTTTTGA
 701 TGCTTAGTGC TACTCTTCCA GACGAAAAGC CACCAGTTGC TGCTCCAGAA
 751 AACTCTAGTC CAGATCCTAG TCCAGTTGAG TCACTTAGTG CTGAGGACGT
 801 TGTGGTTGAA CCTAAAGAAA AGGTTAAGGA CGAGGCTGTT CACGTTATGC
 851 AACAAAGGTG GTCAGCTCAA AAGAGGGTTA AGAAGGCTCA CATTGAGACT
 901 CTCGAGAAGG TTTACCGTAG ATCTAAGAGG CCTACTAACG CTGTTGTTAG
 951 CTCTATCGTT CAAGTGACTA ACCTCCCTAG AAAGCGTGTT CTTAAGTGGT
1001 TCGAAGATAA GAGGGCTGAG GACGGTGTTC CAGATAAGAG AGCACCTTAT
1051 CAGGCCCCAG TTTAA
```

Figure 4:

```
MIKAMALSSAGVVSHLHPPSFSSSSGLSVNRVLFRNRNASPCGLSLPILN  50
PSRSVLVFARGKNRKGFVSSSSSPKKNKKKSLDGADNGGGEEEEDPFEA  100
LFNLLEEDLKNDNSDDEEISEEELEALADELARALGVGDDVDDIDLFGSV  150
TGDVDVDVDNDDDDNDDDDNDDDDDDSEEDERPTKLKNWQLKRLAYALKA  200
GRRKTSIKNLAAEVCLDRAYVLELLRDPPPKLLMLSATLPDEKPPVAAPE  250
NSSPDPSPVESLSAEDVVVEPKEKVKDEAVHVMQQRWSAQKRVKKAHIET  300
LEKVYRRSKRPTNAVVSSIVQVTNLPRKRVLKWFEDKRAEDGVPDKRAPY  350
QAPV*
```

Figure 5:

```
   1 CCTCTCAATC AAGGCCTTTA TTTGTTCTGC ACAATTTAAA ATAAAATAAC
  51 AAGAATTTTG TTGCTCTAAA ATCTCATTGC TCCCTATCTT GGAACATTGC
 101 GAGTGCGACA ACAAGGCAAC CCTAAAGATG ATAATGTGCA CCTCACTTGT
 151 GGCGTCGACA ACTGTATGGT GCGACGATAG AGCGGATGAT GAAGCAGAAG
 201 ATGGTGCCAA TTAACATCAA CTTCGATAGG CACGGAGGAC ACCAGCGGGG
 251 TCGAGCTAGG TAGCGGGTGG TGGTAGGAGA AAGGGTCGGT GAGTTGGGCT
 301 TGGAAGGGAA GGGATAGGAA CGAGTGAACA ATGTTTTTTA TTTTCTTATA
 351 AAAATATATT CTAGTGCATT AATTACAAGA TATTCATATC TAACGTATCA
 401 TATGTTTCTC ACGGTGGGAA ATTTGATGAG CTTTCCCATC CTAGAATCAA
 451 TCATCTTTTT ATATGTAGTT TGTGGGATTA TGGATGTAGC TGTCTTGGAA
 501 AAACATTAAA CTTTAAACAC ACCACGAGAA ACTCGTAAGA CATTCGTTGG
 551 GGATTACTTG TGATAACATG ATCCAGAAAC AGAACAAGAG TTTCAATGAA
 601 TCTAAATATT TCGAATTGAA GCATTTGACT GTTAAACATG TCATTTTAGG
 651 TTGCTATAGT TGTGGGAGAT ATAAGGTTAA TCTAATGGTT GGGGAAGAGA
 701 GGGGGAGGGG GAGACAAACT AATGAGGCAT ATAGCAACGC GCGCCGGGAG
 751 GAGTATGCCA GAATCAACAA TGAAACGACA TATAATGACT TAATAATCAG
 801 ATTCAAACCA TTTTTTTTTA TAAAATTTTT GCTAAAGGCT ACTCCAATAG
 851 TTACAGTACG CATAGGACGA ATGGTATTTG CGAGCATATT ATTTGAAAGT
 901 ATCATGAAAA ATGTGGTGTT GTTGAAAGGT CTACGGTGCA TTCCATTGAC
 951 AAAGTCAATT ACTCGTTCGT GGTTAATTTT GCTGAAAAGA TAAGCTCTAT
1001 GGATAAACTC AACTGAGTTG CTTGTTTATT TTTACGTCTT GCAAACAAA
1051 AGTATTAAAA CGACATGATA AACTCACAAG ACTACAATGT TGCTCTATAA
1101 GAAGAAGAAT TCAATAGAA ACGTTTCAGA TTAAAGCATT TGACTAGTAG
1151 ACATGTCGTC ATCAAGGTGT TGAATACATT GATGCAATTT TCATGTTAAT
1201 TGAAGGAAAA TAATAATGTA ACTAAACCAG TTTTAGAATA ATTGAAAGAA
1251 TCGCTGAAGA TTACACCAGT AGTTAGTTGT TGAGTTATTG TACACTTTGC
1301 ATGGGCGAA TGGTATTTAT TTGCATGGGG TTGTTGAAGA CAACAATATT
1351 GGTTGGTGGT TGAGCACTCA GCACGGGCTT TGCCTGAAAC TTTAATGTTT
1401 CCCCATTCTT CCCGTGAACG TTCAGAATCC AGATCCATTG ATTCTCATTA
1451 CATTACGATT TCGCGTCAAA AGTAGAAACT AAAAACAAAA ATAGAGAAAA
1501 GGAGAACACT TGCCACCTCA TCCAACAGCT GCTTATTTAA TCTCTACACT
1551 TGCTCGTAGG GTCTCAATTC GAGGTCGCAG ATTAGATTCC CAATTCTCCG
1601 TTCGCCATCT GTTAAGGTAA GCTTTTCTTC TTAAACTATT GTACTTTCCA
1651 GTTCATGCAT AATAGTATCA GGAAACAAAA AAAAAAAGTA TAAGATAAGA
1701 TCATTGATGT GATGTGTTGT GTAGCGTAGG AGATAGAGAG GGAGAGATTG
1751 AAA
```

Figure 7:

| SEQ ID NO: | Description of the sequence listing |
|---|---|
| 1 | Nucleotide sequence; full-length-sequence of the OCP3 gene; Arabidopsis thaliana |
| 2 | Amino acid sequence; OCP3 protein; Arabidopsis thaliana |
| 3 | Nucleotide sequence; sequence of the GmEpidermis-specific promotor 670 (derived from Glyma02g47670); Glycine max |
| 4 | Nucleotide sequence OCP3, variant 1 |
| 5 | Nucleotide sequence OCP3, variant 2 |
| 6 | Nucleotide sequence OCP3, variant 3 |
| 7 | Nucleotide sequence OCP3, variant 4 |
| 8 | Nucleotide sequence OCP3, variant 5 |
| 9 | Nucleotide sequence OCP3, variant 6 |
| 10 | Nucleotide sequence OCP3, variant 7 |
| 11 | Nucleotide sequence OCP3, variant 8 |
| 12 | Nucleotide sequence OCP3, variant 9 |
| 13 | Amino acid sequence OCP3, variant 9 |
| 14 | Nucleotide sequence OCP3, variant 10 |
| 15 | Amino acid sequence OCP3, variant 10 |
| 16 | Nucleotide sequence OCP3, variant 11 |
| 17 | Amino acid sequence OCP3, variant 11 |
| 18 | Nucleotide sequence OCP3, variant 12 |
| 19 | Amino acid sequence OCP3, variant 12 |
| 20 | Nucleotide sequence OCP3, variant 13 |
| 21 | Amino acid sequence OCP3, variant 13 |

Figure 7 continued:

| 22 | Nucleotide sequence OCP3, variant 14 |
|----|--------------------------------------|
| 23 | Amino acid sequence OCP3, variant 14 |
| 24 | Nucleotide sequence OCP3, variant 15 |
| 25 | Amino acid sequence OCP3, variant 15 |
| 26 | Nucleotide sequence OCP3, variant 16 |
| 27 | Amino acid sequence OCP3, variant 16 |

SEQUENCE LISTING

```
<160> NUMBER OF SEQ ID NOS: 27

<210> SEQ ID NO 1
<211> LENGTH: 1065
<212> TYPE: DNA
<213> ORGANISM: Arabidopsis thaliana

<400> SEQUENCE: 1
atgattaagg ctatggccct tagctcagct ggtgttgtta gtcaccttca ccccccctagt      60 tttagttcta gttcaggcct tagtgttaat agggtgctct ttaggaaccg taacgctagt     120
ccttgcggac ttagtttgcc tattcttaac cctagtagat cagtgcttgt gttcgctaga     180
```

-continued

```
ggtaagaata ggaagggctt cgttagttct agctctagta gccctaagaa gaacaagaag    240
aagtcacttg acggcgctga taacggtggt ggtgaagaag aagaggatcc tttcgaggct    300 cttttaacc ttctcgaaga ggaccttaag aacgataact cagacgacga agagattagc    360
gaagaagaac ttgaagctct tgctgacgaa cttgctaggg ctcttggagt tggtgacgac    420
gttgacgata ttgatctttt cggatcagtg actggtgacg ttgacgtgga cgttgataac    480
gacgacgacg ataacgacga cgacgataac gacgacgacg acgacgattc agaagaggac    540
gaaagaccta ctaagcttaa gaactggcag cttaagaggc ttgcttacgc tcttaaggct    600
ggtagacgta agactagtat taagaacctt gctgctgagg tgtgccttga tagagcttac    660
gttttggagc ttcttagaga tccaccacct aagcttttga tgcttagtgc tactcttcca    720
gacgaaaagc caccagttgc tgctccagaa aactctagtc cagatcctag tccagttgag    780
tcacttagtg ctgaggacgt tgtggttgaa cctaaagaaa aggttaagga cgaggctgtt    840
cacgttatgc aacaaggtg gtcagctcaa aagagggtta agaaggctca cattgagact    900
ctcgagaagg tttaccgtag atctaagagg cctactaacg ctgttgttag ctctatcgtt    960
caagtgacta acctccctag aaagcgtgtt cttaagtggt tcgaagataa gagggctgag   1020
gacggtgttc agataagag agcaccttat caggccccag tttaa                    1065
```

<210> SEQ ID NO 2
<211> LENGTH: 354
<212> TYPE: PRT
<213> ORGANISM: Arabidopsis thaliana

<400> SEQUENCE: 2

```
Met Ile Lys Ala Met Ala Leu Ser Ser Ala Gly Val Val Ser His Leu
1               5                   10                  15

His Pro Pro Ser Phe Ser Ser Ser Gly Leu Ser Val Asn Arg Val
            20                  25                  30

Leu Phe Arg Asn Arg Asn Ala Ser Pro Cys Gly Leu Ser Leu Pro Ile
        35                  40                  45

Leu Asn Pro Ser Arg Ser Val Leu Val Phe Ala Arg Gly Lys Asn Arg
    50                  55                  60

Lys Gly Phe Val Ser Ser Ser Ser Ser Pro Lys Lys Asn Lys Lys
65                  70                  75                  80

Lys Ser Leu Asp Gly Ala Asp Asn Gly Gly Glu Glu Glu Asp
                85                  90                  95

Pro Phe Glu Ala Leu Phe Asn Leu Leu Glu Glu Asp Leu Lys Asn Asp
            100                 105                 110

Asn Ser Asp Asp Glu Glu Ile Ser Glu Glu Leu Glu Ala Leu Ala
        115                 120                 125

Asp Glu Leu Ala Arg Ala Leu Gly Val Gly Asp Val Asp Asp Ile
    130                 135                 140

Asp Leu Phe Gly Ser Val Thr Gly Asp Val Asp Val Asp Asn
145                 150                 155                 160

Asp Asp Asp Asp Asn Asp Asp Asp Asn Asp Asp Asp Asp
                165                 170                 175

Ser Glu Glu Asp Glu Arg Pro Thr Lys Leu Lys Asn Trp Gln Leu Lys
            180                 185                 190

Arg Leu Ala Tyr Ala Leu Lys Ala Gly Arg Arg Lys Thr Ser Ile Lys
        195                 200                 205

Asn Leu Ala Ala Glu Val Cys Leu Asp Arg Ala Tyr Val Leu Glu Leu
    210                 215                 220
```

```
Leu Arg Asp Pro Pro Lys Leu Leu Met Leu Ser Ala Thr Leu Pro
225                 230                 235                 240

Asp Glu Lys Pro Pro Val Ala Ala Pro Glu Asn Ser Ser Pro Asp Pro
            245                 250                 255

Ser Pro Val Glu Ser Leu Ser Ala Glu Asp Val Val Val Glu Pro Lys
            260                 265                 270

Glu Lys Val Lys Asp Glu Ala Val His Val Met Gln Gln Arg Trp Ser
        275                 280                 285

Ala Gln Lys Arg Val Lys Lys Ala His Ile Glu Thr Leu Glu Lys Val
    290                 295                 300

Tyr Arg Arg Ser Lys Arg Pro Thr Asn Ala Val Ser Ser Ile Val
305                 310                 315                 320

Gln Val Thr Asn Leu Pro Arg Lys Arg Val Leu Lys Trp Phe Glu Asp
                325                 330                 335

Lys Arg Ala Glu Asp Gly Val Pro Asp Lys Arg Ala Pro Tyr Gln Ala
            340                 345                 350

Pro Val
```

<210> SEQ ID NO 3
<211> LENGTH: 1753
<212> TYPE: DNA
<213> ORGANISM: Glycine max

<400> SEQUENCE: 3

```
cctctcaatc aaggccttta tttgttctgc acaatttaaa ataaaataac aagaattttg    60
ttgctctaaa atctcattgc tccctatctt ggaacattgc gagtgcgaca acaaggcaac   120
cctaaagatg ataatgtgca cctcacttgt ggcgtcgaca actgtatggt gcgacgatag   180
agcggatgat gaagcagaag atggtgccaa ttaacatcaa cttcgatagg cacggaggac   240
accagcgggg tcgagctagg tagcgggtgg tggtaggaga aagggtcggt gagttgggct   300
tggaagggaa gggataggaa cgagtgaaca atgttttta tttcttata aaatatatt     360
ctagtgcatt aattacaaga tattcatatc taacgtatca tatgtttctc acggtgggaa   420
atttgatgag cttctccatc ctagaatcaa tcatcttttt atatgtagtt tgtgggatta   480
tggatgtagc tgtcttggaa aaacattaaa ctttaaacac accacgagaa actcgtaaga   540
cattcgttgg ggattacttg tgataacatg atccagaaac agaacaagag tttcaatgaa   600
tctaaatatt tcgaattgaa gcatttgact gttaaacatg tcattttagg ttgctatagt   660
tgtgggagat ataaggttaa tctaatggtt ggggaagaga gggggagggg gagacaaact   720
aatgaggcat atagcaacgc gcgccgggag gagtatgcca gaatcaacaa tgaaacgaca   780
tataatgact aataatcag attcaaacca tttttttta taaaatttt gctaaaggct      840
actccaatag ttacagtacg cataggacga atggtatttg cgagcatatt atttgaaagt   900
atcatgaaaa atgtggtgtt gttgaaaggt ctacggtgca ttccattgac aaagtcaatt   960
actcgttcgt ggttaatttt gctgaaaaga taagctctat ggataaactc aactgagttg  1020
cttgtttatt tttacgtctt gcaaaacaaa agtattaaaa cgacatgata aactcacaag  1080
actacaatgt tgctctataa gaagaagaat ttcaatagaa acgtttcaga ttaaagcatt  1140
tgactagtag acatgtcgtc atcaaggtgt tgaatacatt gatgcaattt tcatgttaat  1200
tgaaggaaaa taataatgta actaaaccag ttttagaata attgaaagaa tcgctgaaga  1260
ttacaccagt agttagttgt tgagttattg tacactttgc atggggcgaa tggtatttat  1320
```

```
ttgcatgggg ttgttgaaga caacaatatt ggttggtggt tgagcactca gcacgggctt    1380
tgcctgaaac tttaatgttt ccccattctt cccgtgaacg ttcagaatcc agatccattg    1440
attctcatta cattacgatt tcgcgtcaaa agtagaaact aaaaacaaaa atagagaaaa    1500
ggagaacact tgccacctca tccaacagct gcttatttaa tctctacact tgctcgtagg    1560
gtctcaattc gaggtcgcag attagattcc caattctccg ttcgccatct gttaaggtaa    1620
gcttttcttc ttaaactatt gtactttcca gttcatgcat aatagtatca ggaaacaaaa    1680 aaaaaagta taagataaga tcattgatgt gatgtgttgt gtagcgtagg agatagagag     1740
ggagagattg aaa                                                      1753

<210> SEQ ID NO 4
<211> LENGTH: 1065
<212> TYPE: DNA
<213> ORGANISM: Artificial sequence
<220> FEATURE:
<223> OTHER INFORMATION: Sequence variant 1

<400> SEQUENCE: 4
atgatcaaag ctatggcttt gtctagtgcc ggcgttgtgt cgcatctaca tcctccatcc      60
ttcagctcat ctagcgggct atcggtaaat agagtattga tccgcaatcg aaatgcctct    120
ccctgtggcc tgtccatgcc aatcctaaat ccctcgcgct cggtactggt atttgccagg    180
ggaaagaacc gtaaagggtt tgtttcgtca tcttctagtt cgcccaaaaa aaataaaaaa    240
aaaagtttag atggagctga caatggcggc ggggaggagg aggaagaccc atttgaagca    300
ctattcaatc tcctggagga agatttaaaa aatgataatt cggacgatga ggaaatctcg    360
gaggaggagt tggaggccct ggcagatgag ctcgcaagag cgctagggg aggagatgat     420 gtcgatgaca tagatttgtt tgggtccgtc accggcgatg tagacgttga tgtcgacaat    480
gatgatgatg acaatgatga tgacgacaat gatgatgatg atgatgactc cgaggaagat    540
gagaggccga cgaaattaaa aaattggcaa ctaaaacgct tagcgtatgc attgaaagca    600
gggcgacgca aaacctccat aaaaaattta gcagcagagg tctgtttaga cagggcatat    660
gttatggaac tgctccgcga cccgcccccc aaactgatga tgctgagcgc gactctcccg    720
gatgagaaac ctcctgtagc ggcacctgag aattcttccc cggacccgag cccggtagag    780
tccctatccg ccgaagatgt cgttgttgag cctaaggaaa aagtgaaaga tgaagcggtt    840
cacgtgatgc aacagagatg gtccgcgcag aaacgtgtca agaaagccca tatcgaaacc    900
ctagaaaaag tatataggag gagcaaacga cccaccaatg cggtcgtaag tagcatagtt    960
caggttacca atcttcctcg aaagcgggtc ctcaaatggt ttgaggacaa agagccgaa    1020 gatggagtcc ctgacaaacg agctccgtac caagcgcctg tgtag                   1065

<210> SEQ ID NO 5
<211> LENGTH: 1065
<212> TYPE: DNA
<213> ORGANISM: Artificial sequence
<220> FEATURE:
<223> OTHER INFORMATION: Sequence variant 2

<400> SEQUENCE: 5
atgatcaagg ccatggccct gtcctcagcg ggcgtggtca gccatttaca tccaccgtcg     60
ttttcgagca gctcggggct cagcgttaac cgtgtcctct ttcgtaaccg aaatgcttct    120
ccatgtggat tgagcatgcc catcctgaat ccgtccagaa gcgtactggt cttttgcacgc   180 gggaaaaaca gaaaagggtt cgtaagctcc agttctagtt ccccgaagaa aaacaagaaa    240
```

| | | | | |
|---|---|---|---|---|
| aaaagtctag | atggggcgga | caatggcgga | ggagaggagg | aggaagaccc | cttcgaggcg | 300 |
| cttttaatc | ttttggagga | agatttaaaa | aacgacaatt | cggatgatga | agaaatatcg | 360 |
| gaggaggagc | tagaggccct | tgcggatgag | ttggctcgag | cactgggagt | cggggatgat | 420 |
| gtcgatgaca | tagacctttt | tgggtcagtt | acgggtgatg | tcgacgttga | tgtagataat | 480 |
| gatgatgatg | ataatgatga | tgatgacaat | gatgatgatg | atgatgactc | cgaggaggat | 540 |
| gagcgaccta | ctaaactcaa | aaattggcag | ttgaaacgac | tcgcctatgc | tctaaaggct | 600 |
| ggtaggcgca | aaccagtat | taaaaatctc | gctgctgaag | tctgccttga | ccgagcatat | 660 |
| gtcatggaat | tgttgcgtga | tcctcccccct | aaactgttga | tgcttagtgc | aactctcccg | 720 |
| gatgagaaac | ctccagttgc | tgcgcccgag | aattcgagcc | ccgacccctc | acccgtagaa | 780 |
| tcactttctg | ccgaagatgt | tgttgttgag | ccaaaggaga | aggtgaaaga | cgaggccgta | 840 |
| catgttatgc | agcagaggtg | gtcggctcaa | aaacgtgtga | agaaggcaca | tatagaaacg | 900 |
| ctcgaaaaag | tttatcgccg | ctctaaacgt | cccacgaacg | cagtcgtatc | ctctatagtc | 960 |
| caggttacca | atctaccaag | aaaacggtg | ttaaaatggt | ttgaggacaa | acgtgcagag | 1020 |
| gatggtgtcc | ccgataaaag | agcgccgtat | caagcgcccg | tttag | 1065 |

<210> SEQ ID NO 6
<211> LENGTH: 1065
<212> TYPE: DNA
<213> ORGANISM: Artificial sequence
<220> FEATURE:
<223> OTHER INFORMATION: Sequence variant 3

<400> SEQUENCE: 6

| | | | | |
|---|---|---|---|---|
| atgattaagg | ctatggctct | ttcttcagct | ggcgtggtga | gtcatcttca | tccaccctca | 60 |
| ttttcaagca | gttcagggct | gagtgtgaat | agggtactct | tccgtaaccg | caacgcatct | 120 |
| ccctgcggtc | tttccatgcc | tattctaaac | cccagtagat | ctgtgcttgt | gtttgcgcgt | 180 |
| ggaaagaata | ggaaaggctt | tgtttcttcg | agttctagta | gcccaaagaa | gaataagaaa | 240 |
| aaatcacttg | atggtgcaga | taatggcgga | ggagaagagg | aggaagatcc | gttcgaggcc | 300 |
| cttttcaact | tgctggagga | agatctcaaa | aatgataact | cagatgatga | agaaatctca | 360 |
| gaggaagagc | tagaggcgct | tgctgatgag | ctggccaggg | ctcttggagt | tggtgatgac | 420 |
| gtcgacgata | tcgatctatt | cggatcggtg | acgggtgacg | tagatgttga | cgtcgataac | 480 |
| gacgacgatg | ataatgatga | tgatgataat | gatgatgatg | atgacgactc | tgaggaggat | 540 |
| gaaaggccaa | ccaagcttaa | aaattggcaa | cttaagaggt | tggcgtatgc | actaaaagcc | 600 |
| ggacgccgca | aaacttccat | caagaacctc | gccgccgagg | tgtgtcttga | cagggcgtac | 660 |
| gtattggaac | ttttaagaga | cccaccacct | aagctcatga | tgctttccgc | aactttaccc | 720 |
| gatgagaagc | ctcctgttgc | agcgcccgaa | aactcatcgc | ccgacccttc | cccagtggag | 780 |
| agtcttagtg | ccgaggatgt | cgtagtagag | ccgaaagaaa | aagtaaaaga | tgaggctgtg | 840 |
| catgttatgc | agcagcgatg | gtccgcgcag | aaacgggtaa | agaaggcgca | tatcgagact | 900 |
| cttgagaaag | tgtaccgaag | atcaaaaagg | ccgactaatg | cggtagtcag | ttcaatagtg | 960 |
| caagtcacta | atctccccag | aaaacgtgtt | ctaaatggt | ttgaggacaa | aagagccgaa | 1020 |
| gatggtgtgc | cggataaaag | ggccccctac | caggctccag | tttag | 1065 |

<210> SEQ ID NO 7
<211> LENGTH: 1065
<212> TYPE: DNA

<213> ORGANISM: Artificial sequence
<220> FEATURE:
<223> OTHER INFORMATION: Sequence variant 4

<400> SEQUENCE: 7

```
atgattaagg ctatggccct tagcagcgcg ggtgtagttt cacaccttca tcctcctagc      60
ttctcatcta gttccggcct gtcggttaat agggtgttgt ttcgaaaccg taacgctagt     120
ccatgcggat taagtttgcc tatattaaat ccttcgcgtt cagtattagt ttttgccaga     180
ggtaagaacc gtaaaggctt cgttagtagt tcgtcgagtt ccccaaaaaa aaataaaaaa     240
aaaagtttag atggcgcgga caatggtggt ggtgaagagg aggaagaccc atttgaagct     300
cttttttaacc ttttggaaga ggatcttaag aatgacaatt cagacgatga ggaaatctct     360
gaagaagaac tagaggcttt ggctgatgag cttgctaggg cgcttggcgt aggtgacgat     420
gttgacgata ttgatctttt tggatcggtg actggtgatg ttgatgtgga cgtcgataac     480
gatgacgacg acaacgacga cgacgacaac gacgacgatg atgacgatag tgaggaagat     540
gaaagaccta ccaagttaaa aaattggcag ttaaagaggc ttgcgtatgc ccttaaagct     600
gggcgtagaa aaacttccat aaagaacctt gctgctgagg tgtgtcttga cagagcctat     660
gttttggaac ttcttcgaga tccaccaccc aagcttttga tgctttcagc tactctgcct     720
gatgaaaagc caccagttgc ggctccggaa actctagtc cagatcccag tccagttgaa     780
tccctttctg ccgaggacgt tgtggttgag cccaaagaga aagttaagga tgaagctgtg     840
cacgttatgc agcagcgctg gtcagctcaa aaaagagtta agaaggctca tattgagacg     900
ctcgaaaaag tttatcgtag atctaagagg ccaacgaacg cggtggtctc atctatcgtt     960
caagtgacta atttaccgcg aaaaaggggtt ttgaagtggt ttgaagataa gagggctgaa    1020
gatggtgttc ctgacaaacg ggccccgtac caagccccag tttaa                    1065
```

<210> SEQ ID NO 8
<211> LENGTH: 1065
<212> TYPE: DNA
<213> ORGANISM: Artificial sequence
<220> FEATURE:
<223> OTHER INFORMATION: Sequence variant 5

<400> SEQUENCE: 8

```
atgattaaag cgatggccct tagctctgca ggtgttgtta gtcaccttca ccccctagt       60
ttcagtagca gtagcggctt gagcgttaac agggtgttat ttcggaatcg taacgctagt     120
ccttgcggac tttctttgcc tattcttaac cctagtagat cagtgttagt gttcgctagg     180
ggtaagaaca ggaaaggctt tgtgtcatct agcagcagta gccctaagaa aaacaagaaa     240
aaatcccttg acggcgctga taacggtggc ggtgaagagg aggaagatcc tttcgaggct     300
cttttcaatc ttctcgaaga ggaccttaag aacgataatt cagacgatga agaaatttcg     360
gaagaagaac ttgaggctct tgctgacgaa cttgctaggg ctcttggcgt cggtgacgac     420
gttgacgata tagatttatt cggatcggtg actggtgatg tcgatgtaga cgttgacaac     480
gatgatgatg ataacgacga tgacgataat gacgacgatg acgacgattc agaagaagat     540
gagcgtccta ctaaacttaa gaactggcag cttaaaaggc ttgcttatgc tttgaaggct     600
ggtcgaagaa aaacgagtat caagaacctt gctgctgaag tgtgccttga tagagcttat     660
gttttggaac tttaagaga cccaccgcct aagcttatga tgcttagtgc tactttgcca     720
gacgaaaaac cgccggtagc tgctccagag aattctagtc ctgatcctag tccagtcgaa     780
tcactatctg cggaagatgt tgtggttgag cctaaagaaa aggttaagga tgaggctgtt     840
```

```
cacgttatgc aacaaaggtg gtctgctcag aagcgggtta aaaaggcgca cattgagact    900
ctcgagaaag tttatcgtag atctaagagg cctactaatg ctgttgttag ctctatcgtc    960
caagtgacga atctccctag aaaacgtgtg cttaagtggt tcgaagataa agggctgag    1020 gacggtgtcc cagataagcg cgcaccttac caggccccag tataa                   1065
```

<210> SEQ ID NO 9
<211> LENGTH: 1065
<212> TYPE: DNA
<213> ORGANISM: Artificial sequence
<220> FEATURE:
<223> OTHER INFORMATION: Sequence variant 6

<400> SEQUENCE: 9

```
atgattaagg ccatggccct ttcatcagct ggtgttgtta gtcatcttca cccgcctagc     60
tttagttcta gttcaggcct tagtgttaat agggtactat tcaggaacag gaatgctagt    120
ccttgtgggc ttagtttgcc gattcttaac cctagtcgtt cagtgcttgt attcgctaga    180
ggtaaaaata ggaagggctt tgttagttct agctctagtt ccccgaagaa gaacaagaag    240
aaatcacttg acggcgccga taatggtggt ggtgaggagg aagaggatcc ttttgaggct    300
ttgtttaacc ttctcgaaga agaccttaag aacgataact cagatgacga agagattagc    360
gaagaagaac ttgaagctct tgctgacgaa cttgccaggg ctcttggagt cggtgatgat    420
gttgacgata ttgatctttt tggatcagtg actggtgatg tggacgtgga cgtagataac    480
gacgatgacg ataacgacga cgacgataac gatgacgatg atgacgattc agaagaagat    540
gagagaccta ctaagcttaa aaactggcag cttaagcggc ttgcttacgc gttaaaagct    600
ggtagacgta aaactagtat taagaatctt gctgctgagg tgtgtcttga tagagcttat    660
gtgttggagc ttcttcggga tccaccaccc aaacttatga tgcttagtgc tactcttcca    720
gacgaaaaac ctccagttgc tgctccggaa aactcgtcgc cagatcctag tccagttgag    780
tcacttagtg ctgaagacgt tgtggttgaa cccaaagaaa aggttaaaga cgaggctgtg    840
cacgtaatgc aacagaggtg gtcagctcaa aaaagggtga agaaagctca cattgagact    900
ctcgagaagg tctaccgtcg ttctaaaagg cctacaaacg ctgtggttag ctctatcgtt    960
caagttacaa acctccctag aaagcgtgtt ctaaagtggt tcgaggataa aagggctgag   1020
gacggtgtgc cagataagag agcaccttac caggcacctg tctaa                   1065
```

<210> SEQ ID NO 10
<211> LENGTH: 1065
<212> TYPE: DNA
<213> ORGANISM: Artificial sequence
<220> FEATURE:
<223> OTHER INFORMATION: Sequence variant 7

<400> SEQUENCE: 10

```
atgatcaagg caatggccct ttcgtcagct ggtgttgtta gtcaccttca cctcctagt      60 ttttcctcta gtagcggcct tagtgtgaat agggtgctct ttaggaaccg taacgctagt    120
ccttgtggac taagtttgcc tatccttaac cctagtagat cagtgttagt gttcgctaga    180
ggtaagaata gaagggctt cgttagttct agcagcagta gccctaagaa gaacaagaaa     240
aagtcattgg acggcgctga taacggtggt ggtgaagaag aagaggatcc tttcgaggct    300
ttgtttaacc ttctcgagga ggacctgaag aacgacaact cagacgacga ggagatttcc    360
gaagaagaac ttgaagcgtt ggctgacgag cttgcaaggg ctcttggagt tggtgatgac    420
```

| | |
|---|---|
| gttgacgata ttgatctttt cggttcagtg actggtgacg ttgacgtgga cgttgataac | 480 |
| gatgacgacg acaacgatga cgacgataac gacgacgacg acgacgattc agaagaggac | 540 |
| gaaagaccta ctaagcttaa aaactggcag cttaagaggt tagcttacgc tcttaaggct | 600 |
| ggaagacgta agactagtat taagaacctt gctgctgagg tgtgtcttga tagagcctac | 660 |
| gttttggagc ttcttagaga tccaccacct aagcttttga tgcttagtgc cactcttcca | 720 |
| gacgaaaagc caccagttgc tgctccagaa aactctagtc cagatcctag tccggttgag | 780 |
| tcactttcgg ctgaggacgt tgtggttgag ccaaaagaaa aggttaagga cgaggctgtt | 840 |
| catgtcatgc aacaaggtg tcagcccaa aaagggtta agaaagctca catcgagacc | 900 |
| ttagagaagg tttaccgtag atctaagagg cctactaacg ctgttgttag ctctatcgtt | 960 |
| caagtaacta acctccctag aaaacgtgtt cttaagtggt tcgaagataa aagggctgaa | 1020 |
| gacggtgttc cagataagag agcaccctat caggcccccg tttaa | 1065 |

<210> SEQ ID NO 11
<211> LENGTH: 1065
<212> TYPE: DNA
<213> ORGANISM: Artificial sequence
<220> FEATURE:
<223> OTHER INFORMATION: Sequence variant 8

<400> SEQUENCE: 11

| | |
|---|---|
| atgattaagg ctatggccct tagctcagct ggtgttgtga gtcatcttca cccccctagt | 60 |
| tttagttcta gttcaggcct tagtgttaat agggttctct ttaggaaccg taatgctagt | 120 |
| ccttgcggac ttagttttgcc tattcttaac cctagtagat cagtgcttgt gttcgccagg | 180 |
| ggtaagaatc gaaaaggctt cgttagttct agctctagta gccctaagaa gaacaaaaag | 240 |
| aagtcacttg acggggctga taacggtggc ggtgaagaag aagaggatcc tttcgaggct | 300 |
| cttttcaatc ttctcgaaga ggaccttaag aacgataatt cagacgacga agagattagc | 360 |
| gaagaggaac ttgaagctct tgctgatgaa cttgctaggg ctcttggagt tggtgacgac | 420 |
| gttgacgata ttgatctttt cggaagtgtg actggtgacg ttgacgtgga cgttgataac | 480 |
| gatgacgacg ataacgacga cgacgataac gacgacgacg atgacgattc agaagaggat | 540 |
| gaaagaccta ctaagcttaa gaactggcag cttaagaggc tcgcttacgc tcttaaggct | 600 |
| ggtagacgta agactagtat taaaaacctt gctgctgagg tgtgccttga tagagcttac | 660 |
| gttttggagc ttttgagaga tccaccacct aagcttttga tgcttagtgc tactcttcca | 720 |
| gacgaaaagc caccagttgc tgctccagaa aactctagtc ctgatcctag tccagttgaa | 780 |
| tcacttagtg ctgaagacgt tgtggttgaa cctaaagaaa aggttaagga cgaggctgtt | 840 |
| cacgttatgc aacaaggtg tcagctcaa aagagggtta agaaggctca cattgagact | 900 |
| ctcgagaagg tttaccgtag atcaaagagg cctactaacg ctgttgttag ctctatcgtt | 960 |
| caagtgacta acctccccag aaagcgtgtt cttaaatggt tcgaagataa agggctgag | 1020 |
| gacggtgtac cagataagag agcaccttat caagccccag tctaa | 1065 |

<210> SEQ ID NO 12
<211> LENGTH: 1062
<212> TYPE: DNA
<213> ORGANISM: Artificial sequence
<220> FEATURE:
<223> OTHER INFORMATION: Nucleotide sequence OCP3, variant 9

<400> SEQUENCE: 12

| | |
|---|---|
| atggtgcacg ccatggccct gagcagcggc ctggccgtga cccacctgca ccccccctgc | 60 |

```
ttcagcagca ccagcggcat gaccgtgcag aaggtggtgt acagaaacag aaacggcagc      120
cccagcggca tgagcctgcc catcctgaac cccagcagaa gcggcggcat gtgggccaag      180
gccagacaga agaagggctt cgtgtgctgc acctgcagca gccccaagaa gaaccacaag      240
aagagcatgg acggcgccga caacatcggc gtggacgagg aggaggaccc cttcgaggcc      300
atctggcagg tgatggagga cgacgccaag aacgagcaga gcgacgacga ggaggccacc      360
gacgaggacg ccgagatcct ggccgaggag gcgccagag ccctgggcgt gggcgaggac       420
gtggaggagg gcgacctgtt cggcagcgtg accggcgagg tggacgtgga cgtggagaac      480
gaggaggagg acaacgagga cgaggacaac gaggacgagg acgacgacag cgaggacgac      540
gaccacccca cccacctgaa gcagttcaac atcaagaaga tggcctacat gctgcacgcc      600
ggcagaagaa agacctgcat caagaacggc gccgccgagg tgagcgccga gagactgttc      660
gtgatggacc tgatgagaga gcccccccc aagctgctga tgggcagcgc caccctgccc       720
gaggacaagc cccccctggc cgcccccgac cagagctgcc ccgaccccag ccccgtggag      780
agcctgtgca tcgaggacct ggtggtggag cccaaggaga aggtgaagga cgaggccgtg      840
cacgtgatgc agcagagatg gagcgcccag aagagagtga agaaggccca catcgagacc      900
ctggagaagg tgtacagaag aagcaagaga cccaccaacg ccgtggtgag cagcatcgtg      960
caggtgacca acctgcccag aaagagagtg ctgaagtggt tcgaggacaa gagagccgag     1020
gacggcgtgc ccgacaagag agcccctac caggtgcccg tg                         1062

<210> SEQ ID NO 13
<211> LENGTH: 354
<212> TYPE: PRT
<213> ORGANISM: Artificial sequence
<220> FEATURE:
<223> OTHER INFORMATION: Amino acid sequence OCP3, variant 9

<400> SEQUENCE: 13

Met Val His Ala Met Ala Leu Ser Ser Gly Leu Ala Val Thr His Leu
1               5                   10                  15

His Pro Pro Cys Phe Ser Ser Thr Ser Gly Met Thr Val Gln Lys Val
                20                  25                  30

Val Tyr Arg Asn Arg Asn Gly Ser Pro Ser Gly Met Ser Leu Pro Ile
            35                  40                  45

Leu Asn Pro Ser Arg Ser Gly Gly Met Trp Ala Lys Ala Arg Gln Lys
        50                  55                  60

Lys Gly Phe Val Cys Cys Thr Cys Ser Ser Pro Lys Lys Asn His Lys
65                  70                  75                  80

Lys Ser Met Asp Gly Ala Asp Asn Ile Gly Val Asp Glu Glu Glu Asp
                85                  90                  95

Pro Phe Glu Ala Ile Trp Gln Val Met Glu Asp Asp Ala Lys Asn Glu
                100                 105                 110

Gln Ser Asp Asp Glu Glu Ala Thr Asp Glu Asp Ala Glu Ile Leu Ala
            115                 120                 125

Glu Glu Gly Ala Arg Ala Leu Gly Val Gly Glu Asp Val Glu Glu Gly
        130                 135                 140

Asp Leu Phe Gly Ser Val Thr Gly Glu Val Asp Val Asp Val Glu Asn
145                 150                 155                 160

Glu Glu Glu Asp Asn Glu Asp Glu Asp Asn Glu Asp Glu Asp Asp Asp
                165                 170                 175

Ser Glu Asp Asp Asp His Pro Thr His Leu Lys Gln Phe Asn Ile Lys
```

```
            180                 185                 190
Lys Met Ala Tyr Met Leu His Ala Gly Arg Arg Lys Thr Cys Ile Lys
            195                 200                 205

Asn Gly Ala Ala Glu Val Ser Ala Glu Arg Leu Phe Val Met Asp Leu
            210                 215                 220

Met Arg Glu Pro Pro Lys Leu Leu Met Gly Ser Ala Thr Leu Pro
225                 230                 235                 240

Glu Asp Lys Pro Pro Leu Ala Ala Pro Asp Gln Ser Cys Pro Asp Pro
                245                 250                 255

Ser Pro Val Glu Ser Leu Cys Ile Glu Asp Leu Val Val Glu Pro Lys
            260                 265                 270

Glu Lys Val Lys Asp Glu Ala Val His Val Met Gln Gln Arg Trp Ser
            275                 280                 285

Ala Gln Lys Arg Val Lys Lys Ala His Ile Glu Thr Leu Glu Lys Val
            290                 295                 300

Tyr Arg Arg Ser Lys Arg Pro Thr Asn Ala Val Val Ser Ser Ile Val
305                 310                 315                 320

Gln Val Thr Asn Leu Pro Arg Lys Arg Val Leu Lys Trp Phe Glu Asp
                325                 330                 335

Lys Arg Ala Glu Asp Gly Val Pro Asp Lys Arg Ala Pro Tyr Gln Val
            340                 345                 350

Pro Val

<210> SEQ ID NO 14
<211> LENGTH: 1062
<212> TYPE: DNA
<213> ORGANISM: Artificial sequence
<220> FEATURE:
<223> OTHER INFORMATION: Nucleotide sequence OCP3, variant 10

<400> SEQUENCE: 14
atgatcaagg ccatggccat gagcagcgcc atggtgatga gccacatgaa gccccccagc      60
ttcaccacca gcagcggcct gagcgccaac agagtgctgt tccacaacaa gaacatcagc     120
cccaccggca tcagcctgcc cctgctgaac cccagccaca gcctgggcgt gtgggccaga     180
atgcacaacc acaagatgta cctgtgcagc agcagctgca cccccaagca acaacaagaag    240 cacagcctgg agatggccga gaacggcggc gtggaggagg acgaggaccc cttcgaggtg     300
ctgttcaacc tgctggagga ggacctgaag aacgacaaca ccgacgagga cgagatcagc     360
gacgaggagc tggacgccct ggccgacgac ctggtgcacg ccctgggcgt gatcgacgag     420
gtggaggaga tcgacctgtt cggcagcgtg accggcgacg ccgacgtgga cgtggagcag     480
gaggaggacg agaacgacga cgacgacaac gaggacgacg acgacgacac cgaggacgac     540
gaccacccca ccaagctgca caactggcag atcaagagac tggcctacgt gctgaagggc     600
ggcagaagac actgcaccat gaagcagggc gccgccgacg tgaccctgga cagagcctac     660
gtgctggagc tgctgcacga ccccccccc aaggtggtgg ccgtgaccgc caccctgccc     720
gacgagaagc ccccgtggc cgccccgag cagagcagcc ccgaccccag cccgtggac       780 agcctgagcg ccgaggaggt ggtggtggag cccaaggaga aggtgaagga cgaggccgtg     840
cacgtgatgc agcagagatg gagcgcccag aagagagtga agaaggccca catcgagacc     900
ctggagaagg tgtacagaag aagcaagaga cccaccaacg ccgtggtgag cagcatcgtg     960
caggtgacca acctgcccag aaagagagtg ctgaagtggt tcgaggacaa gagagccgag    1020
gacggcgtgc ccgacaagag agccccctac caggcccca tg                        1062
```

```
<210> SEQ ID NO 15
<211> LENGTH: 354
<212> TYPE: PRT
<213> ORGANISM: Artificial sequence
<220> FEATURE:
<223> OTHER INFORMATION: Amino acid sequence OCP3, variant 10

<400> SEQUENCE: 15

Met Ile Lys Ala Met Ala Met Ser Ser Ala Met Val Met Ser His Met
1               5                   10                  15

Lys Pro Pro Ser Phe Thr Thr Ser Ser Gly Leu Ser Ala Asn Arg Val
            20                  25                  30

Leu Phe His Asn Lys Asn Ile Ser Pro Thr Gly Ile Ser Leu Pro Leu
        35                  40                  45

Leu Asn Pro Ser His Ser Leu Gly Val Trp Ala Arg Met His Asn His
    50                  55                  60

Lys Met Tyr Leu Cys Ser Ser Ser Cys Thr Pro Lys His Asn Lys Lys
65                  70                  75                  80

His Ser Leu Glu Met Ala Glu Asn Gly Gly Val Glu Glu Asp Glu Asp
                85                  90                  95

Pro Phe Glu Val Leu Phe Asn Leu Leu Glu Glu Asp Leu Lys Asn Asp
            100                 105                 110

Asn Thr Asp Glu Asp Glu Ile Ser Asp Glu Glu Leu Asp Ala Leu Ala
        115                 120                 125

Asp Asp Leu Val His Ala Leu Gly Val Ile Asp Glu Val Glu Glu Ile
    130                 135                 140

Asp Leu Phe Gly Ser Val Thr Gly Asp Ala Asp Val Asp Val Glu Gln
145                 150                 155                 160

Glu Glu Asp Glu Asn Asp Asp Asp Asn Glu Asp Asp Asp Asp
                165                 170                 175

Thr Glu Asp Asp Asp His Pro Thr Lys Leu His Asn Trp Gln Ile Lys
        180                 185                 190

Arg Leu Ala Tyr Val Leu Lys Gly Gly Arg Arg His Cys Thr Met Lys
    195                 200                 205

Gln Gly Ala Ala Asp Val Thr Leu Asp Arg Ala Tyr Val Leu Glu Leu
210                 215                 220

Leu His Asp Pro Pro Lys Val Val Ala Val Thr Ala Thr Leu Pro
225                 230                 235                 240

Asp Glu Lys Pro Pro Val Ala Ala Pro Glu Gln Ser Ser Pro Asp Pro
            245                 250                 255

Ser Pro Val Asp Ser Leu Ser Ala Glu Glu Val Val Val Glu Pro Lys
        260                 265                 270

Glu Lys Val Lys Asp Glu Ala Val His Val Met Gln Gln Arg Trp Ser
    275                 280                 285

Ala Gln Lys Arg Val Lys Lys Ala His Ile Glu Thr Leu Glu Lys Val
    290                 295                 300

Tyr Arg Arg Ser Lys Arg Pro Thr Asn Ala Val Val Ser Ser Ile Val
305                 310                 315                 320

Gln Val Thr Asn Leu Pro Arg Lys Arg Val Leu Lys Trp Phe Glu Asp
            325                 330                 335

Lys Arg Ala Glu Asp Gly Val Pro Asp Lys Arg Ala Pro Tyr Gln Ala
        340                 345                 350

Pro Met
```

<210> SEQ ID NO 16
<211> LENGTH: 1062
<212> TYPE: DNA
<213> ORGANISM: Artificial sequence
<220> FEATURE:
<223> OTHER INFORMATION: Nucleotide sequence OCP3, variant 11

<400> SEQUENCE: 16

```
atgatccaca tcatggccct gaccaccgcc atggtggtgt gccacctgca cccccccagc      60
ttcagcagca gcagcggcat gagcgtgaac cacatcctgt acagaaacag acaggccagc     120
ccctgcggcc tgagcctgcc catcctgcag cccagccaca gcgtggccgt gttcgccaag     180
ggcaagaaca agaagggctt catgagcacc agcagcagca gccccaagaa gcagagaaag     240
aagagcctgg acggcgccga gaacggcatg ggcgaggagg aggaggaccc ctacgaggcc     300
ggcttcaacc tgctggagga ggacctgaga aacgacaaca gcgacgacga ggacggcagc     360
gaggacgagc tggaggccct ggccgacgag ggcgccagag ccctgggcgt gggcgaggac     420
gtggaggaca tcgacctgtt cgcctgcgtg accggcgacg tggacgccga cgccgacaac     480
gacgaggacg accaggacga cgacgacaac gaggacgacg acgaggacag cgaggaggac     540
gagagaccca ccagaggcaa gactggcagc tgcaccacg gcgcctacgc cggcagactg     600
ggccacagaa agaccagcat caagaacctg gccgccgagg tgtgcctgga cagactgttc     660
gtgatcgagc tgctgagaga cccccccccc agactgatga tgctgagcgc caccatcccc     720
gacgagaagc cccccctggg cgccccgag aacaccagcc ccgagcccac ccccgtggag     780
agcctgtgcg ccgaggaggt ggtgctggag cccaaggaga aggtgaagga cgaggccgtg     840
cacgtgatgc agcagagatg gagcgcccag aagagagtga agaaggccca catcgagacc     900
ctggagaagg tgtacagaag aagcaagaga cccaccaacg ccgtggtgag cagcatcgtg     960
caggtgacca acctgcccag aaagagagtg ctgaagtggt cgaggacaa gagagccgag    1020
gacggcgtgc ccgacaagag agcccccac cagatcccg gc                       1062
```

<210> SEQ ID NO 17
<211> LENGTH: 354
<212> TYPE: PRT
<213> ORGANISM: Artificial sequence
<220> FEATURE:
<223> OTHER INFORMATION: Amino acid sequence OCP3, variant 11

<400> SEQUENCE: 17

```
Met Ile His Ile Met Ala Leu Thr Thr Ala Met Val Val Cys His Leu
1               5                   10                  15

His Pro Pro Ser Phe Ser Ser Ser Gly Met Ser Val Asn His Ile
            20                  25                  30

Leu Tyr Arg Asn Arg Gln Ala Ser Pro Cys Gly Leu Ser Leu Pro Ile
        35                  40                  45

Leu Gln Pro Ser His Ser Val Ala Val Phe Ala Lys Gly Lys Asn Lys
    50                  55                  60

Lys Gly Phe Met Ser Thr Ser Ser Ser Pro Lys Lys Gln Arg Lys
65                  70                  75                  80

Lys Ser Leu Asp Gly Ala Glu Asn Gly Met Gly Glu Glu Glu Asp
                85                  90                  95

Pro Tyr Glu Ala Gly Phe Asn Leu Leu Glu Glu Asp Leu Arg Asn Asp
            100                 105                 110

Asn Ser Asp Asp Glu Asp Gly Ser Glu Asp Glu Leu Glu Ala Leu Ala
        115                 120                 125
```

```
Asp Gly Ala Arg Ala Leu Gly Val Gly Glu Asp Val Glu Asp Ile
    130                 135                 140

Asp Leu Phe Ala Cys Val Thr Gly Asp Val Asp Ala Asp Ala Asp Asn
145                 150                 155                 160

Asp Glu Asp Asp Gln Asp Asp Asp Asn Glu Asp Asp Asp Glu Asp
                165                 170                 175

Ser Glu Asp Glu Arg Pro Thr Arg Gly Lys Asn Trp Gln Leu His
            180                 185                 190

His Gly Ala Tyr Ala Gly Arg Leu Gly His Arg Lys Thr Ser Ile Lys
        195                 200                 205

Asn Leu Ala Ala Glu Val Cys Leu Asp Arg Leu Phe Val Ile Glu Leu
    210                 215                 220

Leu Arg Asp Pro Pro Arg Leu Met Met Leu Ser Ala Thr Ile Pro
225                 230                 235                 240

Asp Glu Lys Pro Pro Leu Gly Ala Pro Glu Asn Thr Ser Pro Glu Pro
                245                 250                 255

Thr Pro Val Glu Ser Leu Cys Ala Glu Val Val Leu Glu Pro Lys
            260                 265                 270

Glu Lys Val Lys Asp Glu Ala Val His Val Met Gln Gln Arg Trp Ser
        275                 280                 285

Ala Gln Lys Arg Val Lys Lys Ala His Ile Glu Thr Leu Glu Lys Val
    290                 295                 300

Tyr Arg Arg Ser Lys Arg Pro Thr Asn Ala Val Val Ser Ser Ile Val
305                 310                 315                 320

Gln Val Thr Asn Leu Pro Arg Lys Arg Val Leu Lys Trp Phe Glu Asp
                325                 330                 335

Lys Arg Ala Glu Asp Gly Val Pro Asp Lys Arg Ala Pro Tyr Gln Ile
            340                 345                 350

Pro Gly

<210> SEQ ID NO 18
<211> LENGTH: 1062
<212> TYPE: DNA
<213> ORGANISM: Artificial sequence
<220> FEATURE:
<223> OTHER INFORMATION: Nucleotide sequence OCP3, variant 12

<400> SEQUENCE: 18
atgatcaagg ccgtggccgg cagcagcgcc ggcgtgatga gcagactgca ccccccctgc      60
ttctgcagca gcagcgccct gagcgtgaac agagtgctgt acagacagag aaacgccagc     120
ccctgcggcc tgagcctgcc catcctgaac cccagcagaa gcgtgctgat cttcgccaga     180
ggcagaaacc acaagggctt cgtgagcacc agcaccagca gccccaagca acagagaaag     240
aagagcctgg agggcgccga ccagggcatg ggcgaggagg aggaggaccc cttcgaggcc     300
ctgttcaacc tgctggagga ggacctgaag aacgaccagt cgacgacga ggagatcagc     360 gaggaggagc tggaggccgg cgccgacgag ctgggcagag ccctgatcgt gggcgaggac     420
gtggaggacg cgacctgta cggctgcgtg accggcgacg tggaggtgga cgtggagaac     480
gacgacgacg agaacgacga cgacgacaac gacgacgacg acgacgacag cgaggaggac     540
gagaagccct gcaagctgaa gaactggcag ctgaagcacc tggcctacgc cggcaaggtg     600
ggcagaagac acaccagcat caagaacatc ggcgccgacg gctgcctgga cagagcctac     660
gtgctggagc tgctgcacga cccccccccc aagatgctga tgatgagcat gtgcctgccc     720
```

```
gacgagaagc cccccgtggc catccccgag aacagcagcc ccgaccccag ccccgtggag      780
tgcctgagcg ccgaggacgt ggtggtggag cccaaggaga aggtgaagga cgaggccgtg      840
cacgtgatgc agcagagatg gagcgcccag aagagagtga agaaggccca catcgagacc      900
ctggagaagg tgtacagaag aagcaagaga cccaccaacg ccgtggtgag cagcatcgtg      960
caggtgacca acctgcccag aaagagagtg ctgaagtggt tcgaggacaa agagagccgag   1020 gacggcgtgc ccgacaagag agccccctac caggcccccg tg                       1062
```

<210> SEQ ID NO 19
<211> LENGTH: 354
<212> TYPE: PRT
<213> ORGANISM: Artificial sequence
<220> FEATURE:
<223> OTHER INFORMATION: Amino acid sequence OCP3, variant 12

<400> SEQUENCE: 19

```
Met Ile Lys Ala Val Ala Gly Ser Ser Ala Gly Val Met Ser Arg Leu
1               5                   10                  15

His Pro Pro Cys Phe Cys Ser Ser Ala Leu Ser Val Asn Arg Val
            20                  25                  30

Leu Tyr Arg Gln Arg Asn Ala Ser Pro Cys Gly Leu Ser Leu Pro Ile
        35                  40                  45

Leu Asn Pro Ser Arg Ser Val Leu Ile Phe Ala Arg Gly Arg Asn His
    50                  55                  60

Lys Gly Phe Val Ser Thr Ser Ser Ser Pro Lys His Asn Arg Lys
65                  70                  75                  80

Lys Ser Leu Glu Gly Ala Asp Gln Gly Met Gly Glu Glu Glu Asp
                85                  90                  95

Pro Phe Glu Ala Leu Phe Asn Leu Leu Glu Glu Asp Leu Lys Asn Asp
            100                 105                 110

Gln Cys Asp Asp Glu Glu Ile Ser Glu Glu Glu Leu Glu Ala Gly Ala
        115                 120                 125

Asp Glu Leu Gly Arg Ala Leu Ile Val Gly Glu Asp Val Glu Asp Gly
    130                 135                 140

Asp Leu Tyr Gly Cys Val Thr Gly Asp Val Glu Val Asp Val Glu Asn
145                 150                 155                 160

Asp Asp Asp Glu Asn Asp Asp Asp Asn Asp Asp Asp Asp Asp
                165                 170                 175

Ser Glu Glu Asp Glu Lys Pro Cys Lys Leu Lys Asn Trp Gln Leu Lys
            180                 185                 190

His Leu Ala Tyr Ala Gly Lys Val Gly Arg Arg His Thr Ser Ile Lys
        195                 200                 205

Asn Ile Gly Ala Asp Gly Cys Leu Asp Arg Ala Tyr Val Leu Glu Leu
    210                 215                 220

Leu His Asp Pro Pro Lys Met Leu Met Met Ser Met Cys Leu Pro
225                 230                 235                 240

Asp Glu Lys Pro Pro Val Ala Ile Pro Glu Asn Ser Ser Pro Asp Pro
                245                 250                 255

Ser Pro Val Glu Cys Leu Ser Ala Glu Asp Val Val Glu Pro Lys
            260                 265                 270

Glu Lys Val Lys Asp Glu Ala Val His Val Met Gln Gln Arg Trp Ser
        275                 280                 285

Ala Gln Lys Arg Val Lys Lys Ala His Ile Glu Thr Leu Glu Lys Val
    290                 295                 300
```

```
Tyr Arg Arg Ser Lys Arg Pro Thr Asn Ala Val Val Ser Ile Val
305                 310                 315                 320

Gln Val Thr Asn Leu Pro Arg Lys Arg Val Leu Lys Trp Phe Glu Asp
                325                 330                 335

Lys Arg Ala Glu Asp Gly Val Pro Asp Lys Arg Ala Pro Tyr Gln Ala
            340                 345                 350

Pro Val

<210> SEQ ID NO 20
<211> LENGTH: 1062
<212> TYPE: DNA
<213> ORGANISM: Artificial sequence
<220> FEATURE:
<223> OTHER INFORMATION: Nucleotide sequence OCP3, variant 13

<400> SEQUENCE: 20
atgatcaagg ccatggccct gagcagcgcc ggcgtggtga gccacctgca ccccccagc      60 ttcagcagca gcagcctgct gagcgtgaac agagtgctgt tcagaaacag aaacgccagc    120
ccctgcggcc tgagcctgcc cggcctgaac ccctgcagaa gcgtgctggt gttcgccaga    180
ggcaagaaca gaaagggctt cgtgagctgc agcagcagca gccccaagca caacaagaag    240
cacagcctgg acggcgccga ccagggcggc ctggaggacg aggacgaccc cttcgaggcc    300
ctgttcaacc tgctggagga cgacctgaag aacgaccaga gcgacgagga ggagatcagc    360
gaggacgagc tggaggccct ggccgacgag ctggccagag ccctgggcct gggcgacgac    420
gtggacgaca tcgacgcctt cggcagcgtg accggcgacg tggacgtgga ggtggacaac    480
gaggacgacg acaacgacga cgacgagcag gacgacgacg acgacgacag cgacgaggac    540
gagagaccct gcaagctgaa gaactaccag ctgaagagac tggcctacgc cctgaaggcc    600
ggcagaagaa agaccagcat caagaacctg ccgccgaga tgtgcctgga ccacgcctac    660
gtgctggagc tgctgagaga cccccccccc aagctgctga tgctgagcgc accctgccc    720 gacgagagac cccccgtggc cgtgcccgag aacagcagcc cgaccccag ccccgtggag    780 agcctgagcg cgacgacgt ggtggtggag cccaaggaga aggtgaagga cgaggccgtg    840
cacgtgatgc agcagagatg gagcgcccag aagagagtga agaaggccca catcgagacc    900
ctggagaagg tgtacagaag aagcaagaga cccaccaacg ccgtggtgag cagcatcgtg    960
caggtgacca acctgcccag aaagagagtg ctgaagtggt tcgaggacaa gagagccgag   1020
gacggcgtgc ccgacaagag agccccctac caggccccg tg                      1062

<210> SEQ ID NO 21
<211> LENGTH: 354
<212> TYPE: PRT
<213> ORGANISM: Artificial sequence
<220> FEATURE:
<223> OTHER INFORMATION: Amino acid sequence OCP3, variant 13

<400> SEQUENCE: 21

Met Ile Lys Ala Met Ala Leu Ser Ser Ala Gly Val Val Ser His Leu
1               5                   10                  15

His Pro Pro Ser Phe Ser Ser Ser Leu Leu Ser Val Asn Arg Val
                20                  25                  30

Leu Phe Arg Asn Arg Asn Ala Ser Pro Cys Gly Leu Ser Leu Pro Gly
            35                  40                  45

Leu Asn Pro Cys Arg Ser Val Leu Val Phe Ala Arg Gly Lys Asn Arg
        50                  55                  60
```

```
Lys Gly Phe Val Ser Cys Ser Ser Ser Pro Lys His Asn Lys Lys
 65                  70                  75                  80

His Ser Leu Asp Gly Ala Asp Gln Gly Gly Leu Glu Asp Glu Asp
                 85                  90                  95

Pro Phe Glu Ala Leu Phe Asn Leu Leu Glu Asp Asp Leu Lys Asn Asp
                100                 105                 110

Gln Ser Asp Glu Glu Ile Ser Glu Asp Glu Leu Glu Ala Leu Ala
                115                 120                 125

Asp Glu Leu Ala Arg Ala Leu Gly Leu Gly Asp Val Asp Asp Ile
            130                 135                 140

Asp Ala Phe Gly Ser Val Thr Gly Asp Val Asp Val Glu Val Asp Asn
145                 150                 155                 160

Glu Asp Asp Asp Asn Asp Asp Glu Gln Asp Asp Asp Asp Asp
                165                 170                 175

Ser Asp Glu Asp Glu Arg Pro Cys Lys Leu Lys Asn Tyr Gln Leu Lys
                180                 185                 190

Arg Leu Ala Tyr Ala Leu Lys Ala Gly Arg Arg Lys Thr Ser Ile Lys
            195                 200                 205

Asn Leu Ala Ala Glu Met Cys Leu Asp His Ala Tyr Val Leu Glu Leu
            210                 215                 220

Leu Arg Asp Pro Pro Lys Leu Leu Met Leu Ser Ala Thr Leu Pro
225                 230                 235                 240

Asp Glu Arg Pro Pro Val Ala Val Pro Glu Asn Ser Ser Pro Asp Pro
                245                 250                 255

Ser Pro Val Glu Ser Leu Ser Gly Asp Asp Val Val Glu Pro Lys
                260                 265                 270

Glu Lys Val Lys Asp Glu Ala Val His Val Met Gln Gln Arg Trp Ser
            275                 280                 285

Ala Gln Lys Arg Val Lys Lys Ala His Ile Glu Thr Leu Glu Lys Val
            290                 295                 300

Tyr Arg Arg Ser Lys Arg Pro Thr Asn Ala Val Val Ser Ser Ile Val
305                 310                 315                 320

Gln Val Thr Asn Leu Pro Arg Lys Arg Val Leu Lys Trp Phe Glu Asp
                325                 330                 335

Lys Arg Ala Glu Asp Gly Val Pro Asp Lys Arg Ala Pro Tyr Gln Ala
                340                 345                 350

Pro Val

<210> SEQ ID NO 22
<211> LENGTH: 1062
<212> TYPE: DNA
<213> ORGANISM: Artificial sequence
<220> FEATURE:
<223> OTHER INFORMATION: Nucleotide sequence OCP3, variant 14

<400> SEQUENCE: 22
atgatcaagg ccgtggccat gagcagcgcc ggcgtggtga gccacctgca ccccccagc        60 ttcagcagca ccagcggcct gagcgtgaac agagtgctgt tcagaaacag aaacgcctgc      120
ccctgcggcc tgaccggccc catcctgcag cccagcagaa gcgtgatcgt gttcgccaga      180
ggcaagaaca gaaagggctt cgtgagcagc agcagcagca gccccaagaa gaacaagaag      240
aagtgcctgg acggcgccga caacggcggc ggcgaggagg aggaggaccc cttcgaggcc      300
ctgttcaacc tgctggagga ggagctgaag aacgacaaca cgacgacga ggagatcagc      360 gaggaggagc tggaggccgt ggccgacgag ctggccagag ccctgggcgt gggcgacgac      420
```

```
gtggacgaga tcgacctgtt cgccagcgtg accggcgacg tggacgtgga ggtggacaac    480
gacgacgacg acaacgagga cgacgagaac gacgaggacg acgaggacag cgaggaggac    540
gagagaccca ccaagctgaa gaactggcag ctgcacaagc tggcctacgc cctgaaggcc    600
ggcagaagaa agaccagcat caagaacctg gccgccgagg tgagcctgga gagagccttc    660
gtgctggagc tgctgagaga ccccccccc aagctgctga tgctgagcat gaccctgccc    720
gaggagaagc ccccgtggc cgcccccgag cagagcagcc ccgaccccag ccccgtggag    780
agcatcagcg ccgaggacgt ggtggtggag cccaaggaga aggtgaagga cgaggccgtg    840
cacgtgatgc agcagagatg gagcgcccag aagagagtga agaaggccca catcgagacc    900
ctggagaagg tgtacagaag aagcaagaga cccaccaacg ccgtggtgag cagcatcgtg    960
caggtgacca acctgcccag aaagagagtg ctgaagtggt tcgaggacaa gagagccgag   1020
gacggcgtgc ccgacaagag agccccctac caggcccccg tg                      1062
```

<210> SEQ ID NO 23
<211> LENGTH: 354
<212> TYPE: PRT
<213> ORGANISM: Artificial sequence
<220> FEATURE:
<223> OTHER INFORMATION: Amino acid sequence OCP3, variant 14

<400> SEQUENCE: 23

```
Met Ile Lys Ala Val Ala Met Ser Ser Ala Gly Val Val Ser His Leu
1               5                   10                  15

His Pro Pro Ser Phe Ser Ser Thr Ser Gly Leu Ser Val Asn Arg Val
            20                  25                  30

Leu Phe Arg Asn Arg Asn Ala Cys Pro Cys Gly Leu Thr Gly Pro Ile
        35                  40                  45

Leu Gln Pro Ser Arg Ser Val Ile Val Phe Ala Arg Gly Lys Asn Arg
    50                  55                  60

Lys Gly Phe Val Ser Ser Ser Ser Ser Pro Lys Lys Asn Lys Lys
65                  70                  75                  80

Lys Cys Leu Asp Gly Ala Asp Asn Gly Gly Glu Glu Glu Asp
                85                  90                  95

Pro Phe Glu Ala Leu Phe Asn Leu Leu Glu Glu Glu Leu Lys Asn Asp
            100                 105                 110

Asn Ser Asp Asp Glu Glu Ile Ser Glu Glu Glu Leu Glu Ala Val Ala
        115                 120                 125

Asp Glu Leu Ala Arg Ala Leu Gly Val Gly Asp Asp Val Asp Glu Ile
    130                 135                 140

Asp Leu Phe Ala Ser Val Thr Gly Asp Val Asp Val Glu Val Asp Asn
145                 150                 155                 160

Asp Asp Asp Asp Asn Glu Asp Glu Asn Asp Glu Asp Glu Asp
                165                 170                 175

Ser Glu Glu Asp Glu Arg Pro Thr Lys Leu Lys Asn Trp Gln Leu His
            180                 185                 190

Lys Leu Ala Tyr Ala Leu Lys Ala Gly Arg Arg Lys Thr Ser Ile Lys
        195                 200                 205

Asn Leu Ala Ala Glu Val Ser Leu Glu Arg Ala Phe Val Leu Glu Leu
    210                 215                 220

Leu Arg Asp Pro Pro Lys Leu Leu Met Leu Ser Met Thr Leu Pro
225                 230                 235                 240

Glu Glu Lys Pro Pro Val Ala Ala Pro Glu Gln Ser Ser Pro Asp Pro
```

```
                245                 250                 255
Ser Pro Val Glu Ser Ile Ser Ala Glu Asp Val Val Glu Pro Lys
            260                 265                 270

Glu Lys Val Lys Asp Glu Ala Val His Val Met Gln Gln Arg Trp Ser
            275                 280                 285

Ala Gln Lys Arg Val Lys Lys Ala His Ile Glu Thr Leu Glu Lys Val
        290                 295                 300

Tyr Arg Arg Ser Lys Arg Pro Thr Asn Ala Val Val Ser Ser Ile Val
305                 310                 315                 320

Gln Val Thr Asn Leu Pro Arg Lys Arg Val Leu Lys Trp Phe Glu Asp
                325                 330                 335

Lys Arg Ala Glu Asp Gly Val Pro Asp Lys Arg Ala Pro Tyr Gln Ala
            340                 345                 350

Pro Val
```

<210> SEQ ID NO 24
<211> LENGTH: 1062
<212> TYPE: DNA
<213> ORGANISM: Artificial sequence
<220> FEATURE:
<223> OTHER INFORMATION: Nucleotide sequence OCP3, variant 15

<400> SEQUENCE: 24

```
atgatcaagg ccatggccct gagcagcgcc ggcgtggtga gccacctgca cccccccagc      60
ttcagcagca gcagcggcct gagcgtgaac agagtgctgt tcagaaacag aaacgccagc     120
ccctgcggcc tgagcctgcc catcctgaac cccagcagaa gcgtgctggt gttcgccaga     180
ggcaagaaca gaaagggctt cgtgagcagc agcagcagca gccccaagaa gaacaagaag     240
aagagcctgg acggcgccga gaacggcggc ggcgaggagg aggaggaccc cttcgaggcc     300
ctgttcaacc tgctggagga ggacctgaag aacgacaaca gcgacgacga ggagatcagc     360
gacgacgagc tggaggccct ggccgacgac ctggccagag ccctgctggt gggcgacgac     420
gtggacgaca tcgacctgtt cctgagcctg accggcgagg tggacgtgga cgtggacaac     480
gacgacgacg acaacgacga cgacgagaac gacgaggacg acgacgacag cgacgacgac     540
gagagaccca ccaagctgaa gaactggcag ctgaagagac tggcctacgc cctgaaggcc     600
ggcagaagaa agagcagcat caagaacctg gccgccgagg tgtgcctgga cagagcctac     660
gtgctggagc tgctgagaga cccccccccc aagctgctga tgctgaccgc caccctgccc     720
gacgagaagc cccccgtggc cgcccccgag cagagcagcc ccgaccccag ccccgtggag     780
agcctgaccg ccgaggacgt ggtggtggag cccaaggaga aggtgaagga cgaggccgtg     840
cacgtgatgc agcagagatg gagcgcccag aagagagtga agaaggccca catcgagacc     900
ctggagaagg tgtacagaag aagcaagaga cccaccaacg ccgtggtgag cagcatcgtg     960
caggtgacca acctgcccag aaagagagtg ctgaagtggt tcgaggacaa gagagccgag    1020
gacggcgtgc ccgacaagag agccccctac caggcccccg tg                       1062
```

<210> SEQ ID NO 25
<211> LENGTH: 354
<212> TYPE: PRT
<213> ORGANISM: Artificial sequence
<220> FEATURE:
<223> OTHER INFORMATION: Amino acid sequence OCP3, variant 15

<400> SEQUENCE: 25

Met Ile Lys Ala Met Ala Leu Ser Ser Ala Gly Val Val Ser His Leu

```
1               5                   10                  15
His Pro Pro Ser Phe Ser Ser Ser Gly Leu Ser Val Asn Arg Val
            20                  25                  30

Leu Phe Arg Asn Arg Asn Ala Ser Pro Cys Gly Leu Ser Leu Pro Ile
            35                  40                  45

Leu Asn Pro Ser Arg Ser Val Leu Val Phe Ala Arg Gly Lys Asn Arg
 50                 55                  60

Lys Gly Phe Val Ser Ser Ser Ser Ser Pro Lys Lys Asn Lys Lys
 65                 70                  75                  80

Lys Ser Leu Asp Gly Ala Glu Asn Gly Gly Glu Glu Glu Asp
                85                  90                  95

Pro Phe Glu Ala Leu Phe Asn Leu Leu Glu Glu Asp Leu Lys Asn Asp
                100                 105                 110

Asn Ser Asp Asp Glu Glu Ile Ser Asp Glu Leu Glu Ala Leu Ala
            115                 120                 125

Asp Asp Leu Ala Arg Ala Leu Leu Val Gly Asp Asp Val Asp Asp Ile
            130                 135                 140

Asp Leu Phe Leu Ser Leu Thr Gly Glu Val Asp Val Asp Val Asp Asn
145                 150                 155                 160

Asp Asp Asp Asp Asn Asp Asp Glu Asn Asp Glu Asp Asp Asp
                165                 170                 175

Ser Asp Asp Asp Glu Arg Pro Thr Lys Leu Lys Asn Trp Gln Leu Lys
            180                 185                 190

Arg Leu Ala Tyr Ala Leu Lys Ala Gly Arg Arg Lys Ser Ser Ile Lys
            195                 200                 205

Asn Leu Ala Ala Glu Val Cys Leu Asp Arg Ala Tyr Val Leu Glu Leu
 210                215                 220

Leu Arg Asp Pro Pro Lys Leu Leu Met Leu Thr Ala Thr Leu Pro
225                 230                 235                 240

Asp Glu Lys Pro Pro Val Ala Ala Pro Glu Gln Ser Ser Pro Asp Pro
            245                 250                 255

Ser Pro Val Glu Ser Leu Thr Ala Glu Asp Val Val Glu Pro Lys
            260                 265                 270

Glu Lys Val Lys Asp Glu Ala Val His Val Met Gln Gln Arg Trp Ser
            275                 280                 285

Ala Gln Lys Arg Val Lys Lys Ala His Ile Glu Thr Leu Glu Lys Val
            290                 295                 300

Tyr Arg Arg Ser Lys Arg Pro Thr Asn Ala Val Val Ser Ser Ile Val
305                 310                 315                 320

Gln Val Thr Asn Leu Pro Arg Lys Arg Val Leu Lys Trp Phe Glu Asp
                325                 330                 335

Lys Arg Ala Glu Asp Gly Val Pro Asp Lys Arg Ala Pro Tyr Gln Ala
                340                 345                 350

Pro Val

<210> SEQ ID NO 26
<211> LENGTH: 1062
<212> TYPE: DNA
<213> ORGANISM: Artificial sequence
<220> FEATURE:
<223> OTHER INFORMATION: Nucleotide sequence OCP3, variant 16

<400> SEQUENCE: 26
atgatcaagg ccatggccct gagcagcgcc ggcgtggtga gccacctgca cccccccagc      60
```

| | |
|---|---|
| ttcagcagca gcagcggcct gagcgtgaac agagtggcct tcagaaacag aaacgccagc | 120 |
| ccctgcggcg tgagcctgcc catcctgaac cccagcagaa gcgtgctggt gttcgccaga | 180 |
| ggcaagaaca gaaagggctt cgtgtgcagc agcagcagca gccccaagaa gaacaagaag | 240 |
| aagagcctgg agggcgccga caacggcctg ggcgaggagg aggaggaccc cttcgaggcc | 300 |
| ctgttcaacc tgctggagga ggacctgaag aacgaccaga gcgacgacga ggagatcagc | 360 |
| gaggaggagc tggaggccct ggccgacgag ctggccagag ccctgggcgt gatggacgac | 420 |
| gtggacgaca tcgacctgtt cggcagcgtg accggcgacg tggacgtgga cgtggacaac | 480 |
| gacgacgacg acaacgacga cgacgacaac gacgacgacg acgacgacag cgaggaggac | 540 |
| gagagaccca cccacctgaa gaactggcag ctgaagagac tggcctacgc cctgaaggcc | 600 |
| ggcagaagaa agaccagcat caagaacctg gccgccgagg tgtgcctgga cagaatgtac | 660 |
| gtgctggagc tgctgagaga cccccccccc aagctgctga tgctgagcgc caccctgccc | 720 |
| gacgagaagc cccccgtggc cgcccccgag aacaccagcc ccgaccccag ccccgtggag | 780 |
| agcctgagcg ccgaggacgt ggtggtggag cccaaggaga aggtgaagga cgaggccgtg | 840 |
| cacgtgatgc agcagagatg gagcgcccag aagagagtga agaaggccca catcgagacc | 900 |
| ctggagaagg tgtacagaag aagcaagaga cccaccaacg ccgtggtgag cagcatcgtg | 960 |
| caggtgacca acctgcccag aaagagagtg ctgaagtggt tcgaggacaa gagagccgag | 1020 |
| gacggcgtgc ccgacaagag agccccctac caggccccccg tg | 1062 |

<210> SEQ ID NO 27
<211> LENGTH: 354
<212> TYPE: PRT
<213> ORGANISM: Artificial sequence
<220> FEATURE:
<223> OTHER INFORMATION: Amino acid sequence OCP3, variant 16

<400> SEQUENCE: 27

```
Met Ile Lys Ala Met Ala Leu Ser Ser Ala Gly Val Val Ser His Leu
1               5                   10                  15

His Pro Pro Ser Phe Ser Ser Ser Gly Leu Ser Val Asn Arg Val
            20                  25                  30

Ala Phe Arg Asn Arg Asn Ala Ser Pro Cys Gly Val Ser Leu Pro Ile
        35                  40                  45

Leu Asn Pro Ser Arg Ser Val Leu Val Phe Ala Arg Gly Lys Asn Arg
    50                  55                  60

Lys Gly Phe Val Cys Ser Ser Ser Ser Pro Lys Lys Asn Lys Lys
65                  70                  75                  80

Lys Ser Leu Glu Gly Ala Asp Asn Gly Leu Gly Glu Glu Glu Glu Asp
                85                  90                  95

Pro Phe Glu Ala Leu Phe Asn Leu Leu Glu Glu Asp Leu Lys Asn Asp
            100                 105                 110

Gln Ser Asp Asp Glu Glu Ile Ser Glu Glu Leu Glu Ala Leu Ala
        115                 120                 125

Asp Glu Leu Ala Arg Ala Leu Gly Val Met Asp Asp Val Asp Asp Ile
    130                 135                 140

Asp Leu Phe Gly Ser Val Thr Gly Asp Val Asp Val Asp Val Asp Asn
145                 150                 155                 160

Asp Asp Asp Asp Asn Asp Asp Asp Asn Asp Asp Asp Asp Asp Asp Asp
                165                 170                 175

Ser Glu Glu Asp Glu Arg Pro Thr His Leu Lys Asn Trp Gln Leu Lys
            180                 185                 190
```

-continued

```
Arg Leu Ala Tyr Ala Leu Lys Ala Gly Arg Arg Lys Thr Ser Ile Lys
        195                 200                 205

Asn Leu Ala Ala Glu Val Cys Leu Asp Arg Met Tyr Val Leu Glu Leu
    210                 215                 220

Leu Arg Asp Pro Pro Lys Leu Leu Met Leu Ser Ala Thr Leu Pro
225             230                 235                 240

Asp Glu Lys Pro Pro Val Ala Ala Pro Glu Asn Thr Ser Pro Asp Pro
                245                 250                 255

Ser Pro Val Glu Ser Leu Ser Ala Glu Asp Val Val Val Glu Pro Lys
            260                 265                 270

Glu Lys Val Lys Asp Glu Ala Val His Val Met Gln Gln Arg Trp Ser
        275                 280                 285

Ala Gln Lys Arg Val Lys Lys Ala His Ile Glu Thr Leu Glu Lys Val
    290                 295                 300

Tyr Arg Arg Ser Lys Arg Pro Thr Asn Ala Val Val Ser Ser Ile Val
305             310                 315                 320

Gln Val Thr Asn Leu Pro Arg Lys Arg Val Leu Lys Trp Phe Glu Asp
            325                 330                 335

Lys Arg Ala Glu Asp Gly Val Pro Asp Lys Arg Ala Pro Tyr Gln Ala
            340                 345                 350

Pro Val
```

FUNGAL RESISTANT PLANTS EXPRESSING OCP3

This application is a National Stage application of International Application No. PCT/EP2013/055319, filed Mar. 15, 2013, which claims the benefit of U.S. Provisional Application No. 61/622,538, filed Apr. 11, 2012, the entire contents of which are hereby incorporated herein by reference. This application also claims priority under 35 U.S.C. § 119 to European Patent Application No. 12163703.7, filed Apr. 11, 2012, the entire contents of which are hereby incorporated herein by reference.

REFERENCE TO SEQUENCE LISTING SUBMITTED VIA EFS-WEB

This application was filed electronically via EFS-Web and includes an electronically submitted sequence listing in .txt format. The .txt file contains a sequence listing entitled "Sequence_List.txt" created on Sep. 12, 2014, and is 57,344 bytes in size. The sequence listing contained in this .txt file is part of the specification and is hereby incorporated by reference herein in its entirety.

SUMMARY OF THE INVENTION

The present invention relates to a method of increasing resistance against fungal pathogens, in particular, pathogens of the family Phacopsoraceae, for example soybean rust, in plants, plant parts, and/or plant cells. This is achieved by increasing the expression and/or activity of an OCP3 protein in a plant, plant part and/or plant cell in comparison to wild type plants, wild type plant parts and/or wild type plant cells.

Furthermore, the invention relates to transgenic plants, plant parts, and/or plant cells having an increased resistance against fungal pathogens, in particular, pathogens of the family Phacopsoraceae, for example soybean rust, and to recombinant expression vectors comprising a sequence that is identical or homologous to a sequence encoding an OCP3 protein.

BACKGROUND OF THE INVENTION

The cultivation of agricultural crop plants serves mainly for the production of foodstuffs for humans and animals. Monocultures in particular, which are the rule nowadays, are highly susceptible to an epidemic-like spreading of diseases. The result is markedly reduced yields. To date, the pathogenic organisms have been controlled mainly by using pesticides. Nowadays, the possibility of directly modifying the genetic disposition of a plant or pathogen is also open to man.

Resistance generally describes the ability of a plant to prevent, or at least curtail the infestation and colonization by a harmful pathogen. Different mechanisms can be discerned in the naturally occurring resistance, with which the plants fend off colonization by phytopathogenic organisms. These specific interactions between the pathogen and the host determine the course of infection (Schopfer and Brennicke (1999) Pflanzenphysiologie, Springer Verlag, Berlin-Heidelberg, Germany).

With regard to the race specific resistance, also called host resistance, a differentiation is made between compatible and incompatible interactions. In the compatible interaction, an interaction occurs between a virulent pathogen and a susceptible plant. The pathogen survives, and may build up reproduction structures, while the host mostly dies off. An incompatible interaction occurs on the other hand when the pathogen infects the plant but is inhibited in its growth before or after weak development of symptoms. In the latter case, the plant is resistant to the respective pathogen (Schopfer and Brennicke, vide supra). However, this type of resistance is specific for a certain strain or pathogen.

In both compatible and incompatible interactions a defensive and specific reaction of the host to the pathogen occurs. In nature, however, this resistance is often overcome because of the rapid evolutionary development of new virulent races of the pathogens (Neu et al. (2003) American Cytopathol. Society, MPMI 16 No. 7: 626-633).

Most pathogens are plant-species specific. This means that a pathogen can induce a disease in a certain plant species, but not in other plant species (Heath (2002) Can. J. Plant Pathol. 24: 259-264). The resistance against a pathogen in certain plant species is called non-host resistance. The non-host resistance offers strong, broad, and permanent protection from phytopathogens. Genes providing non-host resistance provide the opportunity of a strong, broad and permanent protection against certain diseases in non-host plants. In particular, such a resistance works for different strains of the pathogen.

Fungi are distributed worldwide. Approximately 100 000 different fungal species are known to date. Thereof rusts are of great importance. They can have a complicated development cycle with up to five different spore stages (spermatium, aecidiospore, uredospore, teleutospore and basidiospore).

During the infection of plants by pathogenic fungi, different phases are usually observed. The first phases of the interaction between phytopathogenic fungi and their potential host plants are decisive for the colonization of the plant by the fungus. During the first stage of the infection, the spores become attached to the surface of the plants, germinate, and the fungus penetrates the plant. Fungi may penetrate the plant via existing ports such as stomata, lenticels, hydatodes and wounds, or else they penetrate the plant epidermis directly as the result of the mechanical force and with the aid of cell-wall-digesting enzymes. Specific infection structures are developed for penetration of the plant.

Immediately after recognition of a potential pathogen the plant starts to elicit defense reactions. Mostly the presence of the pathogen is sensed via so called PAMP receptors, a class of trans-membrane receptor like kinases recognizing conserved pathogen associated molecules (e.g. flagellin or chitin). Downstream of the PAMP receptors, the phytohormones salicylic acid (SA), jasmonate (JA) and ethylene (ET) play a critical role in the regulation of the different defense reactions. Depending on the ratio of the different phytohormones, different defense reactions are elicited by the host cell. Generally SA dependent defense is linked with resistance against biotrophic pathogens, whereas JA/ET dependent defense reactions are active against necrotrophic pathogens (and insects). In most plant pathogen interactions ET has been shown to act synergistic to JA and antagonistic to the “biotrophic” defense of SA. For example the well-known JA marker protein PDF1.2 needs the activation of both ET and JA to be up-regulated during defense against necrotrophic pathogens.

A protein which was known to be involved in the regulation of JA dependent defense responses against necrotrophic pathogens in *Arabidopsis thaliana* is the homeobox transcription factor Overexpressor of Cationic Peroxidase 3 (OCP3) (Coego A, Ramirez V, Gil M J, Flors V, Mauch-Mani B, Vera P: An *Arabidopsis* homeodomain transcription factor, Overexpressor Of Cationic Peroxidase 3, mediates resistance to infection by necrotrophic pathogens. Plant Cell 2005, 17(7):2123-2137).

The knock-out of OCP3 showed an enhanced resistance against necrotrophic pathogens, but in contrast to most other JA-defense modulating proteins no impairment in the defense against biotrophic pathogens. Therefore it was concluded that the expression of OCP3 inhibits a specific signaling cascade that is involved in JA mediated defense against necrotrophic fungi but not linked to SA mediated defenses against biotrophic fungi.

The soybean rust *Phakopsora pachyrhizi* directly penetrates the plant epidermis. After crossing the epidermal cell, the fungus reaches the intercellular space of the mesophyll, where the fungus starts to spread through the leaves. To acquire nutrients the fungus penetrates mesophyll cells and develops haustoria inside the mesophyl cell. During the penetration process the plasmamembrane of the penetrated mesophyll cell stays intact. Therefore the soybean rust fungus establishes a biotrophic interaction with soybean.

The biotrophic phytopathogenic fungi, such as soybean rust and all other rust fungi, depend for their nutrition on the metabolism of living cells of the plants. This type of fungi belong to the group of biotrophic fungi, like other rust fungi, powdery mildew fungi or oomycete pathogens like the genus *Phytophthora* or *Peronospora*. The necrotrophic phytopathogenic fungi depend for their nutrition on dead cells of the plants, e.g. species from the genus *Fusarium, Rhizoctonia* or *Mycospaerella*. Soybean rust has occupied an intermediate position, since it penetrates the epidermis directly, whereupon the penetrated cell becomes necrotic. After the penetration, the fungus changes over to an obligatory-biotrophic lifestyle. The subgroup of the biotrophic fungal pathogens which follows essentially such an infection strategy is heminecrotrohic. In contrast to a heminecrotrophic pathogen, a hemibiotrophic pathogen lives for a short period of time in a biotrophic manner and subsequently starts killing the host cell and/or host organism, i.e., changes for the rest of its life-cycle to a necrotrophic life-style.

Soybean rust has become increasingly important in recent times. The disease may be caused by the biotrophic rusts *Phakopsora pachyrhizi* (Sydow) and *Phakopsora meibomiae* (Arthur). They belong to the class Basidiomycota, order Uredinales, family Phakopsoraceae. Both rusts infect a wide spectrum of leguminosic host plants. *P. pachyrhizi*, also referred to as Asian rust, is the more aggressive pathogen on soy (*Glycine max*), and is therefore, at least currently, of great importance for agriculture. *P. pachyrhizi* can be found in nearly all tropical and subtropical soy growing regions of the world. *P. pachyrhizi* is capable of infecting 31 species from 17 families of the Leguminosae under natural conditions and is capable of growing on further 60 species under controlled conditions (Sinclair et al. (eds.), Proceedings of the rust workshop (1995), National SoyaResearch Laboratory, Publication No. 1 (1996); Rytter J. L. et al., Plant Dis. 87, 818 (1984)). *P. meibomiae* has been found in the Caribbean Basin and in Puerto Rico, and has not caused substantial damage as yet.

*P. pachyrhizi* can currently be controlled in the field only by means of fungicides. Soy plants with resistance to the entire spectrum of the isolates are not available. When searching for resistant plants, six dominant genes Rpp1-5 and Rpp?(Hyuuga), which mediate resistance of soy to *P. pachyrhizi*, were discovered. The resistance was lost rapidly, as *P. pychyrhizi* develops new virulent races.

In recent years, fungal diseases, e.g. soybean rust, has gained in importance as pest in agricultural production. There was therefore a demand in the prior art for developing methods to control fungi and to provide fungal resistant plants.

Much research has been performed on the field of powdery and downy mildew infecting the epidermal layer of plants. However, the problem to cope with soybean rust which infects the mesophyll remains unsolved.

The object of the present invention is inter alia to provide a method of increasing resistance against fungal pathogens, preferably rust pathogens (i.e., fungal pathogens of the order Pucciniales), preferably against fungal pathogens of the family Phacopsoraceae, more preferably against fungal pathogens of the genus *Phacopsora*, most preferably against *Phakopsora pachyrhizi* (Sydow) and *Phakopsora meibomiae* (Arthur), also known as soybean rust.

Surprisingly, we found that fungal pathogens, in particular rust pathogens (i.e., fungal pathogens of the order Pucciniales), preferably fungal pathogens of the family Phacopsoraceae, for example soybean rust, can be controlled by overexpression of an OCP3 protein. Thus, without being limited by theory, we found that fungal resistance can be achieved by expression of OCP3 and therefore enhancing the defense signaling towards resistance against biotrophic fungi.

The present invention therefore provides a method of increasing resistance against fungal pathogens, preferably rust pathogens (i.e., fungal pathogens of the order Pucciniales), preferably against fungal pathogens of the family Phacopsoraceae, more preferably against fungal pathogens of the genus *Phacopsora*, most preferably against *Phakopsora pachyrhizi* (Sydow) and *Phakopsora meibomiae* (Arthur), also known as soybean rust, in transgenic plants, transgenic plant parts, or transgenic plant cells by overexpressing one or more OCP3 nucleic acids.

A further object is to provide transgenic plants resistant against fungal pathogens, preferably rust pathogens (i.e., fungal pathogens of the order Pucciniales), preferably against fungal pathogens of the family Phacopsoraceae, more preferably against fungal pathogens of the genus *Phacopsora*, most preferably against *Phakopsora pachyrhizi* (Sydow) and *Phakopsora meibomiae* (Arthur), also known as soybean rust, a method for producing such plants as well as a vector construct useful for the above methods.

Therefore, the present invention also refers to a recombinant vector construct and a transgenic plant, transgenic plant part, or transgenic plant cell comprising an exogenous OCP3 nucleic acid. Furthermore, a method for the production of a transgenic plant, transgenic plant part or transgenic plant cell using the nucleic acid of the present invention is claimed herein. In addition, the use of a nucleic acid or the recombinant vector of the present invention for the transformation of a plant, plant part, or plant cell is claimed herein.

The objects of the present invention, as outlined above, are achieved by the subject-matter of the main claims. Preferred embodiments of the invention are defined by the subject matter of the dependent claims.

BRIEF SUMMARY OF THE INVENTION

The object of the present invention is inter alia to provide a method of increasing resistance against fungal pathogens, preferably against fungal pathogens of the family Phacopsoraceae, more preferably against fungal pathogens of the genus *Phacopsora*, most preferably against *Phakopsora pachyrhizi* (Sydow) and *Phakopsora meibomiae* (Arthur), also known as soybean rust.

Surprisingly, we found that fungal pathogens, in particular of the family Phacopsoraceae, for example soybean rust, can be controlled by overexpression of an OCP3 protein. Thus, without being limited by theory, we found that fungal resistance can be achieved by overexpression of OCP3 and therefore inhibiting the defense signaling towards resistance against necrotrophic fungi and/or enhancing the defense signaling towards resistance against biotrophic fungi.

The present invention therefore provides a method of increasing resistance against fungal pathogens, preferably against fungal pathogens of the family Phacopsoraceae, more preferably against fungal pathogens of the genus *Phacopsora*, most preferably against *Phakopsora pachyrhizi* (Sydow) and *Phakopsora meibomiae* (Arthur), also known as soybean rust, in transgenic plants, transgenic plant parts, or transgenic plant cells by overexpressing one or more OCP3 nucleic acids.

A further object is to provide transgenic plants resistant against fungal pathogens, preferably of the family Phacopsoraceae, more preferably against fungal pathogens of the genus *Phacopsora*, most preferably against *Phakopsora pachyrhizi* (Sydow) and *Phakopsora* meibomiae (Arthur), also known as soybean rust, a method for producing such plants as well as a vector construct useful for the above methods.

Therefore, the present invention also refers to a recombinant vector construct and a transgenic plant, transgenic plant part, or transgenic plant cell comprising an exogenous OCP3 nucleic acid. Furthermore, a method for the production of a transgenic plant, transgenic plant part or transgenic plant cell using the nucleic acid of the present invention is claimed herein. In addition, the use of a nucleic acid or the recombinant vector of the present invention for the transformation of a plant, plant part, or plant cell is claimed herein.

The objects of the present invention, as outlined above, are achieved by the subject-matter of the main claims. Preferred embodiments of the invention are defined by the subject matter of the dependent claims.

BRIEF DESCRIPTION OF THE SEVERAL VIEWS OF THE DRAWINGS

FIG. 1 shows the scoring system used to determine the level of diseased leaf area of wildtype and transgenic soy plants against the rust fungus *P. pachyrhizi*.

FIG. 2 shows the schematic illustration of the plant transformation vector harbouring the OCP3 cDNA under control of the epidermis specific promoter "GmEpidermis-specific promotor 670" as used in this invention.

FIG. 3 shows the full-length-sequence of the OCP3-gene from *Arabidopsis thaliana* as used in the present invention and having SEQ ID NO: 1.

FIG. 4 shows the sequence of the OCP3 protein (SEQ ID NO: 2).

FIG. 5 shows the sequence of the GmEpidermis-specific promotor 670 (derived from Glyma02g47670) as used in this invention (SEQ ID NO: 3).

FIG. 6 shows the result of the scoring of 33 transgenic soy plants expressing the OCP3 overexpression vector construct. $T_0$ soybean plants expressing OCP3 protein were inoculated with spores of *Phakopsora pachyrhizi*. The evaluation of the diseased leaf area on all leaves was performed 14 days after inoculation. The average of the percentage of the leaf area showing fungal colonies or strong yellowing/browning on all leaves was considered as diseased leaf area. At all 33 soybean $T_0$ plants expressing OCP3 (expression checked by RT-PCR) were evaluated in parallel to non-transgenic control plants. The average of the diseased leaf area is shown in FIG. 6. Overexpression of OCP3 significantly (**: $p<0.01$) reduces the diseased leaf area in comparison to non-transgenic control plants by 30.2%.

FIG. 7 contains a brief description of the sequences of the sequence listing.

DETAILED DESCRIPTION OF THE INVENTION

The present invention may be understood more readily by reference to the following detailed description of the preferred embodiments of the invention and the examples included herein.

Definitions

Unless otherwise noted, the terms used herein are to be understood according to conventional usage by those of ordinary skill in the relevant art. In addition to the definitions of terms provided herein, definitions of common terms in molecular biology may also be found in Rieger et al., 1991 Glossary of genetics: classical and molecular, 5th Ed., Berlin: Springer-Verlag; and in Current Protocols in Molecular Biology, F. M. Ausubel et al., Eds., Current Protocols, a joint venture between Greene Publishing Associates, Inc. and John Wiley & Sons, Inc., (1998 Supplement).

It is to be understood that as used in the specification and in the claims, "a" or "an" can mean one or more, depending upon the context in which it is used. Thus, for example, reference to "a cell" can mean that at least one cell can be utilized. It is to be understood that the terminology used herein is for the purpose of describing specific embodiments only and is not intended to be limiting.

Throughout this application, various publications are referenced. The disclosures of all of these publications and those references cited within those publications in their entireties are hereby incorporated by reference into this application in order to more fully describe the state of the art to which this invention pertains. Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in Sambrook et al., 1989 Molecular Cloning, Second Edition, Cold Spring Harbor Laboratory, Plainview, N.Y.; Maniatis et al., 1982 Molecular Cloning, Cold Spring Harbor Laboratory, Plainview, N.Y.; Wu (Ed.) 1993 Meth. Enzymol. 218, Part I; Wu (Ed.) 1979 Meth Enzymol. 68; Wu et al., (Eds.) 1983 Meth. Enzymol. 100 and 101; Grossman and Moldave (Eds.) 1980 Meth. Enzymol. 65; Miller (Ed.) 1972 Experiments in Molecular Genetics, Cold Spring Harbor Laboratory, Cold Spring Harbor, N.Y.; Old and Primrose, 1981 Principles of Gene Manipulation, University of California Press, Berkeley; Schleif and Wensink, 1982 Practical Methods in Molecular Biology; Glover (Ed.) 1985 DNA Cloning Vol. I and II, IRL Press, Oxford, UK; Hames and Higgins (Eds.) 1985 Nucleic Acid Hybridization, IRL Press, Oxford, UK; and Setlow and Hollaender 1979 Genetic Engineering: Principles and Methods, Vols. 1-4, Plenum Press, New York. Abbreviations and nomenclature, where employed, are deemed standard in the field and commonly used in professional journals such as those cited herein.

"Homologues" of a protein encompass peptides, oligopeptides, polypeptides, proteins and/or enzymes having amino acid substitutions, deletions and/or insertions relative to the unmodified protein in question and having similar functional activity as the unmodified protein from which they are derived.

"Homologues" of a nucleic acid encompass nucleotides and/or polynucleotides having nucleic acid substitutions, deletions and/or insertions relative to the unmodified nucleic acid in question, wherein the protein coded by such nucleic acids has similar or higher functional activity as the unmodified protein coded by the unmodified nucleic acid from which they are derived. In particular, homologues of a nucleic acid may encompass substitutions on the basis of the degenerative amino acid code.

A "deletion" refers to removal of one or more amino acids from a protein or to the removal of one or more nucleic acids from DNA, ssRNA and/or dsRNA.

An "insertion" refers to one or more amino acid residues or nucleic acid residues being introduced into a predetermined site in a protein or the nucleic acid.

A "substitution" refers to replacement of amino acids of the protein with other amino acids having similar properties (such as similar hydrophobicity, hydrophilicity, antigenicity, propensity to form or break α-helical structures or beta-sheet structures).

On the nucleic acid level a substitution refers to a replacement of nucleic acid with other nucleic acids, wherein the protein coded by the modified nucleic acid has a similar function. In particular homologues of a nucleic acid encompass substitutions on the basis of the degenerative amino acid code.

Amino acid substitutions are typically of single residues, but may be clustered depending upon functional constraints placed upon the protein and may range from 1 to 10 amino acids; insertions or deletion will usually be of the order of about 1 to 10 amino acid residues. The amino acid substitutions are preferably conservative amino acid substitutions. Conservative substitution tables are well known in the art (see for example Creighton (1984) Proteins. W.H. Freeman and Company (Eds) and Table 1 below; or Taylor W. R. (1986) The classification of amino acid conservation J Theor Biol., 119:205-18).

TABLE 1

Examples of conserved amino acid substitutions

| Residue | Conservative Substitutions |
|---|---|
| Ala | Ser |
| Arg | Lys |
| Asn | Gln; His |
| Asp | Glu |
| Gln | Asn |
| Cys | Ser |
| Glu | Asp |
| Gly | Pro |
| His | Asn; Gln |
| Ile | Leu, Val |
| Leu | Ile; Val |
| Lys | Arg; Gln |
| Met | Leu; Ile |
| Phe | Met; Leu; Tyr |
| Ser | Thr; Gly |
| Thr | Ser; Val |
| Trp | Tyr |
| Tyr | Trp; Phe |
| Val | Ile; Leu |

Amino acid substitutions, deletions and/or insertions may readily be made using peptide synthetic techniques well known in the art, such as solid phase peptide synthesis and the like, or by recombinant DNA manipulation.

Methods for the manipulation of DNA sequences to produce substitution, insertion or deletion variants of a protein are well known in the art. For example, techniques for making substitution mutations at predetermined sites in DNA are well known to those skilled in the art and include M13 mutagenesis, T7-Gene in vitro mutagenesis (USB, Cleveland, Ohio), QuickChange Site Directed mutagenesis (Stratagene, San Diego, Calif.), PCR-mediated site-directed mutagenesis or other site-directed mutagenesis protocols.

Orthologues and paralogues encompass evolutionary concepts used to describe the ancestral relationships of genes. Paralogues are genes within the same species that have originated through duplication of an ancestral gene; orthologues are genes from different organisms that have originated through speciation, and are also derived from a common ancestral gene.

The term "domain" refers to a set of amino acids conserved at specific positions along an alignment of sequences of evolutionarily related proteins. While amino acids at other positions can vary between homologues, amino acids that are highly conserved at specific positions indicate amino acids that are likely essential in the structure, stability or function of a protein.

Specialist databases exist for the identification of domains, for example, SMART (Schultz et al. (1998) Proc. Natl. Acad. Sci. USA 95, 5857-5864; Letunic et al. (2002) Nucleic Acids Res 30, 242-244), InterPro (Mulder et al., (2003) Nucl. Acids. Res. 31, 315-318), Prosite (Bucher and Bairoch (1994), A generalized profile syntax for biomolecular sequences motifs and its function in automatic sequence interpretation. (In) ISMB-94; Proceedings 2nd International Conference on Intelligent Systems for Molecular Biology. Altman R., Brutlag D., Karp P., Lathrop R., Searls D., Eds., pp 53-61, AAAI Press, Menlo Park; Hula et al., Nucl. Acids. Res. 32:D134-D137, (2004)), or Pfam (Bateman et al., Nucleic Acids Research 30(1): 276-280 (2002)). A set of tools for in silico analysis of protein sequences is available on the ExPASy proteomics server (Swiss Institute of Bioinformatics (Gasteiger et al., ExPASy: the proteomics server for in-depth protein knowledge and analysis, Nucleic Acids Res. 31:3784-3788(2003)). Domains or motifs may also be identified using routine techniques, such as by sequence alignment.

Methods for the alignment of sequences for comparison are well known in the art, such methods include GAP, BESTFIT, BLAST, FASTA and TFASTA. GAP uses the algorithm of Needleman and Wunsch ((1970) J Mol Biol 48: 443-453) to find the global (i.e. spanning the complete sequences) alignment of two sequences that maximizes the number of matches and minimizes the number of gaps. The BLAST algorithm (Altschul et al. (1990) J Mol Biol 215: 403-10) calculates percent sequence identity or similarity or homology and performs a statistical analysis of the identity or similarity or homology between the two sequences. The software for performing BLAST analysis is publicly available through the National Centre for Biotechnology Information (NCBI). Homologues may readily be identified using, for example, the ClustalW multiple sequence alignment algorithm (version 1.83), with the default pairwise alignment parameters, and a scoring method in percentage. Global percentages of similarity/homology/identity may also be determined using one of the methods available in the MatGAT software package (Campanella et al., BMC Bioinformatics. 2003 Jul. 10; 4:29. MatGAT: an application that generates similarity/homology/identity matrices using protein or DNA sequences.). Minor manual editing may be performed to optimise alignment between conserved motifs, as would be apparent to a person skilled in the art. Furthermore, instead of using full-length sequences for the identification of homologues, specific domains may also be used. The sequence identity values may be determined over the entire nucleic acid or amino acid sequence or over selected domains or conserved motif(s), using the programs mentioned above using the default parameters. For local alignments, the Smith-Waterman algorithm is particularly useful (Smith T F, Waterman M S (1981) J. Mol. Biol 147(1); 195-7).

As used herein the terms "fungal-resistance", "resistant to a fungus" and/or "fungal-resistant" mean reducing, preventing, or delaying an infection by fungi. The term "resistance" refers to fungal resistance. Resistance does not imply that the plant necessarily has 100% resistance to infection. In preferred embodiments, enhancing or increasing fungal resistance means that resistance in a resistant plant is greater than 10%, greater than 20%, greater than 30%, greater than 40%, greater than 50%, greater than 60%, greater than 70%, greater than 80%, greater than 90%, or greater than 95% in comparison to a wild type plant.

As used herein the terms "soybean rust-resistance", "resistant to a soybean rust", "soybean rust-resistant", "rust-resistance", "resistant to a rust", or "rust-resistant" mean reducing or preventing or delaying an infection of a plant, plant part, or plant cell by Phacopsoracea, in particular *Phakopsora pachyrhizi* (Sydow) and *Phakopsora meibomiae* (Arthur)—also known as soybean rust or Asian Soybean Rust (ASR), as compared to a wild type plant, wild type plant part, or wild type plant cell. Resistance does not imply that the plant necessarily has 100% resistance to infection. In preferred embodiments, enhancing or increasing rust resistance means that rust resistance in a resistant plant is greater than 10%, greater than 20%, greater than 30%, greater than 40%, greater than 50%, greater than 60%, greater than 70%, greater than 80%, greater than 90%, or greater than 95% in comparison to a wild type plant that is not resistant to soybean rust. Preferably the wild type plant is a plant of a similar, more preferably identical, genotype as the plant having increased resistance to the soybean rust, but does not comprise an exogenous OCP3 nucleic acid, functional fragments thereof and/or an exogenous nucleic acid capable of hybridizing with an OCP3 nucleic acid.

The level of fungal resistance of a plant can be determined in various ways, e.g. by scoring/measuring the infected leaf area in relation to the overall leaf area. Another possibility to determine the level of resistance is to count the number of soybean rust colonies on the plant or to measure the amount of spores produced by these colonies. Another way to resolve the degree of fungal infestation is to specifically measure the amount of rust DNA by quantitative (q) PCR. Specific probes and primer sequences for most fungal pathogens are available in the literature (Frederick R D, Snyder C L, Peterson G L, et al. 2002 Polymerase chain reaction assays for the detection and discrimination of the rust pathogens *Phakopsora pachyrhizi* and *P. meibomiae*, Phytopathology 92(2) 217-227).

The term "hybridization" as used herein includes "any process by which a strand of nucleic acid molecule joins with a complementary strand through base pairing" (J. Coombs (1994) Dictionary of Biotechnology, Stockton Press, New York). Hybridization and the strength of hybridization (i.e., the strength of the association between the nucleic acid molecules) is impacted by such factors as the degree of complementarity between the nucleic acid molecules, stringency of the conditions involved, the Tm of the formed hybrid, and the G:C ratio within the nucleic acid molecules.

As used herein, the term "Tm" is used in reference to the "melting temperature." The melting temperature is the temperature at which a population of double-stranded nucleic acid molecules becomes half dissociated into single strands. The equation for calculating the Tm of nucleic acid molecules is well known in the art. As indicated by standard references, a simple estimate of the Tm value may be calculated by the equation: Tm=81.5+0.41(% G+C), when a nucleic acid molecule is in aqueous solution at 1 M NaCl (see e.g., Anderson and Young, Quantitative Filter Hybridization, in Nucleic Acid Hybridization (1985). Other references include more sophisticated computations, which take structural as well as sequence characteristics into account for the calculation of Tm. Stringent conditions, are known to those skilled in the art and can be found in Current Protocols in Molecular Biology, John Wiley & Sons, N.Y. (1989), 6.3.1-6.3.6.

In particular, the term "stringency conditions" refers to conditions, wherein 100 contiguous nucleotides or more, 150 contiguous nucleotides or more, 200 contiguous nucleotides or more or 250 contiguous nucleotides or more which are a fragment or identical to the complementary nucleic acid molecule (DNA, RNA, ssDNA or ssRNA) hybridizes under conditions equivalent to hybridization in 7% sodium dodecyl sulfate (SDS), 0.5 M NaPO4, 1 mM EDTA at 50° C. with washing in 2×SSC, 0.1% SDS at 50° C. or 65° C., preferably at 65° C., with a specific nucleic acid molecule (DNA; RNA, ssDNA or ss RNA). Preferably, the hybridizing conditions are equivalent to hybridization in 7% sodium dodecyl sulfate (SDS), 0.5 M NaPO4, 1 mM EDTA at 50° C. with washing in 1×SSC, 0.1% SDS at 50° C. or 65° C., preferably 65° C., more preferably the hybridizing conditions are equivalent to hybridization in 7% sodium dodecyl sulfate (SDS), 0.5 M NaPO4, 1 mM EDTA at 50° C. with washing in 0.1×SSC, 0.1% SDS at 50° C. or 65° C., preferably 65° C. Preferably, the complementary nucleotides hybridize with a fragment or the whole OCP3 nucleic acids. Alternatively, preferred hybridization conditions encompass hybridisation at 65° C. in 1×SSC or at 42° C. in 1×SSC and 50% formamide, followed by washing at 65° C. in 0.3×SSC or hybridisation at 50° C. in 4×SSC or at 40° C. in 6×SSC and 50% formamide, followed by washing at 50° C. in 2×SSC. Further preferred hybridization conditions are 0.1% SDS, 0.1 SSD and 65° C.

"Identity" or "homology" or "similarity" between two nucleic acids sequences or amino acid sequences refers in each case over the entire length of the OCP3 nucleic acid sequences or OCP3 amino acid sequences. The terms "identity", "homology" and "similarity" are used herein interchangeably.

For example the identity may be calculated by means of the Vector NTI Suite 7.1 program of the company Informax (USA) employing the Clustal Method (Higgins D G, Sharp P M. Fast and sensitive multiple sequence alignments on a microcomputer. Comput Appl. Biosci. 1989 April; 5(2):151-1) with the following settings:

Multiple alignment parameter:

| | |
|---|---|
| Gap opening penalty | 10 |
| Gap extension penalty | 10 |

-continued

| | |
|---|---|
| Gap separation penalty range | 8 |
| Gap separation penalty | off |
| % identity for alignment delay | 40 |
| Residue specific gaps | off |
| Hydrophilic residue gap | off |
| Transition weighing | 0 |

Pairwise alignment parameter:

| | |
|---|---|
| FAST algorithm | on |
| K-tuple size | 1 |
| Gap penalty | 3 |
| Window size | 5 |
| Number of best diagonals | 5 |

Alternatively the identity may be determined according to Chenna, Ramu, Sugawara, Hideaki, Koike, Tadashi, Lopez, Rodrigo, Gibson, Toby J, Higgins, Desmond G, Thompson, Julie D. Multiple sequence alignment with the Clustal series of programs. (2003) Nucleic Acids Res 31 (13):3497-500, the web page: http://wvvw.ebi.ac.uk/Tools/clustalw/index.html# and the following settings

| | |
|---|---|
| DNA Gap Open Penalty | 15.0 |
| DNA Gap Extension Penalty | 6.66 |
| DNA Matrix | Identity |
| Protein Gap Open Penalty | 10.0 |
| Protein Gap Extension Penalty | 0.2 |
| Protein matrix | Gonnet |
| Protein/DNA ENDGAP | −1 |
| Protein/DNA GAPDIST | 4 |

All the nucleic acid sequences mentioned herein (single-stranded and double-stranded DNA and RNA sequences, for example cDNA and mRNA) can be produced in a known way by chemical synthesis from the nucleotide building blocks, e.g. by fragment condensation of individual overlapping, complementary nucleic acid building blocks of the double helix. Chemical synthesis of oligonucleotides can, for example, be performed in a known way, by the phosphoamidite method (Voet, Voet, 2nd edition, Wiley Press, New York, pages 896-897). The accumulation of synthetic oligonucleotides and filling of gaps by means of the Klenow fragment of DNA polymerase and ligation reactions as well as general cloning techniques are described in Sambrook et al. (1989), see below.

Sequence identity between the nucleic acid or protein useful according to the present invention and the OCP3 nucleic acids or OCP3 proteins may be optimized by sequence comparison and alignment algorithms known in the art (see Gribskov and Devereux, Sequence Analysis Primer, Stockton Press, 1991, and references cited therein) and calculating the percent difference between the nucleotide or protein sequences by, for example, the Smith-Waterman algorithm as implemented in the BESTFIT software program using default parameters (e.g., University of Wisconsin Genetic Computing Group).

The term "plant" is intended to encompass plants at any stage of maturity or development, as well as any tissues or organs (plant parts) taken or derived from any such plant unless otherwise clearly indicated by context. Plant parts include, but are not limited to, plant cells, stems, roots, flowers, ovules, stamens, seeds, leaves, embryos, meristematic regions, callus tissue, anther cultures, gametophytes, sporophytes, pollen, microspores, protoplasts, hairy root cultures, and/or the like. The present invention also includes seeds produced by the plants of the present invention. Preferably, the seeds comprise the exogenous OCP3 nucleic acids. In one embodiment, the seeds can develop into plants with increased resistance to fungal infection as compared to a wild-type variety of the plant seed. As used herein, a "plant cell" includes, but is not limited to, a protoplast, gamete producing cell, and a cell that regenerates into a whole plant. Tissue culture of various tissues of plants and regeneration of plants therefrom is well known in the art and is widely published.

Reference herein to an "endogenous" nucleic acid and/or protein refers to the nucleic acid and/or protein in question as found in a plant in its natural form (i.e., without there being any human intervention).

The term "exogenous" nucleic acid refers to a nucleic acid that has been introduced in a plant by means of genetechnology. An "exogenous" nucleic acid can either not occur in a plant in its natural form, be different from the nucleic acid in question as found in a plant in its natural form, or can be identical to a nucleic acid found in a plant in its natural form, but integrated not within their natural genetic environment. The corresponding meaning of "exogenous" is applied in the context of protein expression. For example, a transgenic plant containing a transgene, i.e., an exogenous nucleic acid, may, when compared to the expression of the endogenous gene, encounter a substantial increase of the expression of the respective gene or protein in total. A transgenic plant according to the present invention includes an exogenous OCP3 nucleic acid integrated at any genetic loci and optionally the plant may also include the endogenous gene within the natural genetic background.

For the purposes of the invention, "recombinant" means with regard to, for example, a nucleic acid sequence, a nucleic acid molecule, an expression cassette or a vector construct comprising any one or more OCP3 nucleic acids, all those constructions brought about by man by gentechnological methods in which either (a) the sequences of the OCP3 nucleic acids or a part thereof, or (b) genetic control sequence(s) which is operably linked with the OCP3 nucleic acid sequence according to the invention, for example a promoter, or (c) a) and b)

are not located in their natural genetic environment or have been modified by man by gentechnological methods. The modification may take the form of, for example, a substitution, addition, deletion, inversion or insertion of one or more nucleotide residues. The natural genetic environment is understood as meaning the natural genomic or chromosomal locus in the original plant or the presence in a genomic library or the combination with the natural promoter.

A recombinant nucleic acid may also refer to a nucleic acid in an isolated form. A recombinant nucleic acid, expression cassette or vector construct preferably comprises a natural gene and a natural promoter, a natural gene and a non-natural promoter, a non-natural gene and a natural promoter, or a non-natural gene and a non-natural promoter.

In the case of a genomic library, the natural genetic environment of the nucleic acid sequence is preferably retained, at least in part. The environment flanks the nucleic acid sequence at least on one side and has a sequence length of at least 50 bp, preferably at least 500 bp, especially preferably at least 1000 bp, most preferably at least 5000 bp.

A naturally occurring expression cassette—for example the naturally occurring combination of the natural promoter of the nucleic acid sequences with the corresponding nucleic acid sequence encoding a protein useful in the methods of the present invention, as defined above—becomes a recombinant expression cassette when this expression cassette is modified by man by non-natural, synthetic ("artificial") methods such as, for example, mutagenic treatment. Suitable methods are described, for example, in U.S. Pat. No. 5,565, 350, WO 00/15815 or US200405323. Furthermore, a naturally occurring expression cassette—for example the naturally occurring combination of the natural promoter of the nucleic acid sequences with the corresponding nucleic acid sequence encoding a protein useful in the methods of the present invention, as defined above—becomes a recombinant expression cassette when this expression cassette is not integrated in the natural genetic environment but in a different genetic environment.

It shall further be noted that in the context of the present invention, the term "isolated nucleic acid" or "isolated protein" may in some instances be considered as a synonym for a "recombinant nucleic acid" or a "recombinant protein", respectively and refers to a nucleic acid or protein that is not located in its natural genetic environment and/or that has been modified by genetechnical methods. The isolated gene may be isolated from an organism or may be manmade, for example by chemical synthesis.

As used herein, the term "transgenic" refers to an organism, e.g., a plant, plant cell, callus, plant tissue, or plant part that exogenously contains the nucleic acid, recombinant construct, vector or expression cassette described herein or a part thereof which is preferably introduced by non-essentially biological processes, preferably by Agrobacteria transformation. The recombinant construct or a part thereof is stably integrated into a chromosome, so that it is passed on to successive generations by clonal propagation, vegetative propagation or sexual propagation. Preferred successive generations are transgenic too. Essentially biological processes may be crossing of plants and/or natural recombination.

A transgenic plant, plants cell or tissue for the purposes of the invention is thus understood as meaning that an exogenous OCP3 nucleic acid, recombinant construct, vector or expression cassette including one or more OCP3 nucleic acids is integrated into the genome by means of genetechnology.

Preferably, constructs or vectors or expression cassettes are not present in the genome of the original plant or are present in the genome of the transgenic plant not at their natural locus of the genome of the original plant.

A "wild type" plant, "wild type" plant part, or "wild type" plant cell means that said plant, plant part, or plant cell does not express exogenous OCP3 nucleic acid or exogenous OCP3 protein.

Natural locus means the location on a specific chromosome, preferably the location between certain genes, more preferably the same sequence background as in the original plant which is transformed.

Preferably, the transgenic plant, plant cell or tissue thereof expresses the OCP3 nucleic acids, OCP3 constructs or OCP3 expression cassettes described herein.

The term "expression" or "gene expression" means the transcription of a specific gene or specific genes or specific genetic vector construct. The term "expression" or "gene expression" in particular means the transcription of a gene or genes or genetic vector construct into structural RNA (rRNA, tRNA), or mRNA with or without subsequent translation of the latter into a protein. The process includes transcription of DNA and processing of the resulting RNA product. The term "expression" or "gene expression" can also include the translation of the mRNA and therewith the synthesis of the encoded protein, i.e., protein expression.

The term "increased expression" or "enhanced expression" or "overexpression" or "increase of content" as used herein means any form of expression that is additional to the original wild-type expression level. For the purposes of this invention, the original wild-type expression level might also be zero (absence of expression).

Methods for increasing expression of genes or gene products are well documented in the art and include, for example, overexpression driven by appropriate promoters, the use of transcription enhancers or translation enhancers. Isolated nucleic acids which serve as promoter or enhancer elements may be introduced in an appropriate position (typically upstream) of a non-heterologous form of a polynucleotide so as to upregulate expression of a nucleic acid encoding the protein of interest. For example, endogenous promoters may be altered in vivo by mutation, deletion, and/or substitution (see, Kmiec, U.S. Pat. No. 5,565,350; Zarling et al., WO9322443), or isolated promoters may be introduced into a plant cell in the proper orientation and distance from a gene of the present invention so as to control the expression of the gene.

If protein expression is desired, it is generally desirable to include a polyadenylation region at the 3'-end of a polynucleotide coding region. The polyadenylation region can be derived from the natural gene, from a variety of other plant genes, or from T-DNA. The 3' end sequence to be added may be derived from, for example, the nopaline synthase or octopine synthase genes, or alternatively from another plant gene, or less preferably from any other eukaryotic gene.

An intron sequence may also be added to the 5' untranslated region (UTR) and/or the coding sequence of the partial coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold (Buchman and Berg (1988) Mol. Cell biol. 8: 4395-4405; Callis et al. (1987) Genes Dev 1:1183-1200). Such intron enhancement of gene expression is typically greatest when placed near the 5' end of the transcription unit. Use of the maize introns Adh1-S intron 1, 2, and 6, the Bronze-1 intron are known in the art. For general information see: The Maize Handbook, Chapter 116, Freeling and Walbot, Eds., Springer, N.Y. (1994).

The term "functional fragment" refers to any nucleic acid or protein which comprises merely a part of the full length nucleic acid or full length protein, respectively, but still provides the same function, e.g., fungal resistance, when expressed or repressed in a plant, respectively. Preferably, the fragment comprises at least 50%, at least 60%, at least 70%, at least 80%, at least 90% at least 95%, at least 98%, at least 99% of the original sequence. Preferably, the functional fragment comprises contiguous nucleic acids or amino acids as in the original nucleic acid or original protein, respectively. In one embodiment the fragment of any of the OCP3 nucleic acids has an identity as defined above over a length of at least 20%, at least 30%, at least 50%, at least 75%, at least 90% of the nucleotides of the respective OCP3 nucleic acid.

In cases where overexpression of nucleic acid is desired, the term "similar functional activity" or "similar function" means that any homologue and/or fragment provide fungal resistance when expressed in a plant. Preferably similar functional activity means at least 50%, at least 60%, at least 70%, at least 80%, at least 90%, at least 95%, at least 98%, at least 99% or 100% or higher fungal resistance compared with functional activity provided by the exogenous expression of the OCP3 nucleotide sequence as defined by SEQ ID NO: 1 or the OCP3 protein sequence as defined by SEQ ID NO: 2.

The term "increased activity" or "enhanced activity" as used herein means any protein having increased activity and which provides an increased fungal resistance compared with the wildtype plant merely expressing the respective endogenous OCP3 nucleic acid. As far as overexpression is concerned, for the purposes of this invention, the original wild-type expression level might also be zero (absence of expression).

With respect to a vector construct and/or the recombinant nucleic acid molecules, the term "operatively linked" is intended to mean that the nucleic acid to be expressed is linked to the regulatory sequence, including promoters, terminators, enhancers and/or other expression control elements (e.g., polyadenylation signals), in a manner which allows for expression of the nucleic acid (e.g., in a host plant cell when the vector is introduced into the host plant cell). Such regulatory sequences are described, for example, in Goeddel, Gene Expression Technology: Methods in Enzymology 185, Academic Press, San Diego, Calif. (1990) and Gruber and Crosby, in: Methods in Plant Molecular Biology and Biotechnology, Eds. Glick and Thompson, Chapter 7, 89-108, CRC Press: Boca Raton, Fla., including the references therein. Regulatory sequences include those that direct constitutive expression of a nucleotide sequence in many types of host cells and those that direct expression of the nucleotide sequence only in certain host cells or under certain conditions. It will be appreciated by those skilled in the art that the design of the vector can depend on such factors as the choice of the host cell to be transformed, the level of expression of nucleic acid desired, and the like.

The term "introduction" or "transformation" as referred to herein encompass the transfer of an exogenous polynucleotide into a host cell, irrespective of the method used for transfer. Plant tissue capable of subsequent clonal propagation, whether by organogenesis or embryogenesis, may be transformed with a vector construct of the present invention and a whole plant regenerated there from. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristem, axillary buds, and root meristems), and induced meristem tissue (e.g., cotyledon meristem and hypocotyl meristem). The polynucleotide may be transiently or stably introduced into a host cell and may be maintained non-integrated, for example, as a plasmid. Alternatively, it may be integrated into the host genome. The host genome includes the nucleic acid contained in the nucleus as well as the nucleic acid contained in the plastids, e.g., chloroplasts, and/or mitochondria. The resulting transformed plant cell may then be used to regenerate a transformed plant in a manner known to persons skilled in the art.

The term "terminator" encompasses a control sequence which is a DNA sequence at the end of a transcriptional unit which signals 3' processing and polyadenylation of a primary transcript and termination of transcription. The terminator can be derived from the natural gene, from a variety of other plant genes, or from T-DNA. The terminator to be added may be derived from, for example, the nopaline synthase or octopine synthase genes, or alternatively from another plant gene, or less preferably from any other eukaryotic gene.

DETAILED DESCRIPTION

OCP3 Nucleic Acids

The OCP3 nucleic acid to be overexpressed in order to achieve increased resistance to fungal pathogens, e.g., of the family Phacopsoraceae, for example soybean rust, is preferably a nucleic acid coding for an OCP3 protein, and is preferably as defined by SEQ ID NO: 1, 4-11, 12, 14, 16, 18, 20, 22, 24, or 26, or a fragment, homolog, derivative, orthologue or paralogue thereof. Preferably, the nucleic acid coding for an OCP3 protein of the present invention has at least 60% identity, preferably at least 70% sequence identity, at least 80%, at least 90%, at least 95%, at least 98%, at least 99% sequence identity, or even 100% sequence identity with SEQ ID NO: 1, 4-11, 12, 14, 16, 18, 20, 22, 24, or 26 or is a functional fragment thereof. Most preferred is at least 95% identity, more preferred is at least 98% or at least 99% identity with SEQ ID NO: 1, 4-11, 12, 14, 16, 18, 20, 22, 24, or 26.

The OCP3 nucleic acid to be overexpressed in order to achieve increased resistance to fungal pathogens, e.g., of the family Phacopsoraceae, for example soybean rust, is preferably a nucleic acid coding for an OCP3 protein, and is preferably as defined by SEQ ID NO: 1, or a fragment, homolog, derivative, orthologue or paralogue thereof. Preferably, the nucleic acid coding for an OCP3 protein of the present invention has at least 60% identity, preferably at least 70% sequence identity, at least 80%, at least 90%, at least 95%, at least 98%, at least 99% sequence identity, or even 100% sequence identity with SEQ ID NO: 1 or is a functional fragment thereof. Most preferred is at least 95% identity, more preferred is at least 98% or at least 99% identity with SEQ ID NO: 1.

Preferably the OCP3 nucleic acid is an isolated nucleic acid molecule comprising a nucleic acid selected from the group consisting of:

(i) a nucleic acid having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 1, 4-11, 12, 14, 16, 18, 20, 22, 24, or 26, or a functional fragment, derivative, orthologue, or paralogue thereof;

(ii) the complementary sequence of anyone of the nucleic acids of (i);

(iii) a nucleic acid encoding a OCP3 protein having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence represented by SEQ ID NO: 2, 13, 15, 17, 19, 21, 23, 25, or 27, or a functional fragment, derivative, orthologue, or paralogue thereof; preferably the OCP3 protein has essentially the same biological activity as an OCP3 protein encoded by SEQ ID NO: 2; preferably the OCP3 protein confers enhanced fungal resistance relative to control plants; and (iv) a nucleic acid molecule which hybridizes with a nucleic acid molecule of (i) to (iii) under high stringency hybridization conditions; and which preferably encodes a OCP3 protein that has essentially the same biological activity as an OCP3 protein encoded by SEQ ID NO: 2; preferably the encoded OCP3 protein confers enhanced fungal resistance relative to control plants;

(v) a nucleic acid encoding the same OCP3 protein as the OCP3 nucleic acids of (i) to (iv) above, but differing from the OCP3 nucleic acids of (i) to (iv) above due to the degeneracy of the genetic code.

Preferably the OCP3 nucleic acid is an isolated nucleic acid molecule comprising a nucleic acid selected from the group consisting of:

(i) a nucleic acid having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 1, or a functional fragment, derivative, orthologue, or paralogue thereof;

(ii) the complementary sequence of anyone of the nucleic acids of (i);

(iii) a nucleic acid encoding a OCP3 protein having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence represented by SEQ ID NO: 2, or a functional fragment, derivative, orthologue, or paralogue thereof; preferably the OCP3 protein has essentially the same biological activity as an OCP3 protein encoded by SEQ ID NO: 2; preferably the OCP3 protein confers enhanced fungal resistance relative to control plants; and (iv) a nucleic acid molecule which hybridizes with a nucleic acid molecule of (i) to (iii) under high stringency hybridization conditions; and which preferably encodes a OCP3 protein that has essentially the same biological activity as an OCP3 protein encoded by SEQ ID NO: 2; preferably the encoded OCP3 protein confers enhanced fungal resistance relative to control plants;

(v) a nucleic acid encoding the same OCP3 protein as the OCP3 nucleic acids of (i) to (iv) above, but differing from the OCP3 nucleic acids of (i) to (iv) above due to the degeneracy of the genetic code.

Percentages of identity of a nucleic acid are indicated with reference to the entire nucleotide region given in a sequence specifically disclosed herein.

Preferably, the OCP3 nucleic acid comprises at least about 100, at least about 200, at least about 300, at least about 400, at least about 500, at least about 600, at least about 700, at least about 800, at least about 850, at least about 900, at least about 950, at least about 975, at least about 990, at least about 1000, at least about 1025 or at least about 1050 nucleotides, preferably continuous nucleotides, preferably counted from the 5' or 3' end of the nucleic acid or up to the full length of the nucleic acid sequence set out in SEQ ID NO: 1, 4-11, 12, 14, 16, 18, 20, 22, 24, or 26.

Preferably the portion of the OCP3 nucleic acid is about 400-425, about 425-450, about 450-475, about 475-500, about 500-525, about 525-550, about 550-575, about 575-600, about 625-650, about 650-675, about 675-700, about 700-725, about 725-750, about 750-775, about 775-800, about 800-825, about 825-850, about 850-875, about 875-900, about 925-950, about 950-975, about 975-1000, about 1000-1025, or about 1025-1051 nucleotides, preferably consecutive nucleotides, preferably counted from the 5' or 3' end of the nucleic acid, in length, of the nucleic acid sequences given in SEQ ID NO: 1, 4-11, 12, 14, 16, 18, 20, 22, 24, or 26.

Preferably, the OCP3 nucleic acid comprises at least about 100, at least about 200, at least about 300, at least about 400, at least about 500, at least about 600, at least about 700, at least about 800, at least about 850, at least about 900, at least about 950, at least about 975, at least about 990, at least about 1000, at least about 1025 or at least about 1050 nucleotides, preferably continuous nucleotides, preferably counted from the 5' or 3' end of the nucleic acid or up to the full length of the nucleic acid sequence set out in SEQ ID NO: 1.

Preferably the portion of the OCP3 nucleic acid is about 400-425, about 425-450, about 450-475, about 475-500, about 500-525, about 525-550, about 550-575, about 575-600, about 625-650, about 650-675, about 675-700, about 700-725, about 725-750, about 750-775, about 775-800, about 800-825, about 825-850, about 850-875, about 875-900, about 925-950, about 950-975, about 975-1000, about 1000-1025, or about 1025-1051 nucleotides, preferably consecutive nucleotides, preferably counted from the 5' or 3' end of the nucleic acid, in length, of the nucleic acid sequences given in SEQ ID NO: 1.

The OCP3 nucleic acids described herein are useful in the constructs, methods, plants, harvestable parts and products of the invention.

OCP3 Proteins

The OCP3 protein is preferably defined by SEQ ID NO: 2, 13, 15, 17, 19, 21, 23, 25, or 27, or a fragment, homolog, derivative, orthologue or paralogue thereof. Preferably, the OCP3 protein of the present invention is encoded by a nucleic acid, which has at least 60% identity, preferably at least 70% sequence identity, at least 80%, at least 90%, at least 95%, at least 98%, at least 99% sequence identity, or even 100% sequence identity with SEQ ID NO: 1 or a functional fragment thereof. More preferably, the OCP3 protein of the present invention has at least 60%, preferably at least 70% sequence identity, at least 80%, at least 90%, at least 95%, at least 98%, at least 99% sequence identity, or even 100% sequence identity with SEQ ID NO: 2, 13, 15, 17, 19, 21, 23, 25, or 27, or is a functional fragment thereof, an orthologue or a paralogue thereof. Most preferred is at least 95% identity, more preferred is at least 98% or at least 99% identity with SEQ ID NO: 2, 13, 15, 17, 19, 21, 23, 25, or 27.

The OCP3 protein is preferably defined by SEQ ID NO: 2, or a fragment, homolog, derivative, orthologue or paralogue thereof. Preferably, the OCP3 protein of the present invention is encoded by a nucleic acid, which has at least 60% identity, preferably at least 70% sequence identity, at least 80%, at least 90%, at least 95%, at least 98%, at least 99% sequence identity, or even 100% sequence identity with SEQ ID NO: 1 or a functional fragment thereof. More preferably, the OCP3 protein of the present invention has at least 60%, preferably at least 70% sequence identity, at least 80%, at least 90%, at least 95%, at least 98%, at least 99% sequence identity, or even 100% sequence identity with SEQ ID NO: 2, or is a functional fragment thereof, an orthologue or a paralogue thereof. Most preferred is at least 95% identity, more preferred is at least 98% or at least 99% identity with SEQ ID NO: 2.

Preferably, the OCP3 protein is a protein comprising an amino acid sequence selected from the group consisting of:
(i) an amino acid sequence having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence represented by SEQ ID NO: 2, 13, 15, 17, 19, 21, 23, 25, or 27, or a functional fragment, derivative, orthologue, or paralogue thereof; preferably the OCP3 protein has essentially the same biological activity as an OCP3 protein encoded by SEQ ID NO: 2; preferably the OCP3 protein confers enhanced fungal resistance relative to control plants; or
(ii) an amino acid sequence encoded by a nucleic acid having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 1, 4-11, 12, 14, 16, 18, 20, 22, 24, or 26, or a functional fragment, derivative, orthologue, or paralogue thereof; preferably the OCP3 protein confers enhanced fungal resistance relative to control plants.

Preferably, the OCP3 protein is a protein comprising an amino acid sequence selected from the group consisting of:
(i) an amino acid sequence having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence represented by SEQ ID NO: 2, or a functional fragment, derivative, orthologue, or paralogue thereof; preferably the OCP3 protein has essentially the same biological activity as an OCP3 protein encoded by SEQ ID NO: 2; preferably the OCP3 protein confers enhanced fungal resistance relative to control plants; or
(ii) an amino acid sequence encoded by a nucleic acid having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 1, or a functional fragment, derivative, orthologue, or paralogue thereof; preferably the OCP3 protein confers enhanced fungal resistance relative to control plants.

Percentages of identity of a polypeptide or protein are indicated with reference to the entire amino acid sequence specifically disclosed herein.

Preferably, the OCP3 protein comprises at least about 50, at least about 75, at least about 100, at least about 125, at least about 150, at least about 175, at least about 200, at least about 225, at least about 250, at least about 275, at least about 300, at least about 310, at least about 320, at least about 325, at least about 330, at least about 335, at least about 340, at least about 345, or at least about 350 amino acid residues, preferably continuous amino acid residues, preferably counted from the N-terminus or the C-terminus of the amino acid sequence, or up to the full length of the amino acid sequence set out in SEQ ID NO: 2, 13, 15, 17, 19, 21, 23, 25, or 27.

Preferably, the OCP3 polypeptide comprises about 125-150, about 150-175, about 175-200, about 200-225, about 225-250, about 250-275, about 275-300, about 300-325, about 325-335, about 335-345, or about 345-354 amino acids, preferably consecutive amino acids, preferably counted from the N-terminus or C-terminus of the amino acid sequence, or up to the full length of any of the amino acid sequences encoded by the nucleic acid sequences set out in SEQ ID NO: 2, 13, 15, 17, 19, 21, 23, 25, or 27.

Preferably, the OCP3 protein comprises at least about 50, at least about 75, at least about 100, at least about 125, at least about 150, at least about 175, at least about 200, at least about 225, at least about 250, at least about 275, at least about 300, at least about 310, at least about 320, at least about 325, at least about 330, at least about 335, at least about 340, at least about 345, or at least about 350 amino acid residues, preferably continuous amino acid residues, preferably counted from the N-terminus or the C-terminus of the amino acid sequence, or up to the full length of the amino acid sequence set out in SEQ ID NO: 2.

Preferably, the OCP3 polypeptide comprises about 125-150, about 150-175, about 175-200, about 200-225, about 225-250, about 250-275, about 275-300, about 300-325, about 325-335, about 335-345, or about 345-354 amino acids, preferably consecutive amino acids, preferably counted from the N-terminus or C-terminus of the amino acid sequence, or up to the full length of any of the amino acid sequences encoded by the nucleic acid sequences set out in SEQ ID NO: 2.

The OCP3 proteins described herein are useful in the constructs, methods, plants, harvestable parts and products of the invention.

Methods for Increasing Fungal Resistance; Methods for Modulating Gene Expression One embodiment of the invention is a method for increasing fungal resistance, preferably resistance to Phacopsoracea, for example soy bean rust, in a plant, plant part, or plant cell by increasing the expression of an OCP3 protein or a functional fragment, orthologue, paralogue or homologue thereof in comparison to wild-type plants, wild-type plant parts or wild-type plant cells.

The present invention also provides a method for increasing resistance to fungal pathogens, in particular fungal pathogens of the family Phacopsoraceae, preferably against fungal pathogens of the genus *Phacopsora*, most preferably against *Phakopsora pachyrhizi* (Sydow) and *Phakopsora meibomiae* (Arthur), also known as soy bean rust in plants or plant cells, wherein in comparison to wild type plants, wild type plant parts, or wild type plant cells an OCP3 protein is overexpressed.

The present invention further provides a method for increasing resistance to fungal pathogens of the genus *Phacopsora*, most preferably against *Phakopsora pachyrhizi* (Sydow) and *Phakopsora meibomiae* (Arthur), also known as soy bean rust in plants or plant cells by overexpression of an OCP3 protein.

In preferred embodiments, the protein amount and/or function of the OCP3 protein in the plant is increased by at least 10%, at least 20%, at least 30%, at least 40%, at least 50%, at least 60%, at least 70%, at least 80%, at least 90%, or at least 95% or more in comparison to a wild type plant that is not transformed with the OCP3 nucleic acid.

In one embodiment of the invention, the OCP3 protein is encoded by (i) an exogenous nucleic acid having at least 60%, preferably at least 70%, for example at least 75%, more preferably at least 80%, for example at least 85%, even more preferably at least 90%, for example at least 95% or at least 96% or at least 97% or at least 98% most preferably 99% identity with SEQ ID NO: 1, a functional fragment thereof, or an orthologue or a paralogue thereof; or by (ii) an exogenous nucleic acid encoding a protein having at least 60% identity, preferably at least 70%, for example at least 75%, more preferably at least 80%, for example at least 85%, even more preferably at least 90%, for example at least 95% or at least 96% or at least 97% or at least 98% most preferably 99% homology with SEQ ID NO: 2, a functional fragment thereof, an orthologue or a paralogue thereof, preferably the encoded protein confers enhanced fungal resistance relative to control plants;

(iii) an exogenous nucleic acid capable of hybridizing under stringent conditions with any of the nucleic acids according to (i) or (ii) or a complementary sequence (complement) thereof, and which preferably encodes a OCP3 protein that has essentially the same biological activity as an OCP3 protein encoded by SEQ ID NO: 2; preferably the encoded OCP3 protein confers enhanced fungal resistance relative to control plants, and/or by (iv) an exogenous nucleic acid encoding the same OCP3 protein as the nucleic acids of (i) to (iii) above, but differing from the nucleic acids of (i) to (iii) above due to the degeneracy of the genetic code.

A method for increasing fungal resistance, preferably resistance to Phacopsoracea, for example soy bean rust, in a plant, plant part, or plant cell, by increasing the expression of an OCP3 protein or a functional fragment, orthologue, paralogue or homologue thereof wherein the OCP3 protein is encoded by (i) an exogenous nucleic acid having at least 60% identity, preferably at least 70% sequence identity, at least 80%, at least 90%, at least 95%, at least 98%, at least 99% sequence identity, or even 100% sequence identity with SEQ ID NO: 1, 4-11, 12, 14, 16, 18, 20, 22, 24, or 26 or a functional fragment thereof, an orthologue or a paralogue thereof;

(ii) an exogenous nucleic acid encoding a protein having at least 60%, preferably at least 70% sequence identity, at least 80%, at least 90%, at least 95%, at least 98%, at least 99% sequence identity, or even 100% sequence identity with SEQ ID NO: 2, 13, 15, 17, 19, 21, 23, 25, or 27, a functional fragment thereof, an orthologue or a paralogue thereof; preferably the encoded protein confers enhanced fungal resistance relative to control plants;

(iii) an exogenous nucleic acid capable of hybridizing under stringent conditions with any of the nucleic acids according to (i) or (ii) or a complement thereof, and which preferably encodes a OCP3 protein that has essentially the same biological activity as an OCP3 protein encoded by SEQ ID NO: 2; preferably the encoded OCP3 protein confers enhanced fungal resistance relative to control plants; and/or by (iv) an exogenous nucleic acid encoding the same OCP3 protein as the nucleic acids of (i) to (iii) above, but differing from the nucleic acids of (i) to (iii) above due to the degeneracy of the genetic code, is a further embodiment of the invention.

A method for increasing fungal resistance, preferably resistance to Phacopsoracea, for example soy bean rust, in a plant, plant part, or plant cell, by increasing the expression of an OCP3 protein or a functional fragment, orthologue, paralogue or homologue thereof wherein the OCP3 protein is encoded by (i) an exogenous nucleic acid having at least 60% identity, preferably at least 70% sequence identity, at least 80%, at least 90%, at least 95%, at least 98%, at least 99% sequence identity, or even 100% sequence identity with SEQ ID NO: 1 or a functional fragment thereof, an orthologue or a paralogue thereof;

(ii) an exogenous nucleic acid encoding a protein having at least 60%, preferably at least 70% sequence identity, at least 80%, at least 90%, at least 95%, at least 98%, at least 99% sequence identity, or even 100% sequence identity with SEQ ID NO: 2, a functional fragment thereof, an orthologue or a paralogue thereof; preferably the encoded protein confers enhanced fungal resistance relative to control plants;

(iii) an exogenous nucleic acid capable of hybridizing under stringent conditions with any of the nucleic acids according to (i) or (ii) or a complement thereof, and which preferably encodes a OCP3 protein that has essentially the same biological activity as an OCP3 protein encoded by SEQ ID NO: 2; preferably the encoded OCP3 protein confers enhanced fungal resistance relative to control plants; and/or by (iv) an exogenous nucleic acid encoding the same OCP3 protein as the nucleic acids of (i) to (iii) above, but differing from the nucleic acids of (i) to (iii) above due to the degeneracy of the genetic code, is a further embodiment of the invention.

In a further method of the invention, the method comprises the steps of
(a) stably transforming a plant cell with a recombinant expression cassette comprising
   (i) a nucleic acid having at least 60% identity, preferably at least 70% sequence identity, at least 80%, at least 90%, at least 95%, at least 98%, at least 99% sequence identity, or even 100% sequence identity with SEQ ID NO: 1, 4-11, 12, 14, 16, 18, 20, 22, 24, or 26 or a functional fragment thereof, or an orthologue or a paralogue thereof;
   (ii) a nucleic acid coding for a protein having at least 60% identity, preferably at least 70% sequence identity, at least 80%, at least 90%, at least 95%, at least 98%, at least 99% sequence identity, or even 100% sequence identity with SEQ ID NO: 2, a functional fragment thereof, an orthologue or a paralogue thereof; preferably the encoded protein confers enhanced fungal resistance relative to control plants;
   (iii) a nucleic acid capable of hybridizing under stringent conditions with any of the nucleic acids according to (i) or (ii) or a complement thereof, and which preferably encodes a OCP3 protein that has essentially the same biological activity as an OCP3 protein encoded by SEQ ID NO: 2, 13, 15, 17, 19, 21, 23, 25, or 27; preferably the encoded OCP3 protein confers enhanced fungal resistance relative to control plants; and/or
   (iv) an exogenous nucleic acid encoding the same OCP3 polypeptide as the nucleic acids of (i) to (iii) above, but differing from the nucleic acids of (i) to (iii) above due to the degeneracy of the genetic code, in functional linkage with a promoter;
(b) regenerating the plant from the plant cell; and
(c) expressing said nucleic acid, optionally wherein the nucleic acid which codes for an OCP3 protein is expressed in an amount and for a period sufficient to generate or to increase soybean rust resistance in said plant.

In a further method of the invention, the method comprises the steps of
(a) stably transforming a plant cell with a recombinant expression cassette comprising
   (i) a nucleic acid having at least 60% identity, preferably at least 70% sequence identity, at least 80%, at least 90%, at least 95%, at least 98%, at least 99% sequence identity, or even 100% sequence identity with SEQ ID NO: 1 or a functional fragment thereof, or an orthologue or a paralogue thereof;
  (ii) a nucleic acid coding for a protein having at least 60% identity, preferably at least 70% sequence identity, at least 80%, at least 90%, at least 95%, at least 98%, at least 99% sequence identity, or even 100% sequence identity with SEQ ID NO: 2, a functional fragment thereof, an orthologue or a paralogue thereof; preferably the encoded protein confers enhanced fungal resistance relative to control plants;
  (iii) a nucleic acid capable of hybridizing under stringent conditions with any of the nucleic acids according to (i) or (ii) or a complement thereof, and which preferably encodes a OCP3 protein that has essentially the same biological activity as an OCP3 protein encoded by SEQ ID NO: 2; preferably the encoded OCP3 protein confers enhanced fungal resistance relative to control plants; and/or
  (iv) an exogenous nucleic acid encoding the same OCP3 polypeptide as the nucleic acids of (i) to (iii) above, but differing from the nucleic acids of (i) to (iii) above due to the degeneracy of the genetic code,
in functional linkage with a promoter;
(b) regenerating the plant from the plant cell; and
(c) expressing said nucleic acid, optionally wherein the nucleic acid which codes for an OCP3 protein is expressed in an amount and for a period sufficient to generate or to increase soybean rust resistance in said plant.

A preferred embodiment is a method for increasing resistance to soy bean rust in a soy bean plant, soy bean plant part, or soy bean plant cell, by increasing the expression of an OCP3 protein, wherein the OCP3 protein is encoded by
(i) an exogenous nucleic acid having at least 95%, at least 98%, at least 99% sequence identity, or even 100% sequence identity with SEQ ID NO: 1;
(ii) an exogenous nucleic acid encoding a protein having at least 95%, at least 98%, at least 99% sequence identity, or even 100% sequence identity with SEQ ID NO: 2; preferably the encoded protein confers enhanced fungal resistance relative to control plants;
(iii) an exogenous nucleic acid capable of hybridizing under stringent conditions with any of the nucleic acids according to (i) or (ii) or a complement thereof, and which preferably encodes a OCP3 protein that has essentially the same biological activity as an OCP3 protein encoded by SEQ ID NO: 2; preferably the encoded OCP3 protein confers enhanced fungal resistance relative to control plants; and/or by
(iv) an exogenous nucleic acid encoding the same OCP3 protein as the nucleic acids of (i) to (iii) above, but differing from the nucleic acids of (i) to (iii) above due to the degeneracy of the genetic code,
wherein increasing the expression of the OCP3 protein is achieved by transforming the soy bean plant, plant part or plant cell with a nucleic acid comprising the nucleic acid set out under item (i) or (ii) or (iii) or (iv).

Also a preferred embodiment is a method for increasing resistance to soy bean rust in a soy bean plant, soy bean plant part, or soy bean plant cell, by increasing the expression of an OCP3 protein, wherein the OCP3 protein is encoded by
(i) an exogenous nucleic acid having at least 95%, at least 98%, at least 99% sequence identity, or even 100% sequence identity with SEQ ID NO: 1;
(ii) an exogenous nucleic acid encoding a protein having at least 95%, at least 98%, at least 99% sequence identity, or even 100% sequence identity with SEQ ID NO: 2; preferably the encoded protein confers enhanced fungal resistance relative to control plants; or
(iii) an exogenous nucleic acid encoding the same OCP3 protein as the nucleic acids of (i) to (ii) above, but differing from the nucleic acids of (i) to (ii) above due to the degeneracy of the genetic code,
wherein increasing the expression of the OCP3 protein is achieved by transforming the soy bean plant, plant part or plant cell with a nucleic acid comprising the nucleic acid set out under item (i) or (ii) or (iii).

The fungal pathogens or fungus-like pathogens (such as, for example, Chromista) can belong to the group comprising Plasmodiophoramycota, Oomycota, Ascomycota, Chytridiomycetes, Zygomycetes, Basidiomycota or Deuteromycetes (Fungi imperfecti). Pathogens which may be mentioned by way of example, but not by limitation, are those detailed in Tables 2 and 3, and the diseases which are associated with them.

TABLE 2

Diseases caused by biotrophic and/or heminecrotrophic phytopathogenic fungi

| Disease | Pathogen |
| --- | --- |
| Leaf rust | *Puccinia recondita* |
| Yellow rust | *P. striiformis* |
| Powdery mildew | *Erysiphe graminis/Blumeria graminis* |
| Rust (common corn) | *Puccinia sorghi* |
| Rust (Southern corn) | *Puccinia polysora* |
| Tobacco leaf spot | *Cercospora nicotianae* |
| Rust (soybean) | *Phakopsora pachyrhizi, P. meibomiae* |
| Rust (tropical corn) | *Physopella pallescens, P. zeae = Angiopsora zeae* |

TABLE 3

Diseases caused by necrotrophic and/or hemibiotrophic fungi and Oomycetes

| Disease | Pathogen |
| --- | --- |
| Plume blotch | *Septoria (Stagonospora) nodorum* |
| Leaf blotch | *Septoria tritici* |
| Ear fusarioses | *Fusarium* spp. |
| Late blight | *Phytophthora infestans* |
| Anthrocnose leaf blight | *Colletotrichum graminicola* (teleomorph: *Glomerella graminicola* Politis); *Glomerella tucumanensis* (anamorph: *Glomerella falcatum* Went) |
| Anthracnose stalk rot | |
| *Curvularia* leaf spot | *Curvularia clavata, C. eragrostidis, = C. maculans* (teleomorph: *Cochliobolus eragrostidis*), *Curvularia inaequalis, C. intermedia* (teleomorph: *Cochliobolus intermedius*), *Curvularia lunata* (teleomorph: *Cochliobolus lunatus*), *Curvularia pallescens* (teleomorph: *Cochliobolus pallescens*), *Curvularia senegalensis, C. tuberculata* (teleomorph: *Cochliobolus tuberculatus*) |
| *Didymella* leaf spot | *Didymella exitalis* |
| *Diplodia* leaf spot or streak | *Stenocarpella macrospora = Diplodialeaf macrospora* |
| Brown stripe downy mildew | *Sclerophthora rayssiae* var. *zeae* |
| Crazy top downy mildew | *Sclerophthora macrospora = Sclerospora macrospora* |
| Green ear downy mildew (*graminicola* downy mildew) | *Sclerospora graminicola* |
| Leaf spots, minor | *Alternaria alternata, Ascochyta maydis, A. tritici, A. zeicola, Bipolaris victoriae = Helminthosporium victoriae* (teleomorph: *Cochliobolus victoriae*), *C. sativus* (anamorph: *Bipolaris sorokiniana = H. sorokinianum = H. sativum*), *Epicoccum nigrum, Exserohilum prolatum = Drechslera prolata* (teleomorph: *Setosphaeria prolata*) *Graphium penicillioides, Leptosphaeria maydis, Leptothyrium zeae, Ophiosphaerella herpotricha*, (anamorph: *Scolecosporiella* sp.), *Paraphaeosphaeria michotii, Phoma* sp., *Septoria zeae, S. zeicola, S. zeina* |
| Northern corn leaf blight (white blast, crown stalk rot, stripe) | *Setosphaeria turcica* (anamorph: *Exserohilum turcicum = Helminthosporium turcicum*) |
| Northern corn leaf spot *Helminthosporium* ear rot (race 1) | *Cochliobolus carbonum* (anamorph: *Bipolaris zeicola = Helminthosporium carbonum*) |
| *Phaeosphaeria* leaf spot | *Phaeosphaeria maydis = Sphaerulina maydis* |
| Rostratum leaf spot (*Helminthosporium* leaf disease, ear and stalk rot) | *Setosphaeria rostrata*, (anamorph: *xserohilum rostratum = Helminthosporium rostratum*) |
| Java downy mildew | *Peronosclerospora maydis = Sclerospora maydis* |
| Philippine downy mildew | *Peronosclerospora philippinensis = Sclerospora philippinensis* |
| *Sorghum* downy mildew | *Peronosclerospora sorghi = Sclerospora sorghi* |
| *Spontaneum* downy mildew | *Peronosclerospora spontanea = Sclerospora spontanea* |
| Sugarcane downy mildew | *Peronosclerospora sacchari = Sclerospora sacchari* |
| Sclerotium ear rot (southern blight) | *Sclerotium rolfsii* Sacc. (teleomorph: *Athelia rolfsii*) |
| Seed rot-seedling blight | *Bipolaris sorokiniana, B. zeicola = Helminthosporium carbonum, Diplodia maydis, Exserohilum pedicillatum, Exserohilum turcicum = Helminthosporium turcicum, Fusarium avenaceum, F. culmorum, F. moniliforme, Gibberella zeae* (anamorph: *F. graminearum*), *Macrophomina phaseolina, Penicillium* spp., *Phomopsis* sp., *Pythium* spp., *Rhizoctonia solani, R. zeae, Sclerotium rolfsii, Spicaria* sp. |
| *Selenophoma* leaf spot | *Selenophoma* sp. |
| Yellow leaf blight | *Ascochyta ischaemi, Phyllosticta maydis* (teleomorph: *Mycosphaerella zeae-maydis*) |
| Zonate leaf spot | *Gloeocercospora sorghi* |

The following are especially preferred:

Plasmodiophoromycota such as *Plasmodiophora brassicae* (clubroot of crucifers), *Spongospora subterranea, Polymyxa graminis,*

Oomycota such as *Bremia lactucae* (downy mildew of lettuce), *Peronospora* (downy mildew) in snapdragon (*P. antirrhini*), onion (*P. destructor*), spinach (*P. effusa*), soybean (*P. manchurica*), tobacco ("blue mold"; *P. tabacina*) alfalfa and clover (*P. trifolium*), *Pseudoperonospora humuli* (downy mildew of hops), *Plasmopara* (downy mildew in grapevines) (*P. viticola*) and sunflower (*P. halstedii*), *Sclerophthora macrospora* (downy mildew in cereals and grasses), *Pythium* (for example damping-off of Beta beet caused by *P. debaryanum*), *Phytophthora infestans* (late blight in potato and in tomato and the like), *Albugo* spec.

Ascomycota such as *Microdochium nivale* (snow mold of rye and wheat), *Fusarium, Fusarium graminearum, Fusarium culmorum* (partial ear sterility mainly in wheat), *Fusarium oxysporum* (*Fusarium* wilt of tomato), *Blumeria graminis* (powdery mildew of barley (f.sp *hordei*) and wheat (f.sp. *tritici*)), *Erysiphe pisi* (powdery mildew of pea), *Nectria galligena* (*Nectria* canker of fruit trees), *Uncinula necator* (powdery mildew of grapevine), *Pseudopeziza tracheiphila* (red fire disease of grapevine), *Claviceps purpurea* (ergot on, for example, rye and grasses), *Gaeumannomyces graminis* (take-all on wheat, rye and other grasses), *Magnaporthe grisea, Pyrenophora graminea* (leaf stripe of barley), *Pyrenophora teres* (net blotch of barley), *Pyrenophora tritici-repentis* (leaf blight of wheat), *Venturia inaequalis* (apple scab), *Sclerotinia sclerotium* (stalk break, stem rot), *Pseudopeziza medicaginis* (leaf spot of alfalfa, white and red clover).

Basidiomycetes such as *Typhula incarnata* (*typhula* blight on barley, rye, wheat), *Ustilago maydis* (blister smut on maize), *Ustilago nuda* (loose smut on barley), *Ustilago tritici* (loose smut on wheat, spelt), *Ustilago avenae* (loose smut on oats), *Rhizoctonia solani* (*rhizoctonia* root rot of potato), *Sphacelotheca* spp. (head smut of sorghum), *Melampsora lini* (rust of flax), *Puccinia graminis* (stem rust of wheat, barley, rye, oats), *Puccinia recondita* (leaf rust on wheat), *Puccinia dispersa* (brown rust on rye), *Puccinia hordei* (leaf rust of barley), *Puccinia coronata* (crown rust of oats), *Puccinia striiformis* (yellow rust of wheat, barley, rye and a large number of grasses), *Uromyces appendiculatus* (brown rust of bean), *Sclerotium rolfsii* (root and stem rots of many plants).

Deuteromycetes (Fungi imperfecti) such as *Septoria* (*Stagonospora*) *nodorum* (glume blotch) of wheat (*Septoria tritici*), *Pseudocercosporella herpotrichoides* (eyespot of wheat, barley, rye), *Rynchosporium secalis* (leaf spot on rye and barley), *Alternaria solani* (early blight of potato, tomato), *Phoma betae* (blackleg on Beta beet), *Cercospora beticola* (leaf spot on Beta beet), *Alternaria brassicae* (black spot on oilseed rape, cabbage and other crucifers), *Verticillium dahliae* (*verticillium* wilt), *Colletotrichum, Colletotrichum lindemuthianum* (bean anthracnose), *Phoma lingam* (blackleg of cabbage and oilseed rape), *Botrytis cinerea* (grey mold of grapevine, strawberry, tomato, hops and the like).

Especially preferred are biotrophic pathogens, e.g., *Phakopsora pachyrhizi* and/or those pathogens which have essentially a similar infection mechanism as *Phakopsora pachyrhizi*, as described herein. Particularly preferred are pathogens from the subclass Pucciniomycetes, preferably from the order Pucciniales (rust), previously known as Uredinales, among which in particular the Melompsoraceae. Preferred are Phakopsoraceae, more preferably *Phakopsora*. Especially preferred are *Phakopsora pachyrhizi* and/or *Phakopsora* meibomiae.

Also preferred rust fungi are selected from the group of *Puccinia, Gymnosporangium, Juniperus, Cronartium, Hemileia*, and *Uromyces*; preferably *Puccinia sorghi, Gymnosporangium juniperi-virginianae, Juniperus virginiana, Cronartium ribicola, Hemileia vastatrix; Puccinia graminis, Puccinia coronata, Uromyces phaseoli, Puccinia hemerocallidis, Puccinia persistens* subsp. *Triticina, Puccinia striiformis, Puccinia graminis* causes, and/or *Uromyces appendeculatus.*

OCP3 Expression Constructs and Vector Constructs

A recombinant vector construct comprising:

(a) (i) a nucleic acid having at least 60% identity, preferably at least 70% sequence identity, at least 80%, at least 90%, at least 95%, at least 98%, at least 99% sequence identity, or even 100% sequence identity with SEQ ID NO: 1, 4-11, 12, 14, 16, 18, 20, 22, 24, or 26, or a functional fragment thereof, or an orthologue or a paralogue thereof;

(ii) a nucleic acid coding for a protein having at least 60% identity, preferably at least 70% sequence identity, at least 80%, at least 90%, at least 95%, at least 98%, at least 99% sequence identity, or even 100% sequence identity with SEQ ID NO: 2, 13, 15, 17, 19, 21, 23, 25, or 27, a functional fragment thereof, an orthologue or a paralogue thereof; preferably the encoded protein confers enhanced fungal resistance relative to control plants;

(iii) a nucleic acid capable of hybridizing under stringent conditions with any of the nucleic acids according to (i) or (ii) or a complement thereof, and which preferably encodes a OCP3 protein that has essentially the same biological activity as an OCP3 protein encoded by SEQ ID NO: 2; preferably the encoded OCP3 protein confers enhanced fungal resistance relative to control plants; and/or (iv) a nucleic acid encoding the same OCP3 protein as the nucleic acids of (i) to (iii) above, but differing from the nucleic acids of (i) to (iii) above due to the degeneracy of the genetic code, operably linked with (b) a promoter and (c) a transcription termination sequence is a further embodiment of the invention.

A recombinant vector construct comprising:

(a) (i) a nucleic acid having at least 60% identity, preferably at least 70% sequence identity, at least 80%, at least 90%, at least 95%, at least 98%, at least 99% sequence identity, or even 100% sequence identity with SEQ ID NO: 1 or a functional fragment thereof, or an orthologue or a paralogue thereof;

(ii) a nucleic acid coding for a protein having at least 60% identity, preferably at least 70% sequence identity, at least 80%, at least 90%, at least 95%, at least 98%, at least 99% sequence identity, or even 100% sequence identity with SEQ ID NO: 2, a functional fragment thereof, an orthologue or a paralogue thereof; preferably the encoded protein confers enhanced fungal resistance relative to control plants;

(iii) a nucleic acid capable of hybridizing under stringent conditions with any of the nucleic acids according to (i) or (ii) or a complement thereof, and which preferably encodes a OCP3 protein that has essentially the same biological activity as an OCP3 protein encoded by SEQ ID NO: 2; preferably the encoded OCP3 protein confers enhanced fungal resistance relative to control plants; and/or (iv) a nucleic acid encoding the same OCP3 protein as the nucleic acids of (i) to (iii) above, but differing from the nucleic acids of (i) to (iii) above due to the degeneracy of the genetic code, operably linked with (b) a promoter and (c) a transcription termination sequence is a further embodiment of the invention.

Furthermore, a recombinant vector construct is provided comprising:

(a) (i) a nucleic acid having at least 95%, at least 98%, at least 99% sequence identity, or even 100% sequence identity with SEQ ID NO: 1;

(ii) a nucleic acid coding for a protein having at least 95%, at least 98%, at least 99% sequence identity, or even 100% sequence identity with SEQ ID NO: 2; preferably the encoded protein confers enhanced fungal resistance relative to control plants;

(iii) a nucleic acid capable of hybridizing under stringent conditions with any of the nucleic acids according to (i) or (ii) or a complement thereof, and which preferably encodes a OCP3 protein that has essentially the same biological activity as an OCP3 protein encoded by SEQ ID NO: 2; preferably the encoded OCP3 protein confers enhanced fungal resistance relative to control plants; and/or (iv) a nucleic acid encoding the same OCP3 protein as the nucleic acids of (i) to (iii) above, but differing from the nucleic acids of (i) to (iii) above due to the degeneracy of the genetic code, operably linked with (b) a promoter and (c) a transcription termination sequence is a further embodiment of the invention.

Promoters according to the present invention may be constitutive, inducible, in particular pathogen-inducible, developmental stage-preferred, cell type-preferred, tissue-preferred or organ-preferred. Constitutive promoters are active under most conditions. Non-limiting examples of constitutive promoters include the CaMV 19S and 35S promoters (Odell et al., 1985, Nature 313:810-812), the sX CaMV 35S promoter (Kay et al., 1987, Science 236:1299-1302), the Sep1 promoter, the rice actin promoter (McElroy et al., 1990, Plant Cell 2:163-171), the *Arabidopsis* actin promoter, the ubiquitin promoter (Christensen et al., 1989, Plant Molec. Biol. 18:675-689); pEmu (Last et al., 1991, Theor. Appl. Genet. 81:581-588), the figwort mosaic virus 35S promoter, the Smas promoter (Velten et al., 1984, EMBO J. 3:2723-2730), the GRP1-8 promoter, the cinnamyl alcohol dehydrogenase promoter (U.S. Pat. No. 5,683,439), promoters from the T-DNA of *Agrobacterium*, such as mannopine synthase, nopaline synthase, and octopine synthase, the small subunit of ribulose biphosphate carboxylase (ssuRUBISCO) promoter, and/or the like.

Preferably, the expression vector of the invention comprises a constitutive promoter, mesophyll-specific promoter, epidermis-specific promoter, root-specific promoter, a pathogen inducible promoter, or a fungal-inducible promoter. A promoter is inducible, if its activity, measured on the amount of RNA produced under control of the promoter, is at least 30%, at least 40%, at least 50% preferably at least 60%, at least 70%, at least 80%, at least 90% more preferred at least 100%, at least 200%, at least 300% higher in its induced state, than in its un-induced state. A promoter is cell-, tissue- or organ-specific, if its activity, measured on the amount of RNA produced under control of the promoter, is at least 30%, at least 40%, at least 50% preferably at least 60%, at least 70%, at least 80%, at least 90% more preferred at least 100%, at least 200%, at least 300% higher in a particular cell-type, tissue or organ, then in other cell-types or tissues of the same plant, preferably the other cell-types or tissues are cell types or tissues of the same plant organ, e.g. a root. In the case of organ specific promoters, the promoter activity has to be compared to the promoter activity in other plant organs, e.g. leaves, stems, flowers or seeds. Preferably, the promoter is a constitutive promoter, mesophyll-specific promoter, or epidermis-specific promoter.

Preferably, the promoter is an epidermis-specific promoter, most preferred is the Glyma02g47670 promoter (as in SEQ ID NO: 3). Preferably, the promoter sequence comprises a nucleic acid having at least 70%, at least 80%, at least 90%, at least 95%, at least 98%, at least 99% sequence identity, or even 100% sequence identity with SEQ ID NO: 3 or a functional fragment thereof, or an orthologue or a paralogue thereof.

In preferred embodiments, the increase in the protein amount and/or activity of the OCP3 protein takes place in a constitutive or tissue-specific manner. In especially preferred embodiments, an essentially pathogen-induced increase in the protein amount and/or protein activity takes place, for example by recombinant expression of the OCP3 nucleic acid under the control of a fungal-inducable promoter. In particular, the expression of the OCP3 nucleic acid takes place on fungal infected sites, where, however, preferably the expression of the OCP3 nucleic acid remains essentially unchanged in tissues not infected by fungus.

Developmental stage-preferred promoters are preferentially expressed at certain stages of development. Tissue and organ preferred promoters include those that are preferentially expressed in certain tissues or organs, such as leaves, roots, seeds, or xylem. Examples of tissue preferred and organ preferred promoters include, but are not limited to fruit-preferred, ovule-preferred, male tissue-preferred, seed-preferred, integument-preferred, tuberpreferred, stalk-preferred, pericarp-preferred, leaf-preferred, stigma-preferred, pollenpreferred, anther-preferred, a petal-preferred, sepal-preferred, pedicel-preferred, siliquepreferred, stem-preferred, root-preferred promoters and/or the like. Seed preferred promoters are preferentially expressed during seed development and/or germination. For example, seed preferred promoters can be embryo-preferred, endosperm preferred and seed coatpreferred. See Thompson et al., 1989, BioEssays 10:108. Examples of seed preferred promoters include, but are not limited to cellulose synthase (celA), Cim1, gamma-zein, globulin-1, maize 19 kD zein (cZ19B1) and/or the like.

Other suitable tissue-preferred or organ-preferred promoters include, but are not limited to, the napin-gene promoter from rapeseed (U.S. Pat. No. 5,608,152), the USP-promoter from *Vicia faba* (Baeumlein et al., 1991, Mol Gen Genet. 225(3):459-67), the oleosinpromoter from *Arabidopsis* (PCT Application No. WO 98/45461), the phaseolin-promoter from *Phaseolus vulgaris* (U.S. Pat. No. 5,504,200), the Bce4-promoter from *Brassica* (PCT Application No. WO 91/13980), or the legumin B4 promoter (LeB4; Baeumlein et al., 1992, Plant Journal, 2(2):233-9), as well as promoters conferring seed specific expression in monocot plants like maize, barley, wheat, rye, rice, etc. Suitable promoters to note are the Ipt2 or Ipt1-gene promoter from barley (PCT Application No. WO 95/15389 and PCT Application No. WO 95/23230) or those described in PCT Application No. WO 99/16890 (promoters from the barley hordein-gene, rice glutelin gene, rice oryzin gene, rice prolamin gene, wheat gliadin gene, wheat glutelin gene, oat glutelin gene, Sorghum kasirin-gene, and/or rye secalin gene).

Promoters useful according to the invention include, but are not limited to, are the major chlorophyll a/b binding protein promoter, histone promoters, the Ap3 promoter, the β-conglycin promoter, the napin promoter, the soybean lectin promoter, the maize 15 kD zein promoter, the 22 kD zein promoter, the 27 kD zein promoter, the g-zein promoter, the waxy, shrunken 1, shrunken 2, bronze promoters, the Zm13 promoter (U.S. Pat. No. 5,086,169), the maize polygalacturonase promoters (PG) (U.S. Pat. Nos. 5,412,085 and 5,545,546), the SGB6 promoter (U.S. Pat. No. 5,470,359), as well as synthetic or other natural promoters.

Epidermis-specific promoters may be selected from the group consisting of:
WIR5 (=GstA1); acc. X56012; Dudler & Schweizer,
GLP4, acc. AJ310534; Wei Y., Zhang Z., Andersen C. H., Schmelzer E., Gregersen P. L.,
Collinge D. B., Smedegaard-Petersen V. and Thordal-Christensen H., Plant Molecular
Biology 36, 101 (1998),
GLP2a, acc. AJ237942, Schweizer P., Christoffel A. and Dudler R., Plant J. 20, 541 (1999);
Prx7, acc. AJ003141, Kristensen B. K., Ammitzböll H., Rasmussen S. K. and Nielsen K. A.,
Molecular Plant Pathology, 2(6), 311 (2001);
GerA, acc. AF250933; Wu S., Druka A., Horvath H., Kleinhofs A., Kannangara G. and von
Wettstein D., Plant Phys Biochem 38, 685 (2000);
OsROC1, acc. AP004656
RTBV, acc. AAV62708, AAV62707; Kloti A., Henrich C., Bieri S., He X., Chen G., Burkhardt
P. K., Wünn J., Lucca P., Hohn T., Potrykus I. and Fütterer J., PMB 40, 249 (1999);
Chitinase ChtC2-Promoter from potato (Ancillo et al., Planta. 217(4), 566, (2003));
AtProT3 Promoter (Grallath et al., Plant Physiology. 137(1), 117 (2005));
SHN-Promoters from *Arabidopsis* (AP2/EREBP transcription factors involved in cutin and
wax production) (Aaron et al., Plant Cell. 16(9), 2463 (2004)); and/or
GSTA1 from wheat (Dudler et al., WP2005306368 and Altpeter et al., Plant Molecular Biology. 57(2), 271 (2005)).

Mesophyll-specific promoters may be selected from the group consisting of:
PPCZm1 (=PEPC); Kausch A. P., Owen T. P., Zachwieja S. J., Flynn A. R. and Sheen J., Plant Mol. Biol. 45, 1 (2001);
OsrbcS, Kyozuka et al., PlaNT Phys 102, 991 (1993); Kyozuka J., McElroy D., Hayakawa T., Xie Y., Wu R. and Shimamoto K., Plant Phys. 102, 991 (1993);
OsPPDK, acc. AC099041;
TaGF-2.8, acc. M63223; Schweizer P., Christoffel A. and Dudler R., Plant J. 20, 541 (1999);
TaFBPase, acc. X53957;
TaWIS1, acc. AF467542; US 200220115849;
HvBIS1, acc. AF467539; US 200220115849;
ZmMIS1, acc. AF467514; US 200220115849;
HvPR1a, acc. X74939; Bryngelsson et al., Mol. Plant Microbe Interacti. 7 (2), 267 (1994);
HvPR1b, acc. X74940; Bryngelsson et al., Mol. Plant Microbe Interact. 7(2), 267 (1994);
HvB1,3gluc; acc. AF479647;
HvPrx8, acc. AJ276227; Kristensen et al., Molecular Plant Pathology, 2(6), 311 (2001);
and/or
HvPAL, acc. X97313; Wei Y., Zhang Z., Andersen C. H., Schmelzer E., Gregersen P. L., Collinge D. B., Smedegaard-Petersen V. and Thordal-Christensen H. Plant Molecular Biology 36, 101 (1998).

Constitutive promoters may be selected from the group consisting of
PcUbi promoter from parsley (WO 03/102198)
CaMV 35S promoter: Cauliflower Mosaic Virus 35S promoter (Benfey et al. 1989 EMBO J. 8(8): 2195-2202),
STPT promoter: *Arabidopsis thaliana* Short Triose phosphat translocator promoter (Accession NM_123979)
Act1 promoter:—*Oryza sativa* actin 1 gene promoter (McElroy et al. 1990 PLANT CELL 2(2) 163-171 a) and/or
EF1A2 promoter: *Glycine max* translation elongation factor EF1 alpha (US 20090133159).

One type of vector construct is a "plasmid," which refers to a circular double stranded DNA loop into which additional DNA segments can be ligated. Another type of vector is a viral vector, wherein additional DNA segments can be ligated into the viral genome. Certain vector constructs are capable of autonomous replication in a host plant cell into which they are introduced. Other vector constructs are integrated into the genome of a host plant cell upon introduction into the host cell, and thereby are replicated along with the host genome. In particular the vector construct is capable of directing the expression of gene to which the vectors is operatively linked. However, the invention is intended to include such other forms of expression vector constructs, such as viral vectors (e.g., potato virus X, tobacco rattle virus, and/or Gemini virus), which serve equivalent functions.

In preferred embodiments, the increase in the protein quantity or function of the OCP3 protein takes place in a constitutive or tissue-specific manner. In especially preferred embodiments, an essentially pathogen-induced increase in the protein quantity or protein function takes place, for example by exogenous expression of the OCP3 nucleic acid under the control of a fungal-inducible promoter. In particular, the expression of the OCP3 nucleic acid takes place on fungal infected sites, where, however, preferably the expression of the OCP3 nucleic acid sequence remains essentially unchanged in tissues not infected by fungus. In preferred embodiments, the protein amount of an OCP3 protein in the plant is increased by at least 10%, at least 20%, at least 30%, at least 40%, at least 50%, at least 60%, at least 70%, at least 80%, at least 90%, or at least 95% or more in comparison to a wild type plant that is not transformed with the OCP3 nucleic acid.

Transgenic organisms; transgenic plants, plant parts, and plant cells

A preferred embodiment is a transgenic plant, transgenic plant part, or transgenic plant cell overexpressing an exogenous OCP3 protein. Preferably, the OCP3 protein overexpressed in the plant, plant part or plant cell is encoded by
(i) an exogenous nucleic acid having at least 60% identity with SEQ ID NO: 1, 4-11, 12, 14, 16, 18, 20, 22, 24, or 26 or a functional fragment, thereof, an orthologue or a paralogue thereof; or by
(ii) an exogenous nucleic acid encoding a protein having at least 60% identity with SEQ ID NO: 2, 13, 15, 17, 19, 21, 23, 25, or 27, a functional fragment thereof, an orthologue or a paralogue thereof; preferably the encoded protein confers enhanced fungal resistance relative to control plants;
(iii) an exogenous nucleic acid capable of hybridizing under stringent conditions with any of the nucleic acids according to (i) or (ii) or a complement thereof, and which preferably encodes a OCP3 protein that has essentially the same biological activity as an OCP3 protein encoded by SEQ ID NO: 2; preferably the encoded OCP3 protein confers enhanced fungal resistance relative to control plants; and/or by
(iv) an exogenous nucleic acid encoding the same OCP3 protein as the nucleic acids of (i) to (iii) above, but differing from the nucleic acids of (i) to (iii) above due to the degeneracy of the genetic code.

A preferred embodiment is a transgenic plant, transgenic plant part, or transgenic plant cell overexpressing an exogenous OCP3 protein. Preferably, the OCP3 protein overexpressed in the plant, plant part or plant cell is encoded by
(i) an exogenous nucleic acid having at least 60% identity with SEQ ID NO: 1 or a functional fragment, thereof, an orthologue or a paralogue thereof; or by
(ii) an exogenous nucleic acid encoding a protein having at least 60% identity with SEQ ID NO: 2, a functional fragment thereof, an orthologue or a paralogue thereof; preferably the encoded protein confers enhanced fungal resistance relative to control plants;
(iii) an exogenous nucleic acid capable of hybridizing under stringent conditions with any of the nucleic acids according to (i) or (ii) or a complement thereof, and which preferably encodes a OCP3 protein that has essentially the same biological activity as an OCP3 protein encoded by SEQ ID NO: 2; preferably the encoded OCP3 protein confers enhanced fungal resistance relative to control plants; and/or by
(iv) an exogenous nucleic acid encoding the same OCP3 protein as the nucleic acids of (i) to (iii) above, but differing from the nucleic acids of (i) to (iii) above due to the degeneracy of the genetic code.

Most preferably, the exogenous nucleic acid has at least 95%, at least 98%, at least 99% sequence identity, or even 100% sequence identity with SEQ ID NO: 1; or comprises an exogenous nucleic acid encoding a protein having at least 95%, at least 98%, at least 99% sequence identity, or even 100% sequence identity with SEQ ID NO: 2.

More preferably, the transgenic plant, transgenic plant part, or transgenic plant cell according to the present invention has been obtained by transformation with a recombinant vector described herein.

Suitable methods for transforming or transfecting host cells including plant cells are well known in the art of plant biotechnology. Any method may be used to transform the recombinant expression vector into plant cells to yield the transgenic plants of the invention. General methods for transforming dicotyledonous plants are disclosed, for example, in U.S. Pat. Nos. 4,940,838; 5,464,763, and the like. Methods for transforming specific dicotyledonous plants, for example, cotton, are set forth in U.S. Pat. Nos. 5,004,863; 5,159,135; and 5,846,797. Soy transformation methods are set forth in U.S. Pat. Nos. 4,992,375; 5,416,011; 5,569,834; 5,824,877; 6,384,301 and in EP 0301749B1 may be used. Transformation methods may include direct and indirect methods of transformation. Suitable direct methods include polyethylene glycol induced DNA uptake, liposome-mediated transformation (U.S. Pat. No. 4,536,475), biolistic methods using the gene gun (Fromm M E et al, Bio/Technology. 8(9):833-9, 1990; Gordon-Kamm et al. Plant Cell 2:603, 1990), electroporation, incubation of dry embryos in DNA-comprising solution, and microinjection. In the case of these direct transformation methods, the plasmids used need not meet any particular requirements. Simple plasmids, such as those of the pUC series, pBR322, M13mp series, pACYC184 and the like can be used. If intact plants are to be regenerated from the transformed cells, an additional selectable marker gene is preferably located on the plasmid. The direct transformation techniques are equally suitable for dicotyledonous and monocotyledonous plants.

Transformation can also be carried out by bacterial infection by means of *Agrobacterium* (for example EP 0 116 718), viral infection by means of viral vectors (EP 0 067 553; U.S. Pat. No. 4,407,956; WO 95/34668; WO 93/03161) or by means of pollen (EP 0 270 356; WO 85/01856; U.S. Pat. No. 4,684,611). *Agrobacterium* based transformation techniques (especially for dicotyledonous plants) are well known in the art. The *Agrobacterium* strain (e.g., *Agrobacterium tumefaciens* or *Agrobacterium rhizogenes*) comprises a plasmid (Ti or Ri plasmid) and a T-DNA element which is transferred to the plant following infection with *Agrobacterium*. The T-DNA (transferred DNA) is integrated into the genome of the plant cell. The T-DNA may be localized on the Ri- or Ti-plasmid or is separately comprised in a so-called binary vector. Methods for the *Agrobacterium*-mediated transformation are described, for example, in Horsch R B et al. (1985) Science 225:1229. The *Agrobacterium*-mediated transformation is best suited to dicotyledonous plants but has also been adapted to monocotyledonous plants. The transformation of plants by Agrobacteria is described in, for example, White F F, Vectors for Gene Transfer in Higher Plants, Transgenic Plants, Vol. 1, Engineering and Utilization, edited by S. D. Kung and R. Wu, Academic Press, 1993, pp. 15-38; Jenes B et al. Techniques for Gene Transfer, Transgenic Plants, Vol. 1, Engineering and Utilization, edited by S. D. Kung and R. Wu, Academic Press, 1993, pp. 128-143; Potrykus (1991) Annu Rev Plant Physiol Plant Molec Biol 42:205-225. Transformation may result in transient or stable transformation and expression. Although a nucleotide sequence of the present invention can be inserted into any plant and plant cell falling within these broad classes, it is particularly useful in crop plant cells.

The genetically modified plant cells can be regenerated via all methods with which the skilled worker is familiar. Suitable methods can be found in the abovementioned publications by S. D. Kung and R. Wu, Potrykus or Höfgen and Willmitzer.

After transformation, plant cells or cell groupings may be selected for the presence of one or more markers which are encoded by plant-expressible genes co-transferred with the gene of interest, following which the transformed material is regenerated into a whole plant. To select transformed plants, the plant material obtained in the transformation is, as a rule, subjected to selective conditions so that transformed plants can be distinguished from untransformed plants. For example, the seeds obtained in the above-described manner can be planted and, after an initial growing period, subjected to a suitable selection by spraying. A further possibility consists in growing the seeds, if appropriate after sterilization, on agar plates using a suitable selection agent so that only the transformed seeds can grow into plants. Alternatively, the transformed plants are screened for the presence of a selectable marker such as the ones described above. The transformed plants may also be directly selected by screening for the presence of the OCP3 nucleic acid.

Following DNA transfer and regeneration, putatively transformed plants may also be evaluated, for instance using Southern analysis, for the presence of the gene of interest, copy number and/or genomic organisation. Alternatively or additionally, expression levels of the newly introduced DNA may be monitored using Northern and/or Western analysis, both techniques being well known to persons having ordinary skill in the art.

The generated transformed plants may be propagated by a variety of means, such as by clonal propagation or classical breeding techniques. For example, a first generation (or T1) transformed plant may be selfed and homozygous second-generation (or T2) transformants selected, and the T2 plants may then further be propagated through classical breeding techniques. The generated transformed organisms may take a variety of forms. For example, they may be chimeras of transformed cells and non-transformed cells; clonal transformants (e.g., all cells transformed to contain the expression cassette); grafts of transformed and untransformed tissues (e.g., in plants, a transformed rootstock grafted to an untransformed scion).

Preferably, the transgenic plant of the present invention or the plant obtained by the method of the present invention has increased resistance against fungal pathogens, preferably against fungal pathogens of the family Phacopsoraceae, more preferably against fungal pathogens of the genus *Phacopsora*, most preferably against *Phakopsora pachyrhizi* (Sydow) and *Phakopsora meibomiae* (Arthur), also known as soybean rust. Preferably, resistance against *Phakopsora pachyrhizi* (Sydow) and/or *Phakopsora meibomiae* (Arthur) is increased.

Preferably, the plant, plant part, or plant cell is a plant or derived from a plant selected from the group consisting of beans, soya, pea, clover, kudzu, lucerne, lentils, lupins, vetches, groundnut, rice, wheat, barley, *arabidopsis*, lentil, banana, canola, cotton, potato, corn, sugar cane, alfalfa, and sugar beet.

In one embodiment of the present invention the plant is selected from the group consisting of beans, soya, pea, clover, kudzu, lucerne, lentils, lupins, vetches, and/or groundnut. Preferably, the plant is a legume, comprising plants of the genus *Phaseolus* (comprising French bean, dwarf bean, climbing bean (*Phaseolus vulgaris*), Lima bean (*Phaseolus lunatus* L.), Tepary bean (*Phaseolus acutifolius* A. Gray), runner bean (*Phaseolus coccineus*)); the genus *Glycine* (comprising *Glycine soja*, soybeans (*Glycine max* (L.) MariII)); pea (*Pisum*) (comprising shelling peas (*Pisum sativum* L. convar. *sativum*), also called smooth or round-seeded peas; marrowfat pea (*Pisum sativum* L. convar. medullare Alef. emend. C.O. Lehm), sugar pea (*Pisum sativum* L. convar. axiphium Alef emend. C.O. Lehm), also called snow pea, edible-podded pea or mangetout, (*Pisum granda sneida* L. convar. sneidulo p. shneiderium)); peanut (*Arachis hypogaea*), clover (*Trifolium* spec.), medick (*Medicago*), kudzu vine (*Pueraria lobata*), common lucerne, alfalfa (*M. sativa* L.), chickpea (*Cicer*), lentils (Lens) (*Lens culinaris* Medik.), lupins (*Lupinus*); vetches (*Vicia*), field bean, broad bean (*Vicia faba*), vetchling (*Lathyrus*) (comprising chickling pea (*Lathyrus sativus*), heath pea (*Lathyrus tuberosus*)); genus *Vigna* (comprising moth bean (*Vigna aconitifolia* (Jacq.) Maréchal), adzuki bean (*Vigna angularis* (Willd.) Ohwi & H. Ohashi), urd bean (*Vigna mungo* (L.) Hepper), mung bean (*Vigna radiata* (L.) R. Wilczek), bambara groundnut (*Vigna subterrane* (L.) Verdc.), rice bean (*Vigna umbellata* (Thunb.) Ohwi & H. Ohashi), *Vigna vexillata* (L.) A. Rich., *Vigna unguiculata* (L.) Walp., in the three subspecies asparagus bean, cowpea, catjang bean));
pigeonpea (*Cajanus cajan* (L.) Millsp.), the genus *Macrotyloma* (comprising geocarpa groundnut (*Macrotyloma geocarpum* (Harms) Maréchal & Baudet), horse bean (*Macrotyloma uniflorum* (Lam.) Verdc.)); goa bean (*Psophocarpus tetragonolobus* (L.) DC.), African yam bean (*Sphenostylis stenocarpa* (Hochst. ex A. Rich.) Harms), Egyptian black bean, *dolichos* bean, *lablab* bean (*Lablab purpureus* (L.) Sweet), yam bean (*Pachyrhizus*), guar bean (*Cyamopsis tetragonolobus* (L.) Taub.); and/or the genus *Canavalia* (comprising jack bean (*Canavalia ensiformis* (L.) DC.), sword bean (*Canavalia gladiata* (Jacq.) DC.)).

Further preferred is a plant selected from plant is selected from the group consisting of beans, soya, pea, clover, kudzu, lucerne, lentils, lupins, vetches, and groundnut. Most preferably, the plant, plant part, or plant cell is or is derived from soy.

Methods for the Production of Transgenic Plants

One embodiment according to the present invention provides a method for producing a transgenic plant, a transgenic plant part, or a transgenic plant cell resistant to a fungal pathogen, preferably of the family Phacosporaceae, for example soybean rust, wherein the recombinant nucleic acid used to generate a transgenic plant comprises a promoter that is functional in the plant cell, operably linked to an OCP3 nucleic acid, which is preferably SEQ ID NO: 1, 4-11, 12, 14, 16, 18, 20, 22, 24, or 26, and a terminator regulatory sequence.

In one embodiment, the present invention refers to a method for the production of a transgenic plant, transgenic plant part, or transgenic plant cell having increased fungal resistance, comprising (a) introducing a recombinant vector construct according to the present invention into a plant, a plant part or a plant cell and (b) generating a transgenic plant from the plant, plant part or plant cell.

Preferably, the method for the production of the transgenic plant, transgenic plant part, or transgenic plant cell further comprises the step (c) expressing the OCP3 protein, preferably encoded by
  (i) an exogenous nucleic acid having at least 60% identity with SEQ ID NO: 1, 4-11, 12, 14, 16, 18, 20, 22, 24, or 26, a functional fragment thereof, an orthologue or a paralogue thereof;
  (ii) an exogenous nucleic acid encoding a protein having at least 60% identity with SEQ ID NO: 2, 13, 15, 17, 19, 21, 23, 25, or 27, or a functional fragment thereof, an orthologue or a paralogue thereof; preferably the encoded protein confers enhanced fungal resistance relative to control plants;
  (iii) an exogenous nucleic acid capable of hybridizing under stringent conditions with any of the nucleic acids according to (i) or (ii) or a complement thereof, and which preferably encodes a OCP3 protein that has essentially the same biological activity as an OCP3 protein encoded by SEQ ID NO: 2; preferably the encoded OCP3 protein confers enhanced fungal resistance relative to control plants; and/or by
  (iv) an exogenous nucleic acid encoding the same OCP3 protein as the nucleic acids of (i) to (iii) above, but differing from the nucleic acids of (i) to (iii) above due to the degeneracy of the genetic code.

Preferably, the method for the production of the transgenic plant, transgenic plant part, or transgenic plant cell further comprises the step (c) expressing the OCP3 protein, preferably encoded by
- (i) an exogenous nucleic acid having at least 60% identity with SEQ ID NO: 1, a functional fragment thereof, an orthologue or a paralogue thereof;
- (ii) an exogenous nucleic acid encoding a protein having at least 60% identity with SEQ ID NO: 2, or a functional fragment thereof, an orthologue or a paralogue thereof; preferably the encoded protein confers enhanced fungal resistance relative to control plants;
- (iii) an exogenous nucleic acid capable of hybridizing under stringent conditions with any of the nucleic acids according to (i) or (ii) or a complement thereof, and which preferably encodes a OCP3 protein that has essentially the same biological activity as an OCP3 protein encoded by SEQ ID NO: 2; preferably the encoded OCP3 protein confers enhanced fungal resistance relative to control plants; and/or by
- (iv) an exogenous nucleic acid encoding the same OCP3 protein as the nucleic acids of (i) to (iii) above, but differing from the nucleic acids of (i) to (iii) above due to the degeneracy of the genetic code.

Preferably, the method for the production of the transgenic plant, transgenic plant part, or transgenic plant cell additionally comprises the step of harvesting the seeds of the transgenic plant and planting the seeds and growing the seeds to plants, wherein the grown plant(s) comprises
- (i) the exogenous nucleic acid having at least 60% identity with SEQ ID NO: 1, 4-11, 12, 14, 16, 18, 20, 22, 24, or 26, a functional fragment thereof, an orthologue or a paralogue thereof;
- (ii) the exogenous nucleic acid encoding a protein having at least 60% identity with SEQ ID NO: 2, 13, 15, 17, 19, 21, 23, 25, or 27, or a functional fragment thereof, an orthologue or a paralogue thereof; preferably the encoded protein confers enhanced fungal resistance relative to control plants;
- (iii) the exogenous nucleic acid capable of hybridizing under stringent conditions with any of the nucleic acids according to (i) or (ii) or a complement thereof, and which preferably encodes a OCP3 protein that has essentially the same biological activity as an OCP3 protein encoded by SEQ ID NO: 2; preferably the encoded OCP3 protein confers enhanced fungal resistance relative to control plants; and/or
- (iv) the exogenous nucleic acid encoding the same OCP3 protein as the nucleic acids of (i) to (iii) above, but differing from the nucleic acids of (i) to (iii) above due to the degeneracy of the genetic code.

Preferably, the method for the production of the transgenic plant, transgenic plant part, or transgenic plant cell additionally comprises the step of harvesting the seeds of the transgenic plant and planting the seeds and growing the seeds to plants, wherein the grown plant(s) comprises
- (i) the exogenous nucleic acid having at least 60% identity with SEQ ID NO: 1, a functional fragment thereof, an orthologue or a paralogue thereof;
- (ii) the exogenous nucleic acid encoding a protein having at least 60% identity with SEQ ID NO: 2, or a functional fragment thereof, an orthologue or a paralogue thereof; preferably the encoded protein confers enhanced fungal resistance relative to control plants;
- (iii) the exogenous nucleic acid capable of hybridizing under stringent conditions with any of the nucleic acids according to (i) or (ii) or a complement thereof, and which preferably encodes a OCP3 protein that has essentially the same biological activity as an OCP3 protein encoded by SEQ ID NO: 2; preferably the encoded OCP3 protein confers enhanced fungal resistance relative to control plants; and/or
- (iv) the exogenous nucleic acid encoding the same OCP3 protein as the nucleic acids of (i) to (iii) above, but differing from the nucleic acids of (i) to (iii) above due to the degeneracy of the genetic code.

The transgenic plants may be selected by known methods as described above (e.g., by screening for the presence of one or more markers which are encoded by plant-expressible genes co-transferred with the OCP3 gene or by directly screening for the OCP3 nucleic acid).

Furthermore, the use of the exogenous OCP3 nucleic acid or the recombinant vector construct comprising the OCP3 nucleic acid for the transformation of a plant, plant part, or plant cell to provide a fungal resistant plant, plant part, or plant cell is provided.

Harvestable Parts and Products

Harvestable parts of the transgenic plant according to the present invention are part of the invention. The harvestable parts may be seeds, roots, leaves and/or flowers comprising the OCP3 nucleic acid or OCP3 protein or parts thereof. Preferred parts of soy plants are soy beans comprising the OCP3 nucleic acid or OCP3 protein.

Products derived from a transgenic plant according to the present invention, parts thereof or harvestable parts thereof are part of the invention. A preferred product is soybean meal or soybean oil.

Preferably, the harvestable part of the transgenic plant or the product derived from the transgenic plant comprises an exogenous OCP3 nucleic acid, wherein the exogenous OCP3 nucleic acid is selected from the group consisting of:
- (i) an exogenous nucleic acid having at least 60%, preferably at least 70%, for example at least 75%, more preferably at least 80%, for example at least 85%, even more preferably at least 90%, for example at least 95% or at least 96% or at least 97% or at least 98% most preferably 99% identity with SEQ ID NO: 1, 4-11, 12, 14, 16, 18, 20, 22, 24, or 26, a functional fragment thereof, or an orthologue or a paralogue thereof; or by
- (ii) an exogenous nucleic acid encoding a protein having at least 60% identity, preferably at least 70%, for example at least 75%, more preferably at least 80%, for example at least 85%, even more preferably at least 90%, for example at least 95% or at least 96% or at least 97% or at least 98% most preferably 99% homology with SEQ ID NO: 2, 13, 15, 17, 19, 21, 23, 25, or 27, a functional fragment thereof, an orthologue or a paralogue thereof, or by
- (iii) an exogenous nucleic acid capable of hybridizing under stringent conditions with any of the nucleic acids according to (i) or (ii) or a complementary sequence (complement) thereof, and which preferably encodes a OCP3 protein that has essentially the same biological activity as an OCP3 protein encoded by SEQ ID NO: 2; preferably the encoded OCP3 protein confers enhanced fungal resistance relative to control plants;

or wherein the harvestable part of the transgenic plant or the product derived from the transgenic plant comprises an OCP3 protein encoded by any one of the OCP3 nucleic acids of (i) to (iii).

Methods for Manufacturing a Product

In one embodiment the method for the production of a product comprises
a) growing the plants of the invention or obtainable by the methods of invention and
b) producing said product from or by the plants of the invention and/or parts, e.g. seeds, of these plants.

In a further embodiment the method comprises the steps a) growing the plants of the invention, b) removing the harvestable parts as defined above from the plants and c) producing said product from or by the harvestable parts of the invention.

Preferably, the product obtained by said method comprises an exogenous OCP3 nucleic acid, wherein the exogenous OCP3 nucleic acid is selected from the group consisting of:
(i) an exogenous nucleic acid having at least 60%, preferably at least 70%, for example at least 75%, more preferably at least 80%, for example at least 85%, even more preferably at least 90%, for example at least 95% or at least 96% or at least 97% or at least 98% most preferably 99% identity with SEQ ID NO: 1, 4-11, 12, 14, 16, 18, 20, 22, 24, or 26, a functional fragment thereof, or an orthologue or a paralogue thereof; or by
(ii) an exogenous nucleic acid encoding a protein having at least 60% identity, preferably at least 70%, for example at least 75%, more preferably at least 80%, for example at least 85%, even more preferably at least 90%, for example at least 95% or at least 96% or at least 97% or at least 98% most preferably 99% homology with SEQ ID NO: 2, 13, 15, 17, 19, 21, 23, 25, or 27, a functional fragment thereof, an orthologue or a paralogue thereof, or by
  (iii) an exogenous nucleic acid capable of hybridizing under stringent conditions with any of the nucleic acids according to (i) or (ii) or a complementary sequence (complement) thereof, and which preferably encodes a OCP3 protein that has essentially the same biological activity as an OCP3 protein encoded by SEQ ID NO: 2; preferably the encoded OCP3 protein confers enhanced fungal resistance relative to control plants;
or wherein the product obtained by said method comprises an OCP3 protein encoded by any one of the OCP3 nucleic acids of (i) to (iii).

The product may be produced at the site where the plant has been grown, the plants and/or parts thereof may be removed from the site where the plants have been grown to produce the product. Typically, the plant is grown, the desired harvestable parts are removed from the plant, if feasible in repeated cycles, and the product made from the harvestable parts of the plant. The step of growing the plant may be performed only once each time the methods of the invention is performed, while allowing repeated times the steps of product production e.g. by repeated removal of harvestable parts of the plants of the invention and if necessary further processing of these parts to arrive at the product. It is also possible that the step of growing the plants of the invention is repeated and plants or harvestable parts are stored until the production of the product is then performed once for the accumulated plants or plant parts. Also, the steps of growing the plants and producing the product may be performed with an overlap in time, even simultaneously to a large extend or sequentially. Generally the plants are grown for some time before the product is produced.

In one embodiment the products produced by said methods of the invention are plant products such as, but not limited to, a foodstuff, feedstuff, a food supplement, feed supplement, fiber, cosmetic and/or pharmaceutical. Foodstuffs are regarded as compositions used for nutrition and/or for supplementing nutrition. Animal feedstuffs and animal feed supplements, in particular, are regarded as foodstuffs.

In another embodiment the inventive methods for the production are used to make agricultural products such as, but not limited to, plant extracts, proteins, amino acids, carbohydrates, fats, oils, polymers, vitamins, and the like.

It is possible that a plant product consists of one or more agricultural products to a large extent.

Methods for Breeding/Methods for Plant Improvement/Methods Plant Variety Production The transgenic plants of the invention may be crossed with similar transgenic plants or with transgenic plants lacking the nucleic acids of the invention or with non-transgenic plants, using known methods of plant breeding, to prepare seeds. Further, the transgenic plant cells or plants of the present invention may comprise, and/or be crossed to another transgenic plant that comprises one or more exogenous nucleic acids, thus creating a "stack" of transgenes in the plant and/or its progeny. The seed is then planted to obtain a crossed fertile transgenic plant comprising the OCP3 nucleic acid. The crossed fertile transgenic plant may have the particular expression cassette inherited through a female parent or through a male parent. The second plant may be an inbred plant. The crossed fertile transgenic may be a hybrid. Also included within the present invention are seeds of any of these crossed fertile transgenic plants. The seeds of this invention can be harvested from fertile transgenic plants and be used to grow progeny generations of transformed plants of this invention including hybrid plant lines comprising the exogenous nucleic acid.

Thus, one embodiment of the present invention is a method for breeding a fungal resistant plant comprising the steps of
(a) crossing a transgenic plant described herein or a plant obtainable by a method described herein with a second plant;
(b) obtaining a seed or seeds resulting from the crossing step described in (a);
(c) planting said seed or seeds and growing the seed or seeds to plants; and
(d) selecting from said plants the plants expressing an OCP3 protein, preferably encoded by
  (i) an exogenous nucleic acid having at least 60% identity with SEQ ID NO: 1, 4-11, 12, 14, 16, 18, 20, 22, 24, or 26, a functional fragment thereof, an orthologue or a paralogue thereof;
  (ii) an exogenous nucleic acid encoding a protein having at least 60% identity with SEQ ID NO: 2, 13, 15, 17, 19, 21, 23, 25, or 27, or a functional fragment thereof, an orthologue or a paralogue thereof; preferably the encoded protein confers enhanced fungal resistance relative to control plants;
  (iii) an exogenous nucleic acid capable of hybridizing under stringent conditions with any of the nucleic acids according to (i) or (ii) or a complement thereof, and which preferably encodes a OCP3 protein that has essentially the same biological activity as an OCP3 protein encoded by SEQ ID NO: 2; preferably the encoded OCP3 protein confers enhanced fungal resistance relative to control plants; and/or by
  (iv) an exogenous nucleic acid encoding the same OCP3 protein as the nucleic acids of (i) to (iii) above, but differing from the nucleic acids of (i) to (iii) above due to the degeneracy of the genetic code.

Thus, one embodiment of the present invention is a method for breeding a fungal resistant plant comprising the steps of
(a) crossing a transgenic plant described herein or a plant obtainable by a method described herein with a second plant;
(b) obtaining a seed or seeds resulting from the crossing step described in (a);

(c) planting said seed or seeds and growing the seed or seeds to plants; and
(d) selecting from said plants the plants expressing an OCP3 protein, preferably encoded by
  (i) an exogenous nucleic acid having at least 60% identity with SEQ ID NO: 1, a functional fragment thereof, an orthologue or a paralogue thereof;
  (ii) an exogenous nucleic acid encoding a protein having at least 60% identity with SEQ ID NO: 2, or a functional fragment thereof, an orthologue or a paralogue thereof; preferably the encoded protein confers enhanced fungal resistance relative to control plants;
  (iii) an exogenous nucleic acid capable of hybridizing under stringent conditions with any of the nucleic acids according to (i) or (ii) or a complement thereof, and which preferably encodes a OCP3 protein that has essentially the same biological activity as an OCP3 protein encoded by SEQ ID NO: 2; preferably the encoded OCP3 protein confers enhanced fungal resistance relative to control plants; and/or by
  (iv) an exogenous nucleic acid encoding the same OCP3 protein as the nucleic acids of (i) to (iii) above, but differing from the nucleic acids of (i) to (iii) above due to the degeneracy of the genetic code.

Another preferred embodiment is a method for plant improvement comprising
(a) obtaining a transgenic plant by any of the methods of the present invention;
(b) combining within one plant cell the genetic material of at least one plant cell of the plant of (a) with the genetic material of at least one cell differing in one or more gene from the plant cells of the plants of (a);
(c) obtaining seed from at least on plant generated from the one plant cell of (b) or the plant of the cross of step (b);
(d) planting said seeds and growing the seeds to plants; and
(e) selecting from said plants, plants expressing the nucleic acid encoding the OCP3 protein; and optionally
(f) producing propagation material from the plants expressing the nucleic acid encoding the OCP3 protein.

The transgenic plants may be selected by known methods as described above (e.g., by screening for the presence of one or more markers which are encoded by plant-expressible genes co-transferred with the OCP3 gene or screening for the OCP3 nucleic acid itself).

According to the present invention, the introduced OCP3 nucleic acid may be maintained in the plant cell stably if it is incorporated into a non-chromosomal autonomous replicon or integrated into the plant chromosomes. Whether present in an extra-chromosomal nonreplicating or replicating vector construct or a vector construct that is integrated into a chromosome, the exogenous OCP3 nucleic acid preferably resides in a plant expression cassette. A plant expression cassette preferably contains regulatory sequences capable of driving gene expression in plant cells that are functional linked so that each sequence can fulfill its function, for example, termination of transcription by polyadenylation signals. Preferred polyadenylation signals are those originating from *Agrobacterium tumefaciens* t-DNA such as the gene 3 known as octopine synthase of the Ti-plasmid pTiACH5 (Gielen et al, 1984, EMBO J. 3:835) or functional equivalents thereof, but also all other terminators functionally active in plants are suitable. As plant gene expression is very often not limited on transcriptional levels, a plant expression cassette preferably contains other functional linked sequences like translational enhancers such as the overdrive-sequence containing the 5'-untranslated leader sequence from tobacco mosaic virus increasing the polypeptide per RNA ratio (Gallie et al., 1987, Nucl. Acids Research 15:8693-8711). Examples of plant expression vectors include those detailed in: Becker, D. et al., 1992, New plant binary vectors with selectable markers located proximal to the left border, Plant Mol. Biol. 20:1195-1197; Bevan, M. W., 1984, Binary *Agrobacterium* vectors for plant transformation, Nucl. Acid. Res. 12:8711-8721; and Vectors for Gene Transfer in Higher Plants; in: Transgenic Plants, Vol. 1, Engineering and Utilization, eds.: Kung and R. Wu, Academic Press, 1993, S. 15-38.

EXAMPLES

The following examples are not intended to limit the scope of the claims to the invention, but are rather intended to be exemplary of certain embodiments. Any variations in the exemplified methods that occur to the skilled artisan are intended to fall within the scope of the present invention.

Example 1: General Methods

The chemical synthesis of oligonucleotides can be affected, for example, in the known fashion using the phosphoamidite method (Voet, Voet, 2nd Edition, Wiley Press New York, pages 896-897). The cloning steps carried out for the purposes of the present invention such as, for example, restriction cleavages, agarose gel electrophoresis, purification of DNA fragments, transfer of nucleic acids to nitrocellulose and nylon membranes, linking DNA fragments, transformation of *E. coli* cells, bacterial cultures, phage multiplication and sequence analysis of recombinant DNA, are carried out as described by Sambrook et al. Cold Spring Harbor Laboratory Press (1989), ISBN 0-87969-309-6. The sequencing of recombinant DNA molecules is carried out with an MWG-Licor laser fluorescence DNA sequencer following the method of Sanger (Sanger et al., Proc. Natl. Acad. Sci. USA 74, 5463 (1977)).

Example 2: Cloning of Overexpression Vector Constructs

The cDNAs of all genes mentioned in this application were generated by DNA synthesis (Geneart, Regensburg, Germany).

The AtOCP3 cDNA (as shown in SEQ ID NO: 1) was synthesized in a way that a PacI restriction site is located in front of the start-ATG and a AscI restriction site downstream of the stop-codon. The synthesized cDNAs were digested using the restriction enzymes PacI and AscI (NEB Biolabs) and ligated in a PacI/AscI digested Gateway pENTRY-A vector (Invitrogen, Life Technologies, Carlsbad, Calif., USA) in a way that the full-length fragment is located in sense direction between the Glyma02g47670 promoter (epidermis-specific promoter) and an *Agrobacterium tumefaciens* derived nopaline synthase terminator (NOS) terminator.

Figure 2:
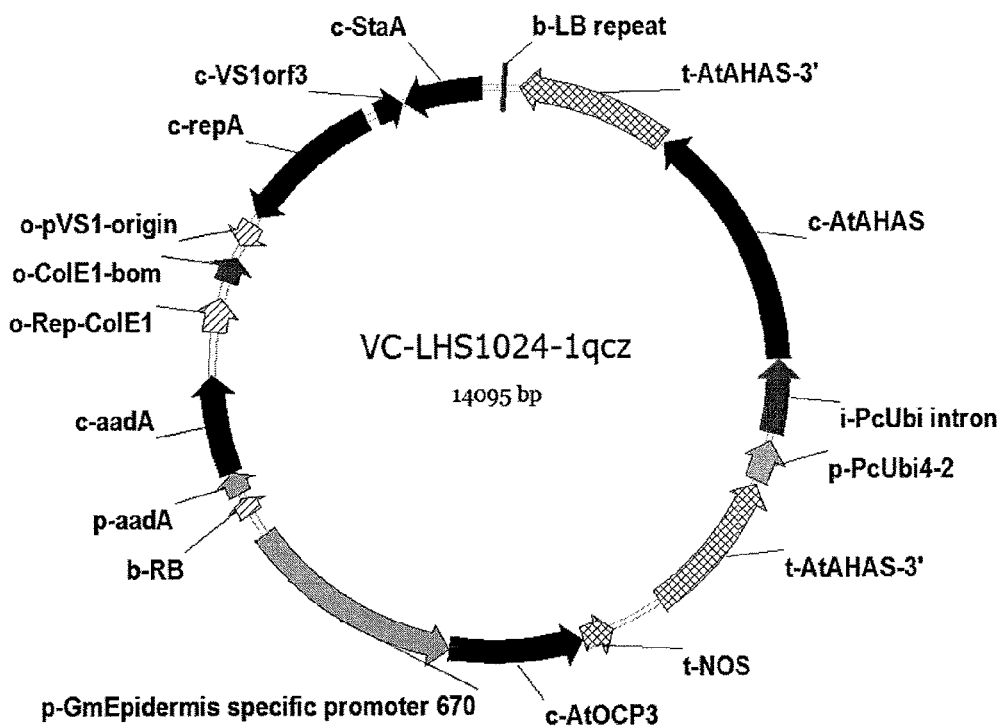
Figure 6:
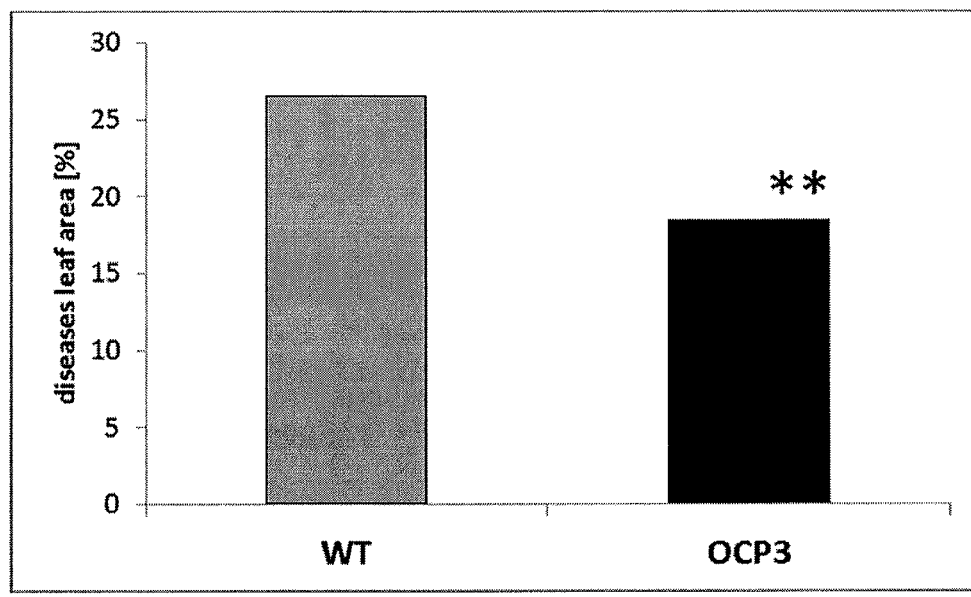

To obtain the binary plant transformation vector, a triple LR reaction (Gateway system, Invitrogen, Life Technologies, Carlsbad, Calif., USA) was performed according to manufacturers protocol by using the promoter::cDNA::terminator in a pENTRY-A vector, an empty pENTRY-B vector and an empty pENTRY-C vector. As target a binary pDEST vector was used which is composed of: (1) a Spectinomycin/Streptomycin resistance cassette for bacterial selection (2) a pVS1 origin for replication in Agrobacteria (3) a pBR322 origin of replication for stable maintenance in *E. coli* and (4) between the right and left border an AHAS selection under control of a pcUbi-promoter (FIG. 2). The recombination reaction was transformed into *E. coli* (DH5alpha), miniprepped and screened by specific restriction digestions. A positive clone from each vector construct was sequenced and submitted soy transformation.

Example 3: Soy Transformation

The expression vector constructs (see example 2) were transformed into soy.

3.1 Sterilization and Germination of Soy Seeds

Virtually any seed of any soy variety can be employed in the method of the invention. A variety of soycultivar (including Jack, Williams 82, Jake, Stoddard and Resnik) is appropriate for soy transformation. Soy seeds were sterilized in a chamber with a chlorine gas produced by adding 3.5 ml 12N HCl drop wise into 100 ml bleach (5.25% sodium hypochlorite) in a desiccator with a tightly fitting lid. After 24 to 48 hours in the chamber, seeds were removed and approximately 18 to 20 seeds were plated on solid GM medium with or without 5 µM 6-benzyl-aminopurine (BAP) in 100 mm Petri dishes. Seedlings without BAP are more elongated and roots develop, especially secondary and lateral root formation. BAP strengthens the seedling by forming a shorter and stockier seedling.

Seven-day-old seedlings grown in the light (>100 µEinstein/m$^2$s) at 25° C. were used for explant material for the three-explant types. At this time, the seed coat was split, and the epicotyl with the unifoliate leaves have grown to, at minimum, the length of the cotyledons. The epicotyl should be at least 0.5 cm to avoid the cotyledonary-node tissue (since soycultivars and seed lots may vary in the developmental time a description of the germination stage is more accurate than a specific germination time).

For inoculation of entire seedlings, see Method A (example 3.3.1 and 3.3.2) or leaf explants, see Method B (example 3.3.3).

For method C (see example 3.3.4), the hypocotyl and one and a half or part of both cotyledons were removed from each seedling. The seedlings were then placed on propagation media for 2 to 4 weeks. The seedlings produce several branched shoots to obtain explants from. The majority of the explants originated from the plantlet growing from the apical bud. These explants were preferably used as target tissue.

3.2—Growth and Preparation of *Agrobacterium* Culture

*Agrobacterium* cultures were prepared by streaking *Agrobacterium* (e.g., *A. tumefaciens* or *A. rhizogenes*) carrying the desired binary vector (e.g. H. Klee. R. Horsch and S. Rogers 1987 *Agrobacterium*-Mediated Plant Transformation and its further Applications to Plant Biology; Annual Review of Plant Physiology Vol. 38: 467-486) onto solid YEP growth medium YEP media: 10 g yeast extract, 10 g Bacto Peptone, 5 g NaCl, Adjust pH to 7.0, and bring final volume to 1 liter with H2O, for YEP agar plates add 20 g Agar, autoclave) and incubating at 25° C. until colonies appeared (about 2 days). Depending on the selectable marker genes present on the Ti or Ri plasmid, the binary vector, and the bacterial chromosomes, different selection compounds were be used for *A. tumefaciens* and *rhizogenes* selection in the YEP solid and liquid media. Various *Agrobacterium* strains can be used for the transformation method.

After approximately two days, a single colony (with a sterile toothpick) was picked and 50 ml of liquid YEP was inoculated with antibiotics and shaken at 175 rpm (25° C.) until an OD$_{600}$ between 0.8-1.0 is reached (approximately 2 d). Working glycerol stocks (15%) for transformation are prepared and one-ml of *Agrobacterium* stock aliquoted into 1.5 ml Eppendorf tubes then stored at −80° C.

The day before explant inoculation, 200 ml of YEP were inoculated with 5 µl to 3 ml of working *Agrobacterium* stock in a 500 ml Erlenmeyer flask. The flask was shaked overnight at 25° C. until the OD$_{600}$ was between 0.8 and 1.0. Before preparing the soy explants, the Agrobacteria were pelleted by centrifugation for 10 min at 5,500 xg at 20° C. The pellet was resuspended in liquid CCM to the desired density (OD$_{600}$ 0.5-0.8) and placed at room temperature at least 30 min before use.

3.3—Explant Preparation and Co-Cultivation (Inoculation)

3.3.1 Method a: Explant Preparation on the Day of Transformation.

Seedlings at this time had elongated epicotyls from at least 0.5 cm but generally between 0.5 and 2 cm. Elongated epicotyls up to 4 cm in length had been successfully employed. Explants were then prepared with: i) with or without some roots, ii) with a partial, one or both cotyledons, all preformed leaves were removed including apical meristem, and the node located at the first set of leaves was injured with several cuts using a sharp scalpel.

This cutting at the node not only induced *Agrobacterium* infection but also distributed the axillary meristem cells and damaged pre-formed shoots. After wounding and preparation, the explants were set aside in a Petri dish and subsequently co-cultivated with the liquid CCM/*Agrobacterium* mixture for 30 minutes. The explants were then removed from the liquid medium and plated on top of a sterile filter paper on 15×100 mm Petri plates with solid co-cultivation medium. The wounded target tissues were placed such that they are in direct contact with the medium.

3.3.2 Modified Method a: Epicotyl Explant Preparation

Soyepicotyl segments prepared from 4 to 8 d old seedlings were used as explants for regeneration and transformation. Seeds of soya cv. L00106CN, 93-41131 and Jack were germinated in 1/10 MS salts or a similar composition medium with or without cytokinins for 4 to 8 d. Epicotyl explants were prepared by removing the cotyledonary node and stem node from the stem section. The epicotyl was cut into 2 to 5 segments. Especially preferred are segments attached to the primary or higher node comprising axillary meristematic tissue.

The explants were used for *Agrobacterium* infection. *Agrobacterium* AGL1 harboring a plasmid with the gene of interest (G01) and the AHAS, bar or dsdA selectable marker gene was cultured in LB medium with appropriate antibiotics overnight, harvested and resuspended in a inoculation medium with acetosyringone. Freshly prepared epicotyl segments were soaked in the *Agrobacterium* suspension for 30 to 60 min and then the explants were blotted dry on sterile filter papers. The inoculated explants were then cultured on a coculture medium with L-cysteine and TTD and other chemicals such as acetosyringone for increasing T-DNA delivery for 2 to 4 d. The infected epicotyl explants were then placed on a shoot induction medium with selection agents such as imazapyr (for AHAS gene), glufosinate (for bar gene), or D-serine (for dsdA gene). The regenerated shoots were subcultured on elongation medium with the selective agent.

For regeneration of transgenic plants the segments were then cultured on a medium with cytokinins such as BAP, TDZ and/or Kinetin for shoot induction. After 4 to 8 weeks, the cultured tissues were transferred to a medium with lower concentration of cytokinin for shoot elongation. Elongated shoots were transferred to a medium with auxin for rooting and plant development. Multiple shoots were regenerated.

Many stable transformed sectors showing strong cDNA expression were recovered. Soyplants were regenerated from epicotyl explants. Efficient T-DNA delivery and stable transformed sectors were demonstrated.

3.3.3 Method B: Leaf Explants

For the preparation of the leaf explant the cotyledon was removed from the hypocotyl. The cotyledons were separated from one another and the epicotyl is removed. The primary leaves, which consist of the lamina, the petiole, and the stipules, were removed from the epicotyl by carefully cutting at the base of the stipules such that the axillary meristems were included on the explant. To wound the explant as well as to stimulate de novo shoot formation, any pre-formed shoots were removed and the area between the stipules was cut with a sharp scalpel 3 to 5 times.

The explants are either completely immersed or the wounded petiole end dipped into the Agrobacterium suspension immediately after explant preparation. After inoculation, the explants are blotted onto sterile filter paper to remove excess Agrobacterium culture and place explants with the wounded side in contact with a round 7 cm Whatman paper overlaying the solid CCM medium (see above). This filter paper prevents A. tumefaciens overgrowth on the soy-explants. Wrap five plates with Parafilm™ "M" (American National Can, Chicago, Ill., USA) and incubate for three to five days in the dark or light at 25° C.

3.3.4 Method C: Propagated Axillary Meristem

For the preparation of the propagated axillary meristem explant propagated 3-4 week-old plantlets were used. Axillary meristem explants can be pre-pared from the first to the fourth node. An average of three to four explants could be obtained from each seedling. The explants were prepared from plantlets by cutting 0.5 to 1.0 cm below the axillary node on the internode and removing the petiole and leaf from the explant. The tip where the axillary meristems lie was cut with a scalpel to induce de novo shoot growth and allow access of target cells to the Agrobacterium. Therefore, a 0.5 cm explant included the stem and a bud.

Once cut, the explants were immediately placed in the Agrobacterium suspension for 20 to 30 minutes. After inoculation, the explants were blotted onto sterile filter paper to remove excess Agrobacterium culture then placed almost completely immersed in solid CCM or on top of a round 7 cm filter paper overlaying the solid CCM, depending on the Agrobacterium strain. This filter paper prevents Agrobacterium overgrowth on the soy-explants. Plates were wrapped with Parafilm™ "M" (American National Can, Chicago, Ill., USA) and incubated for two to three days in the dark at 25° C.

3.4—Shoot Induction

After 3 to 5 days co-cultivation in the dark at 25° C., the explants were rinsed in liquid SIM medium (to remove excess Agrobacterium) (SIM, see Olhoft et al 2007 A novel Agrobacterium rhizogenes-mediated transformation method of soy using primary-node explants from seedlings In Vitro Cell. Dev. Biol.—Plant (2007) 43:536-549; to remove excess Agrobacterium) or Modwash medium (1× B5 major salts, 1× B5 minor salts, 1×MSIII iron, 3% Sucrose, 1×B5 vitamins, 30 mM MES, 350 mg/L Timentin™ pH 5.6, WO 2005/121345) and blotted dry on sterile filter paper (to prevent damage especially on the lamina) before placing on the solid SIM medium. The approximately 5 explants (Method A) or 10 to 20 (Methods B and C) explants were placed such that the target tissue was in direct contact with the medium. During the first 2 weeks, the explants could be cultured with or without selective medium. Preferably, explants were transferred onto SIM without selection for one week.

For leaf explants (Method B), the explant should be placed into the medium such that it is perpendicular to the surface of the medium with the petiole imbedded into the medium and the lamina out of the medium.

For propagated axillary meristem (Method C), the explant was placed into the medium such that it was parallel to the surface of the medium (basipetal) with the explant partially embedded into the medium.

Wrap plates with Scotch 394 venting tape (3M, St. Paul, Minn., USA) were placed in a growth chamber for two weeks with a temperature averaging 25° C. under 18 h light/6 h dark cycle at 70-100 $pE/m^2s$. The explants remained on the SIM medium with or without selection until de novo shoot growth occurred at the target area (e.g., axillary meristems at the first node above the epicotyl). Transfers to fresh medium can occur during this time. Explants were transferred from the SIM with or without selection to SIM with selection after about one week. At this time, there was considerable de novo shoot development at the base of the petiole of the leaf explants in a variety of SIM (Method B), at the primary node for seedling explants (Method A), and at the axillary nodes of propagated explants (Method C).

Preferably, all shoots formed before transformation were removed up to 2 weeks after co-cultivation to stimulate new growth from the meristems. This helped to reduce chimerism in the primary transformant and increase amplification of transgenic meristematic cells. During this time the explant may or may not be cut into smaller pieces (i.e. detaching the node from the explant by cutting the epicotyl).

3.5—Shoot Elongation

After 2 to 4 weeks (or until a mass of shoots was formed) on SIM medium (preferably with selection), the explants were transferred to SEM medium (shoot elongation medium, see Olhoft et al 2007 A novel Agrobacterium rhizogenes-mediated transformation method of soy using primary-node explants from seedlings. In Vitro Cell. Dev. Biol.—Plant (2007) 43:536-549) that stimulates shoot elongation of the shoot primordia. This medium may or may not contain a selection compound.

After every 2 to 3 weeks, the explants were transferred to fresh SEM medium (preferably containing selection) after carefully removing dead tissue. The explants should hold together and not fragment into pieces and retain somewhat healthy. The explants were continued to be transferred until the explant dies or shoots elongate. Elongated shoots >3 cm were removed and placed into RM medium for about 1 week (Method A and B), or about 2 to 4 weeks depending on the cultivar (Method C) at which time roots began to form. In the case of explants with roots, they were transferred directly into soil. Rooted shoots were transferred to soil and hardened in a growth chamber for 2 to 3 weeks before transferring to the greenhouse. Regenerated plants obtained using this method were fertile and produced on average 500 seeds per plant.

After 5 days of co-cultivation with Agrobacterium tumefaciens transient expression of the gene of interest (GOI) was widespread on the seedling axillary meristem explants especially in the regions wounding during explant preparation (Method A). Explants were placed into shoot induction medium without selection to see how the primary-node responds to shoot induction and regeneration. Thus far, greater than 70% of the explants were formed new shoots at this region. Expression of the GOI was stable after 14 days on SIM, implying integration of the T-DNA into the soy genome. In addition, preliminary experiments resulted in the formation of cDNA expressing shoots forming after 3 weeks on SIM.

For Method C, the average regeneration time of a soy plantlet using the propagated axillary meristem protocol was 14 weeks from explant inoculation. Therefore, this method has a quick regeneration time that leads to fertile, healthy soy plants.

Example 4: Pathogen Assay 4.1. Recovery of Clones 2-3 clones per To event were potted into small 6 cm pots. For recovery the clones were kept for 12-18 days in the phytochamber (16 h-day- and 8 h-night-Rhythm at a temperature of 16-22° C. and a humidity of 75%).

4.2 Inoculation

The Plants were Inoculated with *P. pachyrhizi*.

In order to obtain appropriate spore material for the inoculation, soy leaves which had been infected with rust 15-20 days ago, were taken 2-3 days before the inoculation and transferred to agar plates (1% agar in H2O). The leaves were placed with their upper side onto the agar, which allowed the fungus to grow through the tissue and to produce very young spores. For the inoculation solution, the spores were knocked off the leaves and were added to a Tween-H2O solution. The counting of spores was performed under a light microscope by means of a Thoma counting chamber. For the inoculation of the plants, the spore suspension was added into a compressed-air operated spray flask and applied uniformly onto the plants or the leaves until the leaf surface is well moisturized. For macroscopic assays we used a spore density of 1-5×105 spores/ml. For the microscopy, a density of >5×105 spores/ml is used. The inoculated plants were placed for 24 hours in a greenhouse chamber with an average of 22° C. and >90% of air humidity. The following cultivation was performed in a chamber with an average of 25° C. and 70% of air humidity.

Example 5: Microscopical Screening

For the evaluation of the pathogen development, the inoculated leaves of plants were stained with aniline blue 48 hours after infection.

The aniline blue staining serves for the detection of fluorescent substances. During the defense reactions in host interactions and non-host interactions, substances such as phenols, callose or lignin accumulated or were produced and were incorporated at the cell wall either locally in papillae or in the whole cell (hypersensitive reaction, HR). Complexes were formed in association with aniline blue, which lead e.g. in the case of callose to yellow fluorescence. The leaf material was transferred to falcon tubes or dishes containing destaining solution II (ethanol/acetic acid 6/1) and was incubated in a water bath at 90° C. for 10-15 minutes. The destaining solution II was removed immediately thereafter, and the leaves were washed 2× with water. For the staining, the leaves were incubated for 1.5-2 hours in staining solution II (0.05% aniline blue=methyl blue, 0.067 M di-potassium hydrogen phosphate) and analyzed by microscopy immediately thereafter.

The different interaction types were evaluated (counted) by microscopy. An Olympus UV microscope BX61 (incident light) and a UV Longpath filter (excitation: 375/15, Beam splitter: 405 LP) are used. After aniline blue staining, the spores appeared blue under UV light. The papillae could be recognized beneath the fungal appressorium by a green/yellow staining. The hypersensitive reaction (HR) was characterized by a whole cell fluorescence.

Example 6: Evaluating the Susceptibility to Soybean Rust

The progression of the soybean rust disease was scored by the estimation of the diseased area (area which was covered by sporulating uredinia) on the backside (abaxial side) of the leaf. Additionally the yellowing of the leaf was taken into account (for scheme see FIG. 1).

To soybean plants expressing OCP3 protein were inoculated with spores of *Phakopsora pachyrhizi*. The macroscopic disease symptoms of soy against *P. pachyrhizi* of 33 $T_0$ soybean plants were scored 14 days after inoculation.

The average of the percentage of the leaf area showing fungal colonies or strong yellowing/browning on all leaves was considered as diseased leaf area. At all 33 soybean $T_0$ plants expressing OCP3 (expression checked by RT-PCR) were evaluated in parallel to non-transgenic control plants. Clones from non-transgenic soy plants were used as control. The average of the diseased leaf area is shown in FIG. 6 for plants expressing recombinant OCP3 compared with wild-type plants. Overexpression of OCP3 reduces the diseased leaf area in comparison to non-transgenic control plants by 30.2% in average over all events generated. This data clearly indicates that the in-planta expression of the OCP3 expression vector construct leads to a lower disease scoring of transgenic plants compared to non-transgenic controls. So, the overexpression of OCP3 (as shown in SEQ ID NO: 1) in the soybean epidermis significantly (p<0.01) increases the resistance of soy against soybean rust.

The invention claimed is:

1. A method for increasing soybean rust resistance in a soybean plant, a soybean plant part, or a soybean plant cell, said method comprising transforming a soybean plant, plant part, or plant cell with an exogenous nucleic acid encoding an OCP3 protein comprising an amino acid sequence with at least 90% identity to SEQ ID NO:2, wherein any differences between the amino acid sequence of SEQ ID NO: 2 and the amino acid sequence of the OCP3 protein are conservative amino acid substitutions, and wherein the OCP3 protein confers increased resistance against soybean rust thereto in comparison to a wild type soybean plant, wild type soybean plant part or wild type soybean plant cell.

2. The method of claim 1, comprising:

(a) stably transforming a soybean plant cell with an expression cassette comprising:

an exogenous nucleic acid encoding a protein having an amino acid sequence with at least 90% identity to SEQ ID NO: 2 in functional linkage with a promoter, wherein any differences between the amino acid sequence of SEQ ID NO: 2 and the amino acid sequence of the OCP3 protein are conservative amino acid substitutions; and (b) regenerating the plant from the plant cell.

3. A recombinant vector construct comprising:

(a) a nucleic acid encoding an OCP3 protein having an amino acid sequence with at least 90% identity to SEQ ID NO: 2, wherein any differences between the amino acid sequence of SEQ ID NO: 2 and the amino acid sequence of the OCP3 protein are conservative amino acid substitutions, operably linked with (b) a fungal-inducible promoter; and (c) a transcription termination sequence, wherein expression of said recombinant vector construct in a soybean plant, soybean plant part, or soybean plant cell confers increased resistance against soybean rust thereto in comparison to a wild type soybean plant, wild type soybean plant part, or wild type soybean plant cell.

4. The method of claim 2, wherein the promoter is a constitutive, pathogen-inducible promoter, a mesophyll-specific promoter or an epidermis specific-promoter.

5. A transgenic plant, transgenic plant part, or transgenic plant cell comprising an exogenous nucleic acid encoding an OCP3 protein comprising an amino acid sequence with at least 90% identity to SEQ ID NO:2 operably linked to a fungal-inducible promoter, wherein any differences between the amino acid sequence of SEQ ID NO: 2 and the amino acid sequence of the OCP3 protein are conservative amino acid substitutions, and wherein the OCP3 protein confers increased resistance against soybean rust thereto in comparison to a wild type plant, wild type plant part, or wild type plant cell.

6. A method for the production of a transgenic plant, transgenic plant part, or transgenic plant cell having increased resistance against soybean rust, comprising (a) introducing the recombinant vector construct of claim 3 into a plant, a plant part, or a plant cell; and (b) generating a transgenic plant, transgenic plant part, or transgenic plant cell from the plant, plant part or plant cell.

7. The method of claim 6, further comprising the step of harvesting the seeds of the transgenic plant and planting the seeds and growing the seeds to plants, wherein the grown plants comprise the exogenous nucleic acid encoding a protein having an amino acid sequence with at least 90% identity to SEQ ID NO: 2.

8. A harvestable part of the transgenic plant of claim 5, wherein the harvestable part of the transgenic plant comprises the exogenous nucleic acid.

9. A product derived from the plant of claim 5, wherein the product comprises the exogenous nucleic acid.

10. A method for the production of a product comprising:
a) growing the plant of claim 5; and
b) producing said product from or by the plant and/or part of the plant
wherein the product comprises the exogenous nucleic acid.

11. The method of claim 1, wherein the resistance against soybean rust is resistance against *Phakopsora meibomiae* and/or *Phakopsora pachyrhizi*.

12. A method for breeding a fungal resistant plant comprising:
(a) crossing the plant of claim 5 with a second plant;
(b) obtaining seed from the cross of step (a);
(c) planting said seeds and growing the seeds to plants; and
(d) selecting from the plants produced in step (c) plants expressing the OCP3 protein.

13. A method for controlling soybean rust in a soybean plant, said method comprising providing a transgenic soybean plant comprising a nucleic acid encoding an OCP3 protein having an amino acid sequence with at least 90% identity to SEQ ID NO: 2, wherein any differences between the amino acid sequence of SEQ ID NO: 2 and the amino acid sequence of the OCP3 protein are conservative amino acid substitutions, and wherein expression of the nucleic acid leads to increased soybean rust resistance in said soybean plant as compared to a wild type soybean plant such that soybean rust is controlled in the transgenic soybean plant.

14. The method of claim 13, wherein the soybean rust that is controlled is *Phakopsora meibomiae* and/or *Phakopsora pachyrhizi*.

15. A transgenic soybean plant, transgenic soybean plant part, or transgenic soybean plant cell comprising an exogenous nucleic acid encoding an OCP3 protein comprising an amino acid sequence with at least 90% identity to SEQ ID NO:2, wherein any differences between the amino acid sequence of SEQ ID NO: 2 and the amino acid sequence of the OCP3 protein are conservative amino acid substitutions, and wherein the OCP3 protein confers increased resistance against soybean rust thereto in comparison to a wild type soybean plant, wild type soybean plant part, or wild type soybean plant cell.

16. A method for increasing soybean rust resistance in a soybean plant, a soybean plant part, or a soybean plant cell, said method comprising transforming a soybean plant, plant part, or plant cell with an exogenous nucleic acid encoding an OCP3 protein comprising an amino acid sequence with at least 95% identity to SEQ ID NO:2,
wherein the OCP3 protein confers increased resistance against soybean rust thereto in comparison to a wild type soybean plant, wild type soybean plant part or wild type soybean plant cell.

17. The method of claim 16, wherein the exogenous nucleic acid encoding an OCP3 protein comprises an amino acid sequence with at least 98% identity to SEQ ID NO:2.

18. The method of claim 16, wherein the exogenous nucleic acid encoding an OCP3 protein comprises an amino acid sequence having 100% identity to SEQ ID NO:2.

19. A method for controlling soybean rust in a soybean plant, said method comprising providing a transgenic soybean plant comprising a nucleic acid encoding an OCP3 protein having an amino acid sequence with at least 95% identity to SEQ ID NO: 2, wherein expression of the nucleic acid leads to increased soybean rust resistance in said soybean plant as compared to a wild type soybean plant such that soybean rust is controlled in the transgenic soybean plant.

20. The method of claim 19, wherein the exogenous nucleic acid encoding an OCP3 protein comprises an amino acid sequence with at least 98% identity to SEQ ID NO:2.

21. The method of claim 19, wherein the exogenous nucleic acid encoding an OCP3 protein comprises an amino acid sequence having 100% identity to SEQ ID NO:2.

22. A transgenic soybean plant, transgenic soybean plant part, or transgenic soybean plant cell comprising an exogenous nucleic acid encoding an OCP3 protein comprising an amino acid sequence with at least 95% identity to SEQ ID NO:2, wherein the OCP3 protein confers increased resistance against soybean rust thereto in comparison to a wild type soybean plant, wild type soybean plant part, or wild type soybean plant cell.

23. The transgenic soybean plant, transgenic soybean plant part, or transgenic soybean plant cell of claim 22, wherein the exogenous nucleic acid encoding an OCP3 protein comprises an amino acid sequence with at least 98% identity to SEQ ID NO:2.

24. The transgenic soybean plant, transgenic soybean plant part, or transgenic soybean plant cell of claim 22, wherein the exogenous nucleic acid encoding an OCP3 protein comprises an amino acid sequence having 100% identity to SEQ ID NO:2.

* * * * *